United States Patent
Shani et al.

(10) Patent No.: US 11,130,796 B2
(45) Date of Patent: Sep. 28, 2021

(54) SIRPALPHA-41BBL FUSION PROTEIN AND METHODS OF USE THEREOF

(71) Applicant: KAHR Medical Ltd., Jerusalem (IL)

(72) Inventors: Noam Shani, Zikhron-Yaakov (IL); Yosi Gozlan, Rehovot (IL); Michal Dranitzki Elhalel, Shoresh (IL); Edwin Bremer, Groningen (NL); Ido Kaminsky, Ramat-Gan (IL)

(73) Assignee: KAHR Medical Ltd., Jerusalem (IL)

( * ) Notice: Subject to any disclaimer, the term of this patent is extended or adjusted under 35 U.S.C. 154(b) by 0 days.

(21) Appl. No.: 16/473,631

(22) PCT Filed: Jan. 4, 2018

(86) PCT No.: PCT/IL2018/050017
§ 371 (c)(1),
(2) Date: Jun. 26, 2019

(87) PCT Pub. No.: WO2018/127919
PCT Pub. Date: Jul. 12, 2018

(65) Prior Publication Data
US 2019/0352372 A1 Nov. 21, 2019

Related U.S. Application Data

(60) Provisional application No. 62/442,469, filed on Jan. 5, 2017.

(51) Int. Cl.
| | |
|---|---|
| *C07K 19/00* | (2006.01) |
| *C07K 14/705* | (2006.01) |
| *A61P 35/00* | (2006.01) |
| *A61K 38/17* | (2006.01) |
| *A61K 47/65* | (2017.01) |
| *A61P 35/02* | (2006.01) |
| *C07K 16/28* | (2006.01) |
| *C12N 5/0783* | (2010.01) |
| *C12N 15/85* | (2006.01) |
| *A61K 38/00* | (2006.01) |

(52) U.S. Cl.
CPC ........ *C07K 14/70578* (2013.01); *A61K 47/65* (2017.08); *A61P 35/02* (2018.01); *C07K 14/70596* (2013.01); *C07K 16/2863* (2013.01); *C07K 16/2887* (2013.01); *C07K 16/2893* (2013.01); *C12N 5/0638* (2013.01); *C12N 15/85* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,287,386 A | 2/1994 | Wade et al. | |
| 5,674,704 A | 10/1997 | Goodwin et al. | |
| 6,046,048 A | 4/2000 | Ashkenazi et al. | |
| 6,740,739 B1 | 5/2004 | Ashkenazi et al. | |
| 7,142,018 B2 | 11/2006 | Masleid et al. | |
| 7,279,925 B1 | 10/2007 | Richmond et al. | |
| 7,569,663 B2 | 8/2009 | Tykocinski et al. | |
| 8,039,437 B2 | 10/2011 | Tykocinski et al. | |
| 8,216,805 B2 | 7/2012 | Carter et al. | |
| 9,562,087 B2 | 2/2017 | Ring et al. | |
| 10,040,841 B2 | 8/2018 | Dranitzki Elhalel et al. | |
| 10,464,981 B2 | 11/2019 | Amann et al. | |
| 2003/0216546 A1 | 11/2003 | Tykocinski et al. | |
| 2007/0036783 A1 | 2/2007 | Humeau et al. | |
| 2007/0110746 A1 | 5/2007 | Chung | |
| 2012/0189625 A1 | 7/2012 | Wang et al. | |
| 2013/0094307 A1 | 4/2013 | Cheng | |
| 2013/0287802 A1 | 10/2013 | Govindappa et al. | |
| 2015/0183881 A1 | 7/2015 | Bedi et al. | |
| 2015/0353642 A1* | 12/2015 | Tykocinski ............ | C07K 14/78 514/19.4 |
| 2015/0376260 A1 | 12/2015 | Elhalel et al. | |
| 2016/0039903 A1 | 2/2016 | Ring et al. | |
| 2017/0107270 A1 | 4/2017 | Pons et al. | |
| 2017/0327588 A1 | 11/2017 | Baca et al. | |
| 2019/0016782 A1 | 1/2019 | Dranitzki Elhalel et al. | |
| 2019/0151413 A1 | 5/2019 | Schreiber et al. | |
| 2019/0315834 A1 | 10/2019 | Shani et al. | |
| 2019/0330304 A1 | 10/2019 | Shani et al. | |

(Continued)

FOREIGN PATENT DOCUMENTS

| | | |
|---|---|---|
| CN | 107857819 | 3/2018 |
| WO | WO 01/049318 | 7/2001 |

(Continued)

OTHER PUBLICATIONS

International Preliminary Report on Patentability dated Jan. 21, 2021 From the International Bureau of WIPO Re. Application No. PCT/IL2019/050782. (9 Pages).

Supplementary European Search Report and the European Search Opinion dated Nov. 19, 2020 From the European Patent Office Re. Application No. 18736642.2. (12 Pages).

Ascierto et al. "Clinical Experiences With Anti-CD137 and Anti-PD1 Therapeutic Antibodies", Seminars in Oncology, XP008175440, 27(5): 508-516, Oct. 1, 2010.

Sanmamed et al. "Agonists of Co-Stimulation in Cancer Immunotherapy Directed Against CD137, OX40, GITR, CD27, CD28, and ICOS", Seminars in Oncology, XP055410294, 42(4): 640-655, Aug. 1, 2015.

(Continued)

*Primary Examiner* — Julie Ha
*Assistant Examiner* — Kristina M Hellman

(57) ABSTRACT

SIRP1alpha-41BBL fusion proteins are provided. Accordingly, there is provided a SIRPalpha-41BBL fusion protein comprising a single amino acid linker between the SIRPalpha and the 41BBL. Also there is provided a SIRPalpha-41BBL fusion protein in a form of at least a homo-trimer. Also provided are polynucleotides and nucleic acid constructs encoding the SIRP1alpha-41BBL fusion protein, host-cells expressing the SIRP1alpha-41BBL fusion protein and methods of use thereof.

11 Claims, 13 Drawing Sheets

Specification includes a Sequence Listing.

(56) References Cited

U.S. PATENT DOCUMENTS

| | | |
|---|---|---|
| 2019/0352371 A1 | 11/2019 | Tykocinski et al. |
| 2020/0317773 A1 | 10/2020 | Clark et al. |

FOREIGN PATENT DOCUMENTS

| | | |
|---|---|---|
| WO | WO 01/75067 | 10/2001 |
| WO | WO 01/86003 | 11/2001 |
| WO | WO 03/046581 | 6/2003 |
| WO | WO 2010/027828 | 3/2010 |
| WO | WO 2011/109789 | 9/2011 |
| WO | WO 2012/042480 | 4/2012 |
| WO | WO 2013/064700 | 5/2013 |
| WO | WO 2013/112986 | 8/2013 |
| WO | WO 2013/144704 | 10/2013 |
| WO | WO 2014/106839 | 7/2014 |
| WO | WO 2014/121093 | 8/2014 |
| WO | WO 2014/180288 | 11/2014 |
| WO | WO 2015/148416 | 10/2015 |
| WO | WO 2016/022994 | 2/2016 |
| WO | WO 2016/023001 | 2/2016 |
| WO | WO 2016/024021 | 2/2016 |
| WO | WO 2016/063233 | 4/2016 |
| WO | WO 2016/090312 | 6/2016 |
| WO | WO 2017/194641 | 6/2016 |
| WO | WO 2016/139668 | 9/2016 |
| WO | WO 2016/187226 | 11/2016 |
| WO | WO 2017/012770 | 1/2017 |
| WO | WO 2017/019846 | 2/2017 |
| WO | WO 2017/027422 | 2/2017 |
| WO | WO 2017/059168 | 4/2017 |
| WO | WO 2017/068192 | 4/2017 |
| WO | WO 2017/152132 | 9/2017 |
| WO | WO 2017/194641 | 11/2017 |
| WO | WO 2018/006881 | 1/2018 |
| WO | WO 2018/032793 | 2/2018 |
| WO | WO 2018/053885 | 3/2018 |
| WO | WO 2018/085358 | 5/2018 |
| WO | WO 2018/127916 | 7/2018 |
| WO | WO 2018/127916 A9 | 7/2018 |
| WO | WO 2018/127917 | 7/2018 |
| WO | WO 2018/127918 | 7/2018 |
| WO | WO 2018/127918 A9 | 7/2018 |
| WO | WO 2018/127919 | 7/2018 |
| WO | WO 2018/127919 A9 | 7/2018 |
| WO | WO 2019/086499 | 5/2019 |
| WO | WO 2020/012486 | 1/2020 |
| WO | WO 2020/012485 A9 | 5/2020 |
| WO | WO 2020/146423 | 7/2020 |
| WO | WO 2021/005599 | 1/2021 |

OTHER PUBLICATIONS

Xiao et al. "Soluble PD-1 Facilitates 4-1BBL-Triggered Antitumor Immunity Against Murine H22 Hepatocarcinoma In Vivo", Clinical Cancer Research, XP055144430, 13(6): 1823-1830, Published Online Feb. 26, 2007.
Zhang et al. "Targeted and Untargeted CD137L Fusion Proteins for the Immunotherapy of Experimental Solid Tumors", Clinical Cancer Research, XP055186494, 13(9): 2758-2767, May 1, 2007.
Supplementary European Search Report and the European Search Opinion dated Oct. 12, 2020 From the European Patent Office Re. Application No. 18735930.2. (8 Pages).
Gozlan et al. "Abstract A076: DSP107-A novel SIRPα-4-1 BBL Dual Signaling Protein (DSP) for Cancer immunotherapy", Cancer Immunology Research, XP55734527A,7(2): 2P., Feb. 2019.
Official Action dated Nov. 13, 2020 from the US Patent and Trademark Office Re. U.S. Appl. No. 16/027,382. (41 pages).
Communication Pursuant to Article 94(3) EPC dated Jun. 1, 2017 From the European Patent Office Re. Application No. 13827047.5. (4 Pages).
Communication Pursuant to Article 94(3) EPC dated Feb. 6, 2018 From the European Patent Office Re. Application No. 13827047.5. (5 Pages).
Communication Pursuant to Article 94(3) EPC dated Sep. 26, 2016 From the European Patent Office Re. Application No. 13827047.5. (3 Pages).
Communication Pursuant to Rules 161(1) and 162 EPC dated Sep. 10, 2015 From the European Patent Office Re. Application No. 13827047.5. (2 Pages).
Examination Report dated Jul. 11, 2017 From the Australian Government, IP Australia Re. Application No. 2013371826.(4 Pages).
Examination Report dated Mar. 28, 2018 From the Australian Government, IP Australia Re. Application No. 2013371826.(2 Pages).
International Preliminary Report on Patentability dated Jul. 16, 2015 From the International Bureau of WIPO Re. Application No. PCT/IL2013/051098. (14 Pages).
International Preliminary Report on Patentability dated Jul. 18, 2019 From the International Bureau of WIPO Re. Application No. PCT/IL2018/050014. (7 Pages).
International Preliminary Report on Patentability dated Jul. 18, 2019 From the International Bureau of WIPO Re. Application No. PCT/IL2018/050015. (7 Pages).
International Preliminary Report on Patentability dated Jul. 18, 2019 From the International Bureau of WIPO Re. Application No. PCT/IL2018/050016. (7 Pages).
International Preliminary Report on Patentability dated Jul. 18, 2019 From the International Bureau of WIPO Re. Application No. PCT/IL2018/050017. (7 Pages).
International Search Report and the Written Opinion dated Mar. 13, 2018 From the International Searching Authority Re. Application No. PCT/IL2018/050015. (11 Pages).
International Search Report and the Written Opinion dated Mar. 13, 2018 From the International Searching Authority Re. Application No. PCT/IL2018/050016. (11 Pages).
International Search Report and the Written Opinion dated May 15, 2014 From the International Searching Authority Re. Application No. PCT/IL2013/051098. (19 Pages).
International Search Report and the Written Opinion dated Sep. 16, 2019 From the International Searching Authority Re. Application No. PCT/IL2019/050783. (15 Pages).
International Search Report and the Written Opinion dated Sep. 18, 2019 From the International Searching Authority Re. Application No. PCT/IL2019/050782. (16 Pages).
International Search Report and the Written Opinion dated Feb. 25, 2018 From the International Searching Authority Re. Application No. PCT/IL2018/050017. (11 Pages).
International Search Report and the Written Opinion dated Feb. 27, 2018 From the International Searching Authority Re. Application No. PCT/IL2018/050014. (11 Pages).
Notification of Office Action and Search Report dated Dec. 15, 2017 From the State Intellectual Property Office of the People's Republic of China Re. Application No. 201380074192.4. (7 Pages).
Notification of Office Action dated Jul. 10, 2018 From the State Intellectual Property Office of the People's Republic of China Re. Application No. 201380074192.4. and Its Summary in English. (5 Pages).
Office Action dated Aug. 14, 2018 From the Israel Patent Office Re. Application No. 239671 and Its Translation Into English. (7 Pages).
Official Action dated Oct. 6, 2017 From the US Patent and Trademark Office Re. U.S. Appl. No. 14/655,752. (9 pages).
Official Action dated Mar. 30, 2017 From the US Patent and Trademark Office Re. U.S. Appl. No. 14/655,752. (12 Pages).
Restriction Official Action dated Jun. 15, 2016 From the US Patent and Trademark Office Re. U.S. Appl. No. 14/655,752. (7 Pages).
Translation Dated Jul. 25, 2018 of Notification of Office Action dated Jul. 10, 2018 From the State Intellectual Property Office of the People's Republic of China Re. Application No. 201380074192.4. (5 Pages).
Translation of Notification of Office Action and Search Report dated Dec. 15, 2017 From the State Intellectual Property Office of the People's Republic of China Re. Application No. 201380074192.4. (9 Pages).
Absolute Antibody "Antibody Sequencing, Engineering & Recombinant Expression", Absolute Antibody, Home Products, Website, 3 P., 2019.

(56) References Cited

OTHER PUBLICATIONS

Absolute Antibody "Bispecific and Trispecific Antibodies", Absolute Antibody, Website, Home Products, Website, 3 P., 2019.
Absolute Antibody "Products Archive", Absolute Antibody, Home Products, Website, 2 P., 2019.
Antoniou et al. "Transgenes Excompassing Dual-Promoter CpG Islands From the Human TBPand HNRPA2B1 Loci Are Resistant to Heterochromatin-Mediated Silencing", Genomics, 82(3): 269-279, Sep. 2003.
Arora et al. "Belatacept: A New Biological Agent for Maintenance Immunosuppression in Kidney Transplantation", Expert Opinion on Biological Therapy, 12(7): 965-979, Published Online May 8, 2012.
Beha et al. "IL-15-Based Trifunctional Antibody-Fusion Proteins With Costimulatory TNF-Superfamily Ligands in the Single-Chain Format for Cancer Immunotherapy", Molecular Cancer Therapeutics, p. 1-35, Published Ahead of Print Apr. 30, 2019.
Dranitzki-Elhalel et al. CD40•FasL Inhibits Human T Cells: Evidence for an Auto-Inhibitory Loop-Back Mechanism, International Immunology, XP001668353, 19(4): 355-363, Advance Access Publication Feb. 20, 2007.
Eisele et al. "APO010, A Synthetic Hexameric CD95 Ligand, Induces Human Glioma Cell Death In Vitro and In Vivo", Neuro-Oncology, 13(2): 155-164, Published Online Dec. 22, 2010.
Fellermeier et al. "Advancing Targeted Co-Stimulation With Antibody-Fusion Proteins by Introducing TNF Superfamily Members in a Single-Chain Format", Oncoimmunology, 5(11): e1238540-1-e1238540-11, Sep. 27, 2016.
Feng et al. "CTLA4-Fas Ligand Gene Transfer Mediated by Adenovirus Induce Long-Time Survival of Murine Cardiac Allografts", Transplantation Proceedings, 37(5): 2379-2381, Jun. 2005.
Herrero-Beaumont et al. "Abatacept Mechanism of Action: Concordance With Its Clinical Profile?", Reumatologia Clinica, 8(2): 78-83, Available Online Feb. 15, 2012.
Holler et al. "Two Adjacent Trimeric Fas Ligands Are Required for Fas Signaling and Formation of a Death-Inducing Signaling Complex", Molecular and Cellular Biology, XP002258597, 23(4): 1428-1440, Feb. 2003. Abstract.
Huang et al. "CTLA-4-Fas Ligand Functions as a Trans Signal Converter Protein in Bridging Antigen-Presenting Cells and T Cells", International Immunology, XP001147390, 13(4): 529-539, Apr. 1, 2001. p. 537, r-h Col., Last Para, Fig. 1.
Jin et al. "Simultaneous Stimulation of Fas-Mediated Apoptosis and Blockade of Costimualtion Prevent Autoimmune Diabetes in Mice Induced by Multiple Low-Dose Streptozotocin", Gene Therapy, 11(12): 982-991, Published Online Mar. 25, 2004.
Kahr Medical "DSP105 (PD1-41BBL): Targeted Immune Activation Leading to T-Cell Mediated Tumor Destruction", Kahr Medical, Product Description, p. 1-4, Apr. 29, 2018.
Lazar-Molnar et al. "Crystal Structure of the Complex Between Programmed Death-1 (PD-1) and Its Ligand PD-2", Proc. Natl. Acad. Sci. USA, PNAS, 105(30): 10483-10488, Jul. 29, 2008.
Locksley et al. "The TNF and TNF Receptor Superfamilies: Integrating Mammalian Biology", Cell, 104(4): 487-501, Feb. 23, 2001.
Maute et al. "Engineering High-Affinity PD-1 Variants for Optimized Immunotherapy and Ommuno-PET Omaging", Proceedings of the National Academy of Sciences, 112 (47): E6506-E6514, Published Online Nov. 10, 2015.
Merchant et al. "An Efficient Route to Human Bispecific IgG", Nature Biotechnology, 16(7): 677-681, Jul. 1998.
Nalamalpu et al. "Booster for Driving Long Onchip Interconnects—Design Issues, Interconnect Synthesis, and Comparison With Repeaters", IEEE Transactions on Computer-Aided Design of Integrated Circuits and Systems, 21(1): 50-62, Jan. 2002.
Orbach et al. "CD40• FasL and CTLA-4• FasL Fusion Proteins Induce Apoptosis in Malignant Cell Lines by Dual Signaling", The American Journal of Pathology, XP009155963, 177(6): 3159-3168, Dec. 2010. Abstract.
Orbach et al. "CTLA-4 • FasL Induces Early Apoptosis of Activated T Cells by Interfering With Anti-Apoptotic Signals", The Journal of Immunology, XP002668354, 179(11): 7287-7294, Dec. 1, 2007.

Pereg "Kahr Medical Dual Signaling Proteins (DSP) Platform—The Next Generation of Cancer Immunotherapy", Kahr Medical, Abstract Template for Company Presentations, 1 P., May 11, 2018.
Shi et al. "Prolongation of Corneal Allograft Survival by CTLA4-FasL in a Murine Model", Graefe's Archive for Clinical and Experimental Ophthalmology, XP019542074, 245(11): 1691-1697, Published Online May 31, 2007.
Shrimali et al. "Concurrent PD-1 Blockade Negates the Effects of OX40 Agonist in Combination Immunotherapy Through Inducing T-Cell Apoptosis", Cancer Immunology Research, 5(9): 755-766, Published Online Aug. 28, 2017.
Slavin et al. "Spontaneous Murine B-Cell Leukaemia", Nature, 272(5654): 624-626, Apr. 13, 1978.
Tansey et al. "The TNF Superfamily in 2009: New Pathways, New Indications, and New Drugs", Drug Discovery Today, 14(23/24): 1082-1088, Dec. 2009.
Weiskopf et al. Engineered SIRP-alpha Variants as Immunotherapeutic Adjuvants to Anti-cancer Antibodies, Science, 341 (6141): 88-91, Jul. 5, 2013.
Wyzgol et al. "Trimer Stabilization, Oligomerization, and Antibody-Mediated Cell Surface Immobilization Improve the Activity of Soluble Trimers of CD27L, CD40L, 41BBL, and Glucocorticoid-InducedTNF Receptor Ligands", The Journal of Immunology, 183(3): 1851-1861, Published Online Jun. 13, 2009.
Zhang et al. "Intraarticular Gene Delivery of CTLA4-FasL Suppresses Experimental Arthritis", International Immunology, 24(6): 379-388, Advance Access Publicaiton Feb. 21, 2012.
International Search Report and the Written Opinion dated Oct. 6, 2020 From the International Searching Authority Re. Application No. PCT/IL2020/050762. (13 Pages).
Restriction Official Action dated May 15, 2020 from the US Patent and Trademark Office Re. U.S. Appl. No. 16/027,382. (10 pages).
Search Report and Written Opinion dated Apr. 25, 2020 From the Intellectual Property Office of Singapore Re. Application No. 11201905679S.
Search Report and Written Opinion dated Apr. 25, 2020 From the Intellectual Property Office of Singapore Re. Application No. 11201905681W. (10 Pages).
International Preliminary Report on Patentability dated Jan. 21, 2021 From the International Bureau of WIPO Re. Application No. PCT/IL2019/050783. (8 Pages).
Request for Examination dated Apr. 9, 2021 From the (ROSPATENT), Federal Government Institution of Industrial Property of the Federal Service of Intellectual Property, Patents and Trademark of the Russian Federation Re. Application No. 2019124678 and Its Translation Into English. (33 Pages).
Frankel et al. Characterization of Diphtheria Fusion Proteins Targeted to the Human Interleukin-3 Receptor, Protein Engineering, Design and Selection,13(8);575-581, Aug. 1, 2000.
Yang et al. "High-Level Expression and Deletion Mutagenesis of Human Tryptophan Hydroxylase", Proceedings of the National Academy of Sciences of the United States of America, 91(14): 6659-6663, Jul. 5, 1994.
Restriction Official Action dated Mar. 26, 2021 from the US Patent and Trademark Office Re. U.S. Appl. No. 16/475,683. (9 pages).
Final Official Action dated May 12, 2021 From the US Patent and Trademark Office Re. U.S. Appl. No. 16/027,382. (15 Pages).
Patent Examination Report dated Apr. 6, 2021 From the Australian Government, IP Australia Re. Application No. 2018205890.(4 Pages).
Patent Examination Report dated Mar. 26, 2021 From the Australian Government, IP Australia Re. Application No. 2018205888. (4 Pages).
Request for Examination and Search Report dated Apr. 9, 2021 From the (ROSPATENT), Federal Government Institution of Industrial Property of the Federal Service of Intellectual Property, Patents and Trademark of the Russian Federation Re. Application No. 2019124676 and Its Translation Into English. (40 Pages).
Berry et al. "Substitution of Cysteine for Selenocysteine in Type I Iodothyronine Deiodinase Reduces the Catalytic Efficiency of the Protein But Enhances its Translation", Endocrinology, 131(4): 1848-1852, Oct. 1, 1992.

(56) References Cited

OTHER PUBLICATIONS

Chen et al. "Fusion Protein Linkers: Property, Design and Functionality", Advanced Drug Delivery Reviews, 65(10): 1357-1369, Oct. 15, 2013.
Gasser et al. "Antibody Production With Yeasts and Filamentous Fungi: On the Road to Large Scale?", Biotechnology Letters, 29: 201-212, Nov. 22, 2006.
Grewal et al. "CD40 and CD154 in Cell-Mediated Immunity", Annual Review of Immunology, 16:111-135, Publication date: Apr. 1998.
Halin et al. "Synergistic Therapeutic Effects of a Tumor Targeting Antibody Fragment, Fused to Interleukin 12 and to Tumor Necrosis Factor α", Cancer Research, 63(12):3202-3210, Jun. 15, 2003.
Kaiko et al. "Immunological Decision-Making: How Does The Immune System Decide To Mount A Helper T-Cell Response", Immunology,123(3):326-338, Jan. 18, 2008.
Kontermann et al. "Bispecific Antibodies", Drug Discovery Today, 20(7): 838-847, Jul. 2015.
Maeda et al. "Engineering of Functional Chimeric Protein G—Vargula Luciferase", Analytical Biochemistry,249 (2): 147-152, Jul. 1, 1997.
Muller et al. "Spliceosomal peptide P140 for Immunotherapy of Systemic Lupus Erythematosus: Results of an Early Phase II Clinical Trial", Arthritis and Rheumatology, 58(12): 3873-3883, Nov. 26, 2008.
Yu et al. "The Surface Protein TIGIT Suppresses T Cell Activation by Promoting the Generation of Mature Immunoregulatory Dendritic Cells", Nature Immunology, 10: 48-57, 2009.

\* cited by examiner

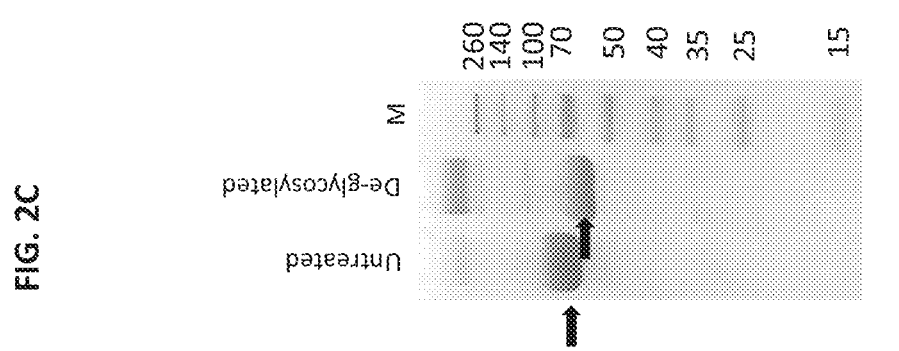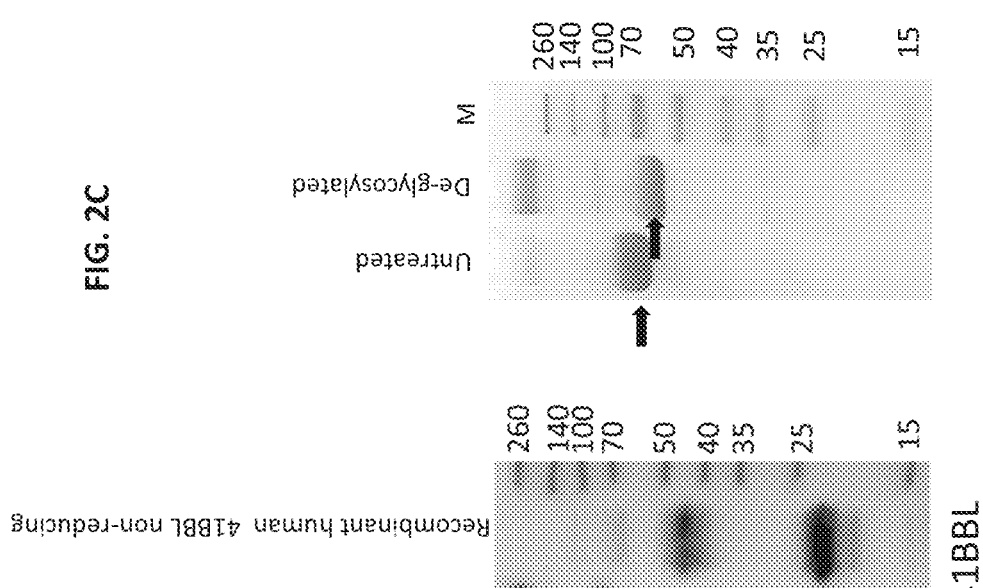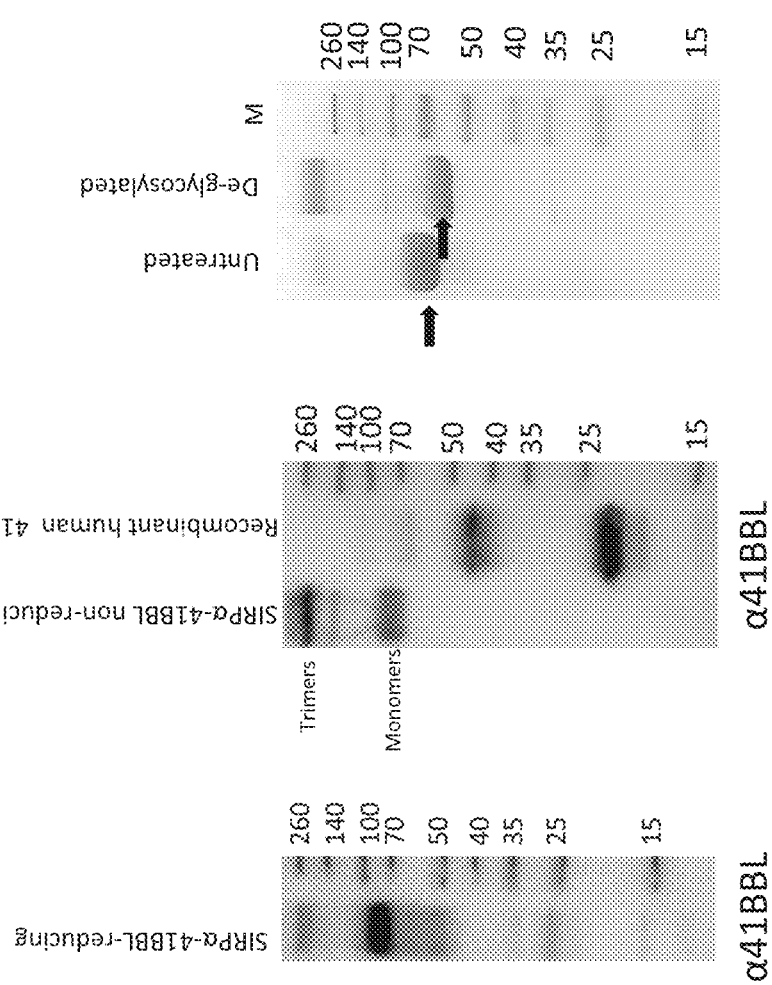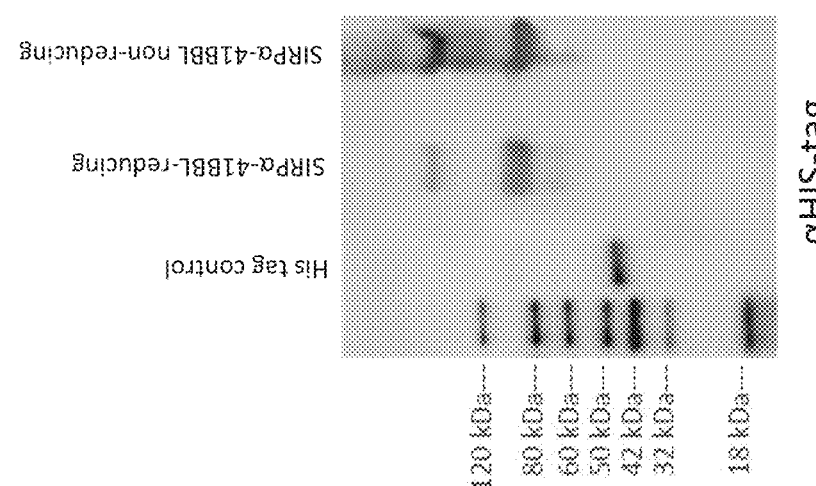

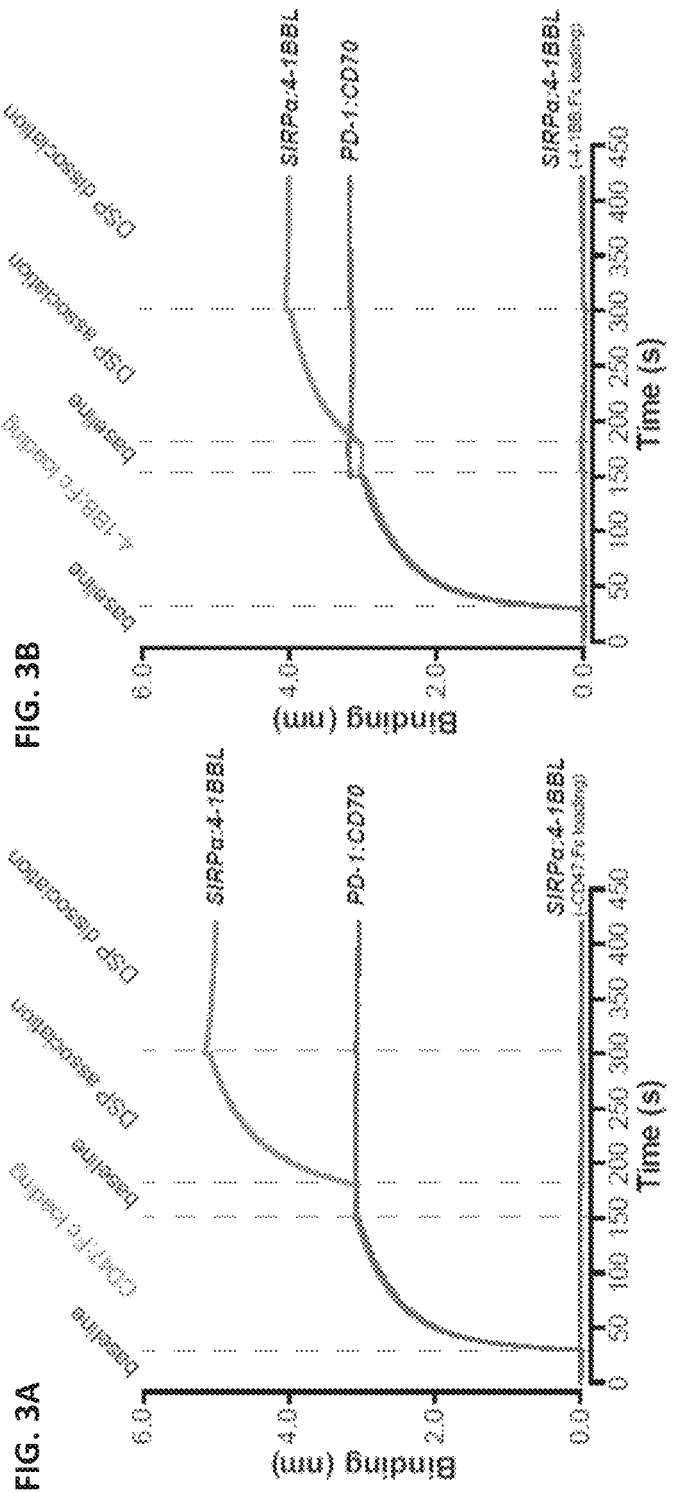

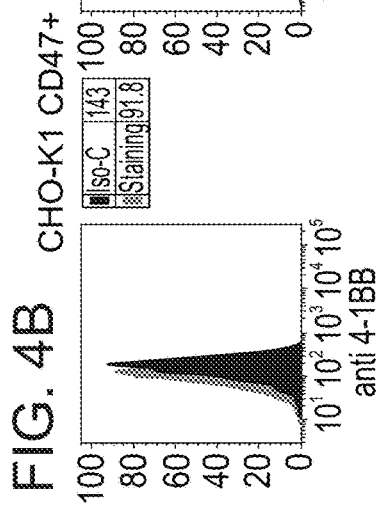
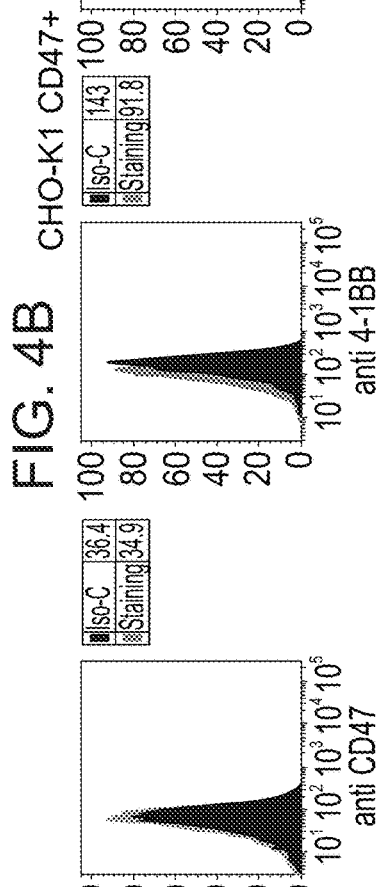
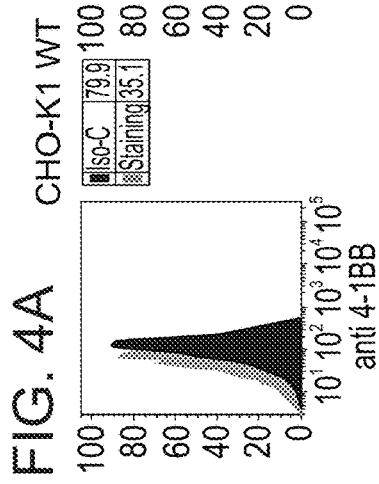
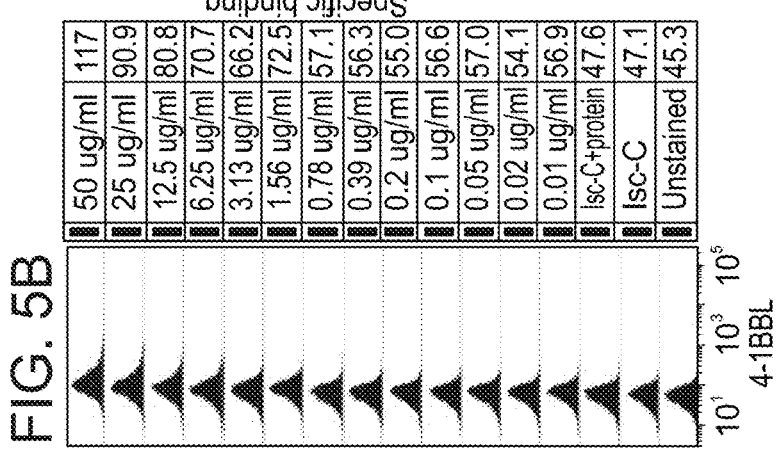
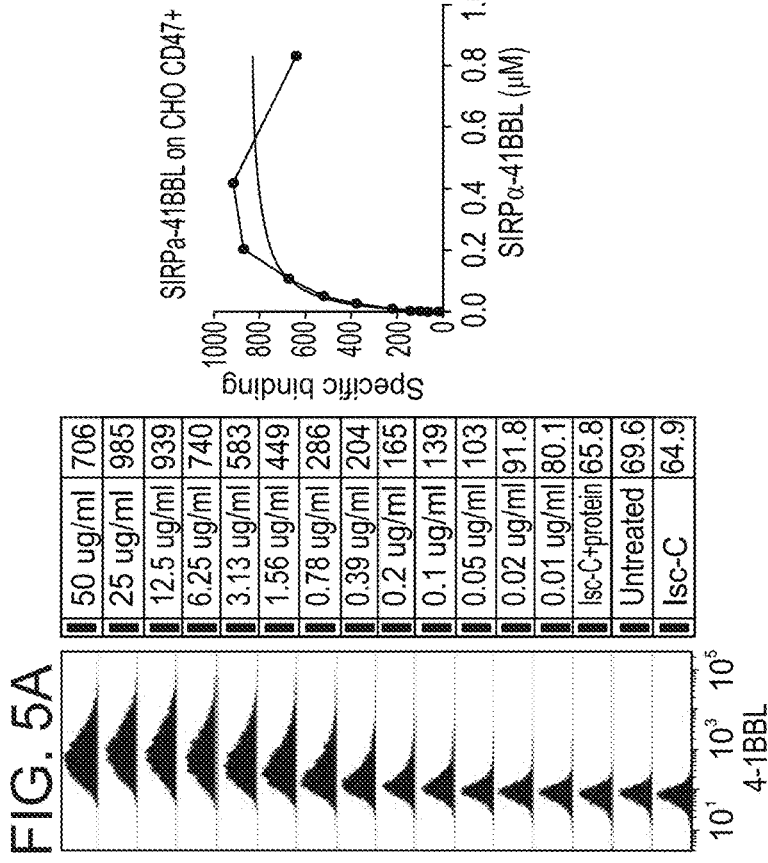

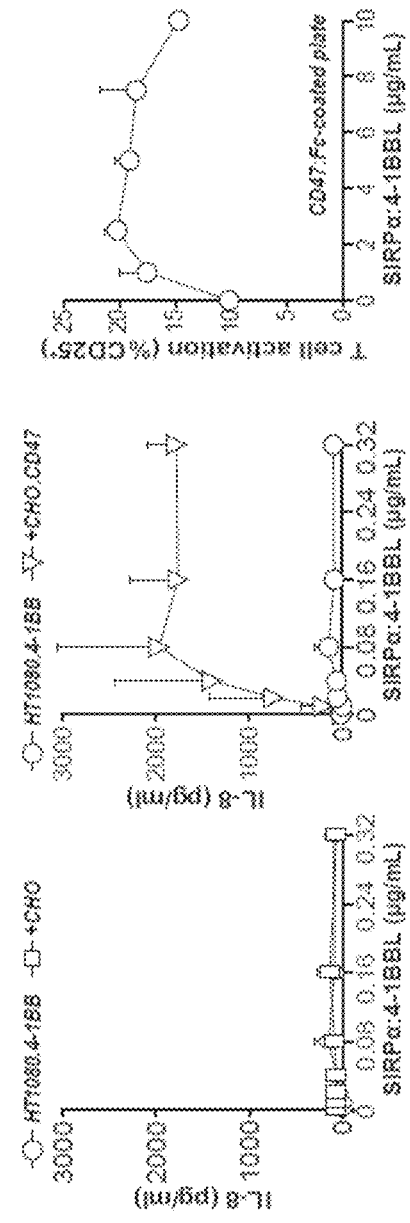
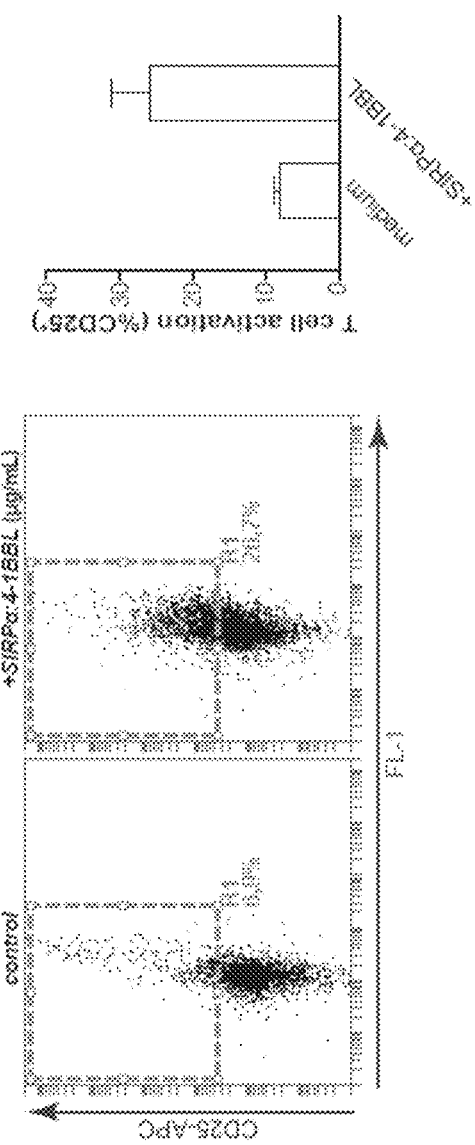

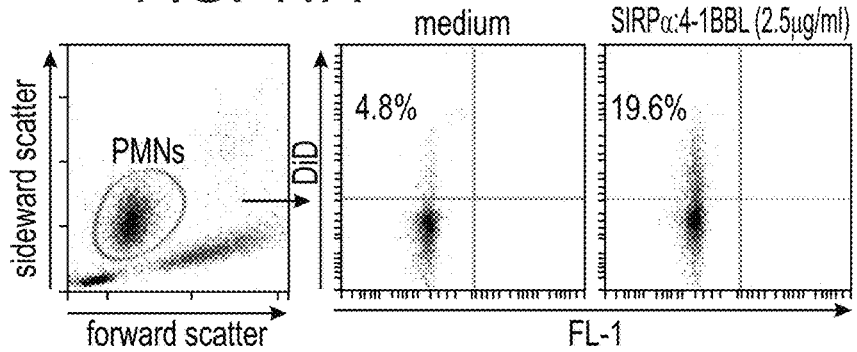
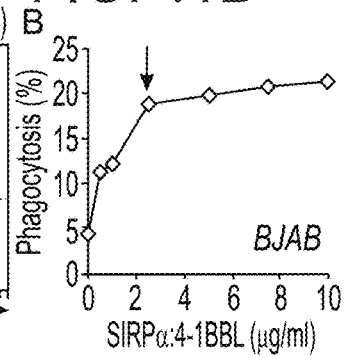
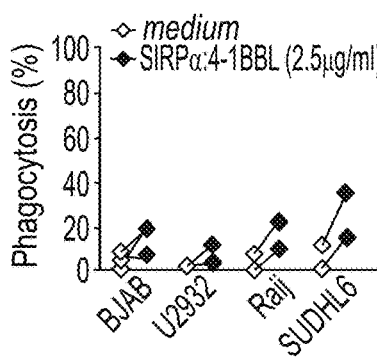
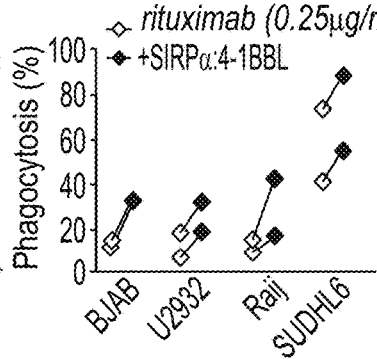
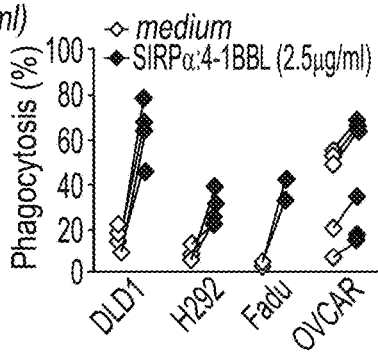
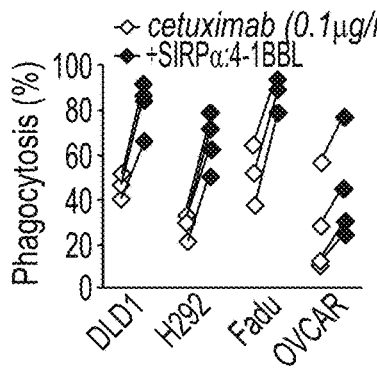
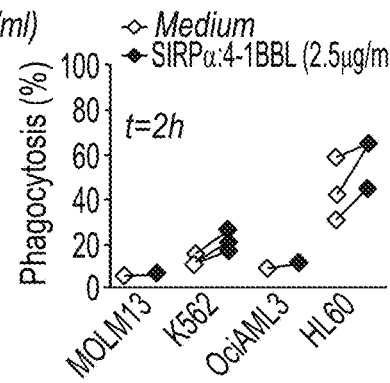
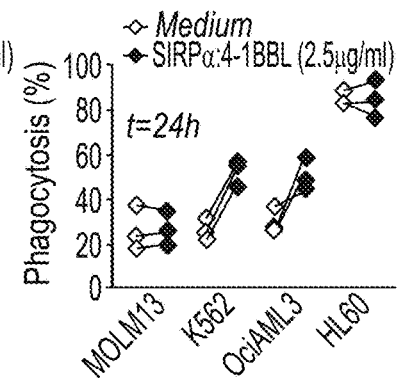
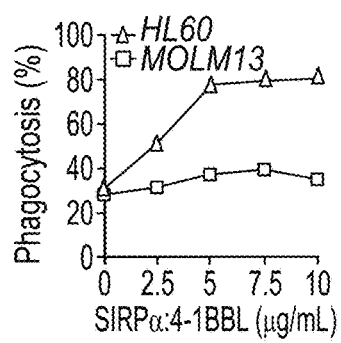
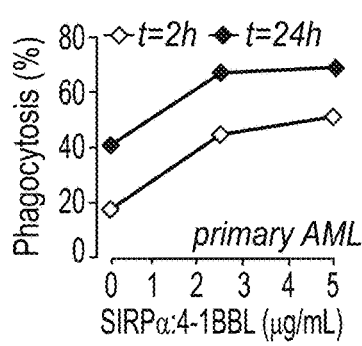
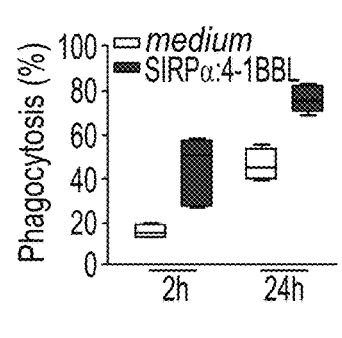

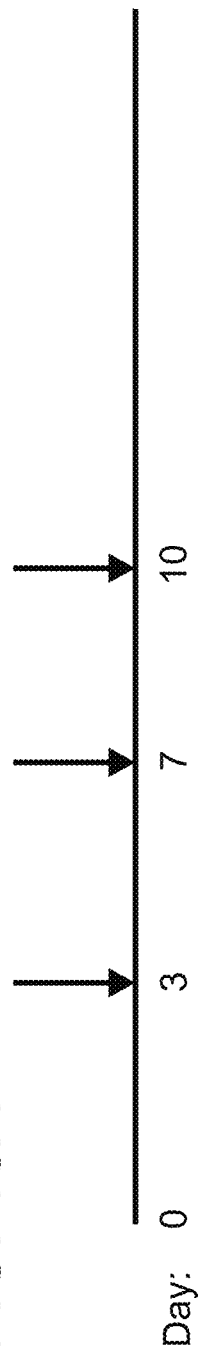
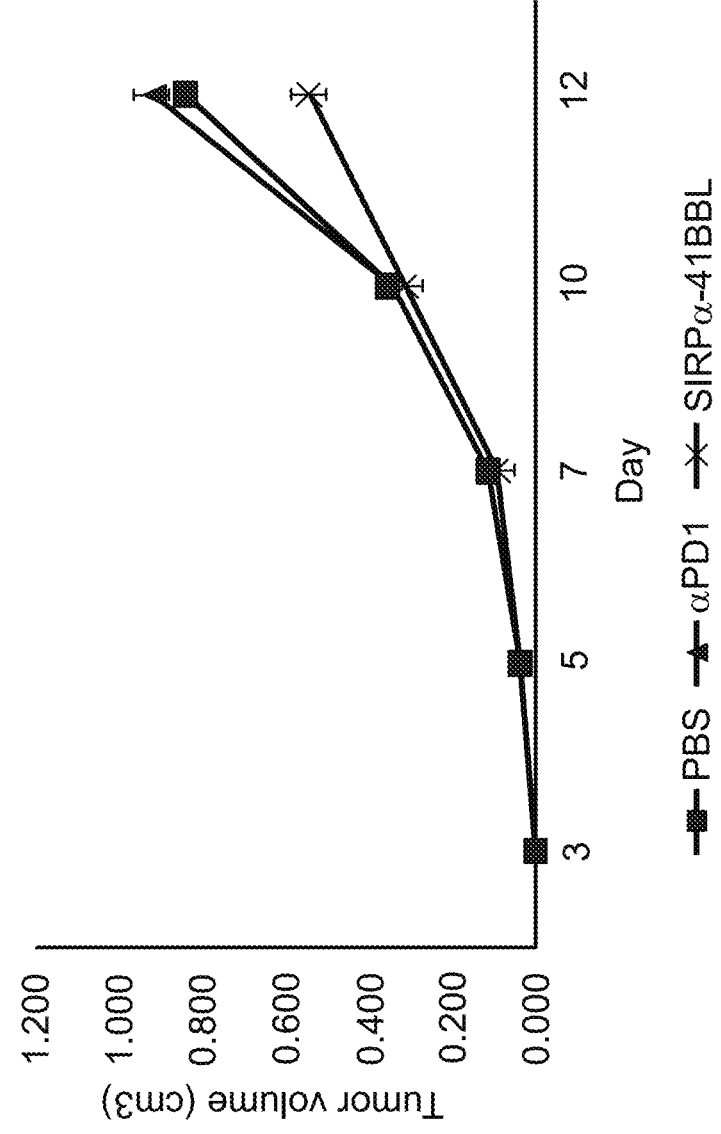
FIG. 13A
FIG. 13B

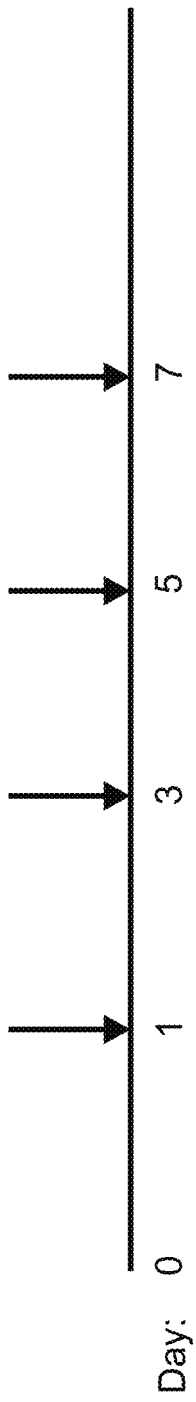
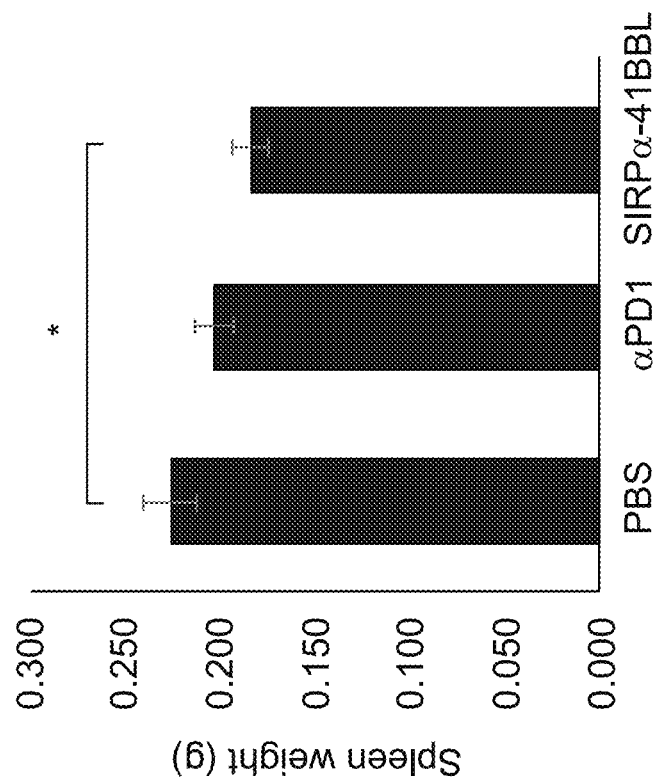
FIG. 14A
FIG. 14B

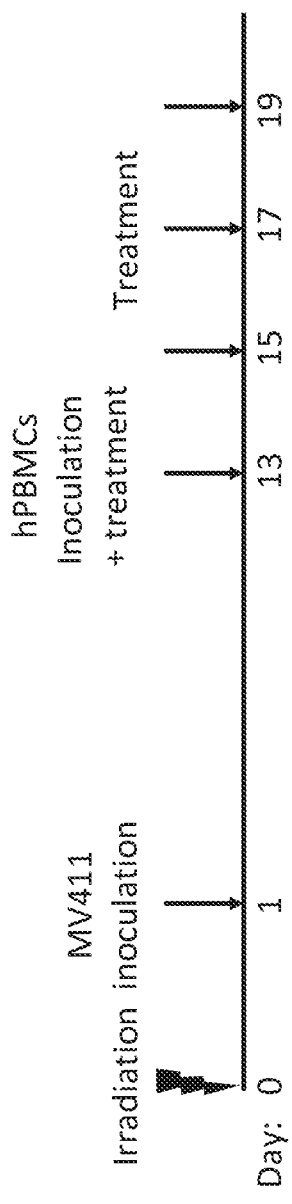
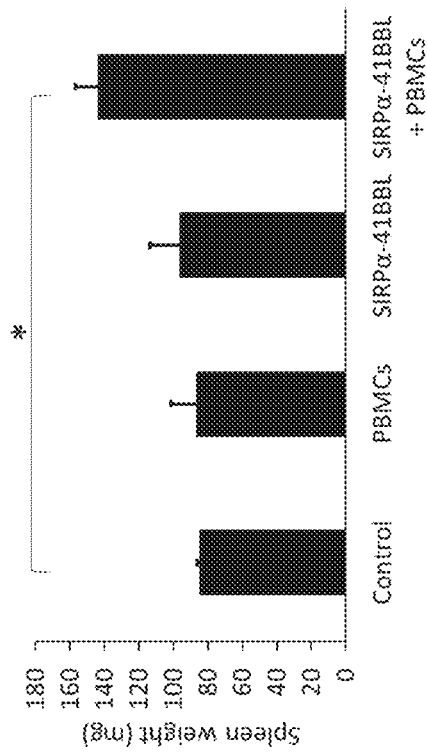
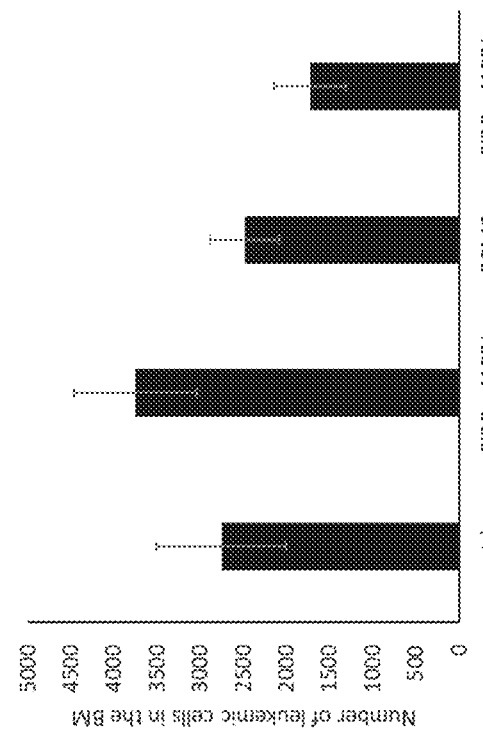
FIG. 15A
FIG. 15B
FIG. 15C

SEQUENCE LISTING

```
<160> NUMBER OF SEQ ID NOS: 15

<210> SEQ ID NO 1
<211> LENGTH: 549
<212> TYPE: PRT
<213> ORGANISM: Artificial sequence
<220> FEATURE:
<223> OTHER INFORMATION: Amino-acid sequence of the chimera protein
      (SIRP alpha-G-41BBL)

<400> SEQUENCE: 1

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
        275                 280                 285

Asn Val Ser Ala His Arg Asp Asp Val Lys Leu Thr Cys Gln Val Glu
    290                 295                 300
```

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
            325                 330                 335

Ser Asn Glu Arg Asn Ile Tyr Gly Ala Cys Pro Trp Ala Val Ser Gly
        340                 345                 350

Ala Arg Ala Ser Pro Gly Ser Ala Ala Ser Pro Arg Leu Arg Glu Gly
    355                 360                 365

Pro Glu Leu Ser Pro Asp Asp Pro Ala Gly Leu Leu Asp Leu Arg Gln
370                 375                 380

Gly Met Phe Ala Gln Leu Val Ala Gln Asn Val Leu Leu Ile Asp Gly
385                 390                 395                 400

Pro Leu Ser Trp Tyr Ser Asp Pro Gly Leu Ala Gly Val Ser Leu Thr
            405                 410                 415

Gly Gly Leu Ser Tyr Lys Glu Asp Thr Lys Glu Leu Val Val Ala Lys
        420                 425                 430

Ala Gly Val Tyr Tyr Val Phe Phe Gln Leu Glu Leu Arg Arg Val Val
    435                 440                 445

Ala Gly Glu Gly Ser Gly Ser Val Ser Leu Ala Leu His Leu Gln Pro
450                 455                 460

Leu Arg Ser Ala Ala Gly Ala Ala Ala Leu Ala Leu Thr Val Asp Leu
465                 470                 475                 480

Pro Pro Ala Ser Ser Glu Ala Arg Asn Ser Ala Phe Gly Phe Gln Gly
            485                 490                 495

Arg Leu Leu His Leu Ser Ala Gly Gln Arg Leu Gly Val His Leu His
        500                 505                 510

Thr Glu Ala Arg Ala Arg His Ala Trp Gln Leu Thr Gln Gly Ala Thr
    515                 520                 525

Val Leu Gly Leu Phe Arg Val Thr Pro Glu Ile Pro Ala Gly Leu Pro
530                 535                 540

Ser Pro Arg Ser Glu
545

<210> SEQ ID NO 2
<211> LENGTH: 343
<212> TYPE: PRT
<213> ORGANISM: homo sapiens

<400> SEQUENCE: 2

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala

```
            115                 120                 125
Arg Ala Thr Pro Gln His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
        275                 280                 285

Asn Val Ser Ala His Arg Asp Asp Val Lys Leu Thr Cys Gln Val Glu
    290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr
            340

<210> SEQ ID NO 3
<211> LENGTH: 205
<212> TYPE: PRT
<213> ORGANISM: homo sapiens

<400> SEQUENCE: 3

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
            20                  25                  30

Ala Gly Leu Leu Asp Leu Arg Gln Gly Met Phe Ala Gln Leu Val Ala
        35                  40                  45

Gln Asn Val Leu Leu Ile Asp Gly Pro Leu Ser Trp Tyr Ser Asp Pro
    50                  55                  60

Gly Leu Ala Gly Val Ser Leu Thr Gly Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
            100                 105                 110

Ser Leu Ala Leu His Leu Gln Pro Leu Arg Ser Ala Ala Gly Ala Ala
        115                 120                 125

Ala Leu Ala Leu Thr Val Asp Leu Pro Pro Ala Ser Ser Glu Ala Arg
    130                 135                 140
```

```
Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
                165                 170                 175

Trp Gln Leu Thr Gln Gly Ala Thr Val Leu Gly Leu Phe Arg Val Thr
            180                 185                 190

Pro Glu Ile Pro Ala Gly Leu Pro Ser Pro Arg Ser Glu
        195                 200                 205

<210> SEQ ID NO 4
<211> LENGTH: 548
<212> TYPE: PRT
<213> ORGANISM: Artificial sequence
<220> FEATURE:
<223> OTHER INFORMATION: Amino-acid sequence of the chimera protein
      (SIRPalpha- 41BBL, no linker)

<400> SEQUENCE: 4

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
        275                 280                 285

Asn Val Ser Ala His Arg Asp Asp Val Lys Leu Thr Cys Gln Val Glu
    290                 295                 300
```

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Ala Cys Pro Trp Ala Val Ser Gly Ala
            340                 345                 350

Arg Ala Ser Pro Gly Ser Ala Ala Ser Pro Arg Leu Arg Glu Gly Pro
        355                 360                 365

Glu Leu Ser Pro Asp Asp Pro Ala Gly Leu Leu Asp Leu Arg Gln Gly
    370                 375                 380

Met Phe Ala Gln Leu Val Ala Gln Asn Val Leu Leu Ile Asp Gly Pro
385                 390                 395                 400

Leu Ser Trp Tyr Ser Asp Pro Gly Leu Ala Gly Val Ser Leu Thr Gly
                405                 410                 415

Gly Leu Ser Tyr Lys Glu Asp Thr Lys Glu Leu Val Val Ala Lys Ala
            420                 425                 430

Gly Val Tyr Tyr Val Phe Phe Gln Leu Glu Leu Arg Arg Val Val Ala
        435                 440                 445

Gly Glu Gly Ser Gly Ser Val Ser Leu Ala Leu His Leu Gln Pro Leu
    450                 455                 460

Arg Ser Ala Ala Gly Ala Ala Ala Leu Ala Leu Thr Val Asp Leu Pro
465                 470                 475                 480

Pro Ala Ser Ser Glu Ala Arg Asn Ser Ala Phe Gly Phe Gln Gly Arg
                485                 490                 495

Leu Leu His Leu Ser Ala Gly Gln Arg Leu Gly Val His Leu His Thr
            500                 505                 510

Glu Ala Arg Ala Arg His Ala Trp Gln Leu Thr Gln Gly Ala Thr Val
        515                 520                 525

Leu Gly Leu Phe Arg Val Thr Pro Glu Ile Pro Ala Gly Leu Pro Ser
    530                 535                 540

Pro Arg Ser Glu
545

<210> SEQ ID NO 5
<211> LENGTH: 554
<212> TYPE: PRT
<213> ORGANISM: Artificial sequence
<220> FEATURE:
<223> OTHER INFORMATION: Amino-acid sequence of His-tagged SIRP alpha -
      41BBL

<400> SEQUENCE: 5

His His His His His His Glu Glu Glu Leu Gln Val Ile Gln Pro Asp
1               5                   10                  15

Lys Ser Val Leu Val Ala Ala Gly Glu Thr Ala Thr Leu Arg Cys Thr
                20                  25                  30

Ala Thr Ser Leu Ile Pro Val Gly Pro Ile Gln Trp Phe Arg Gly Ala
            35                  40                  45

Gly Pro Gly Arg Glu Leu Ile Tyr Asn Gln Lys Glu Gly His Phe Pro
        50                  55                  60

Arg Val Thr Thr Val Ser Asp Leu Thr Lys Arg Asn Asn Met Asp Phe
65                  70                  75                  80

Ser Ile Arg Ile Gly Asn Ile Thr Pro Ala Asp Ala Gly Thr Tyr Tyr
                85                  90                  95

Cys Val Lys Phe Arg Lys Gly Ser Pro Asp Asp Val Glu Phe Lys Ser

-continued

```
                100             105             110
Gly Ala Gly Thr Glu Leu Ser Val Arg Ala Lys Pro Ser Ala Pro Val
            115                 120                 125

Val Ser Gly Pro Ala Ala Arg Ala Thr Pro Gln His Thr Val Ser Phe
        130                 135                 140

Thr Cys Glu Ser His Gly Phe Ser Pro Arg Asp Ile Thr Leu Lys Trp
145                 150                 155                 160

Phe Lys Asn Gly Asn Glu Leu Ser Asp Phe Gln Thr Asn Val Asp Pro
                165                 170                 175

Val Gly Glu Ser Val Ser Tyr Ser Ile His Ser Thr Ala Lys Val Val
            180                 185                 190

Leu Thr Arg Glu Asp Val His Ser Gln Val Ile Cys Glu Val Ala His
        195                 200                 205

Val Thr Leu Gln Gly Asp Pro Leu Arg Gly Thr Ala Asn Leu Ser Glu
    210                 215                 220

Thr Ile Arg Val Pro Pro Thr Leu Glu Val Thr Gln Gln Pro Val Arg
225                 230                 235                 240

Ala Glu Asn Gln Val Asn Val Thr Cys Gln Val Arg Lys Phe Tyr Pro
                245                 250                 255

Gln Arg Leu Gln Leu Thr Trp Leu Glu Asn Gly Asn Val Ser Arg Thr
            260                 265                 270

Glu Thr Ala Ser Thr Val Thr Glu Asn Lys Asp Gly Thr Tyr Asn Trp
        275                 280                 285

Met Ser Trp Leu Leu Val Asn Val Ser Ala His Arg Asp Asp Val Lys
    290                 295                 300

Leu Thr Cys Gln Val Glu His Asp Gly Gln Pro Ala Val Ser Lys Ser
305                 310                 315                 320

His Asp Leu Lys Val Ser Ala His Pro Lys Glu Gln Gly Ser Asn Thr
                325                 330                 335

Ala Ala Glu Asn Thr Gly Ser Asn Glu Arg Asn Ile Tyr Gly Ala Cys
            340                 345                 350

Pro Trp Ala Val Ser Gly Ala Arg Ala Ser Pro Gly Ser Ala Ser Pro
        355                 360                 365

Arg Leu Arg Glu Gly Pro Glu Leu Ser Pro Asp Asp Pro Ala Gly Leu
    370                 375                 380

Leu Asp Leu Arg Gln Gly Met Phe Ala Gln Leu Val Ala Gln Asn Val
385                 390                 395                 400

Leu Leu Ile Asp Gly Pro Leu Ser Trp Tyr Ser Asp Pro Gly Leu Ala
                405                 410                 415

Gly Val Ser Leu Thr Gly Gly Leu Ser Tyr Lys Glu Asp Thr Lys Glu
            420                 425                 430

Leu Val Val Ala Lys Ala Gly Val Tyr Tyr Val Phe Phe Gln Leu Glu
        435                 440                 445

Leu Arg Arg Val Val Ala Gly Glu Gly Ser Gly Ser Val Ser Leu Ala
    450                 455                 460

Leu His Leu Gln Pro Leu Arg Ser Ala Ala Gly Ala Ala Ala Leu Ala
465                 470                 475                 480

Leu Thr Val Asp Leu Pro Pro Ala Ser Ser Glu Ala Arg Asn Ser Ala
                485                 490                 495

Phe Gly Phe Gln Gly Arg Leu Leu His Leu Ser Ala Gly Gln Arg Leu
            500                 505                 510

Gly Val His Leu His Thr Glu Ala Arg Ala Arg His Ala Trp Gln Leu
        515                 520                 525
```

```
Thr Gln Gly Ala Thr Val Leu Gly Leu Phe Arg Val Thr Pro Glu Ile
            530                 535                 540

Pro Ala Gly Leu Pro Ser Pro Arg Ser Glu
545                 550

<210> SEQ ID NO 6
<211> LENGTH: 312
<212> TYPE: PRT
<213> ORGANISM: Artificial sequence
<220> FEATURE:
<223> OTHER INFORMATION: Amino-acid sequence of PD1-CD70

<400> SEQUENCE: 6

His His His His His Pro Gly Trp Phe Leu Asp Ser Pro Asp Arg
1                5                  10                  15

Pro Trp Asn Pro Pro Thr Phe Ser Pro Ala Leu Leu Val Val Thr Glu
                20                  25                  30

Gly Asp Asn Ala Thr Phe Thr Cys Ser Phe Ser Asn Thr Ser Glu Ser
            35                  40                  45

Phe Val Leu Asn Trp Tyr Arg Met Ser Pro Ser Asn Gln Thr Asp Lys
    50                  55                  60

Leu Ala Ala Phe Pro Glu Asp Arg Ser Gln Pro Gly Gln Asp Cys Arg
65                  70                  75                  80

Phe Arg Val Thr Gln Leu Pro Asn Gly Arg Asp Phe His Met Ser Val
                85                  90                  95

Val Arg Ala Arg Arg Asn Asp Ser Gly Thr Tyr Leu Cys Gly Ala Ile
            100                 105                 110

Ser Leu Ala Pro Lys Ala Gln Ile Lys Glu Ser Leu Arg Ala Glu Leu
        115                 120                 125

Arg Val Thr Glu Arg Arg Ala Glu Val Pro Thr Ala His Pro Ser Pro
    130                 135                 140

Ser Pro Arg Pro Ala Gly Gln Phe Gln Thr Leu Val Gly Gln Arg Phe
145                 150                 155                 160

Ala Gln Ala Gln Gln Gln Leu Pro Leu Glu Ser Leu Gly Trp Asp Val
                165                 170                 175

Ala Glu Leu Gln Leu Asn His Thr Gly Pro Gln Gln Asp Pro Arg Leu
            180                 185                 190

Tyr Trp Gln Gly Gly Pro Ala Leu Gly Arg Ser Phe Leu His Gly Pro
        195                 200                 205

Glu Leu Asp Lys Gly Gln Leu Arg Ile His Arg Asp Gly Ile Tyr Met
    210                 215                 220

Val His Ile Gln Val Thr Leu Ala Ile Cys Ser Ser Thr Thr Ala Ser
225                 230                 235                 240

Arg His His Pro Thr Thr Leu Ala Val Gly Ile Cys Ser Pro Ala Ser
                245                 250                 255

Arg Ser Ile Ser Leu Leu Arg Leu Ser Phe His Gln Gly Cys Thr Ile
            260                 265                 270

Ala Ser Gln Arg Leu Thr Pro Leu Ala Arg Gly Asp Thr Leu Cys Thr
        275                 280                 285

Asn Leu Thr Gly Thr Leu Leu Pro Ser Arg Asn Thr Asp Glu Thr Phe
    290                 295                 300

Phe Gly Val Gln Trp Val Arg Pro
305                 310

<210> SEQ ID NO 7
```

<211> LENGTH: 1665
<212> TYPE: DNA
<213> ORGANISM: Artificial sequence
<220> FEATURE:
<223> OTHER INFORMATION: Nucleic-acid sequence of SIRP alpha-41BBL (with his tag)

<400> SEQUENCE: 7

| | | | | | |
|---|---|---|---|---|---|
| caccatcatc | accaccatga | agaggaactg | caagtgatcc | agcctgacaa | gagcgtgctg | 60 |
| gtggctgctg | gcgaaacagc | cacactgaga | tgtaccgcca | cctctctgat | ccctgtgggc | 120 |
| cctatccagt | ggtttagagg | cgctggacct | ggcagagagc | tgatctacaa | ccagaaagag | 180 |
| ggacacttcc | ccagagtgac | caccgtgtcc | gacctgacca | gcggaacaa | catggacttc | 240 |
| agcatccgga | tcggcaacat | cacccctgcc | gatgccggca | cctactactg | cgtgaagttc | 300 |
| agaaagggca | gccccgacga | cgtcgagttt | aaaagcggag | ccggcacaga | gctgagcgtg | 360 |
| cgggctaaac | cttctgctcc | tgtggtgtct | ggacctgccg | ctagagctac | acctcagcac | 420 |
| accgtgtctt | ttacctgcga | gagccacggc | ttcagcccca | gagatatcac | cctgaagtgg | 480 |
| ttcaagaacg | gcaacgagct | gtccgacttc | agaccaacg | tggaccctgt | gggagagagc | 540 |
| gtgtcctaca | gcatccacag | cacagccaag | gtggtgctga | cccgggaaga | tgtgcactcc | 600 |
| caagtgattt | gcgaggtggc | ccacgttacc | ctgcaaggcg | atcctctgag | aggcaccgcc | 660 |
| aatctgagcg | agacaatccg | ggtgccacct | acactggaag | tgacccagca | gcctgtgcgg | 720 |
| gccgagaatc | aagtgaacgt | gacctgccaa | gtgcggaagt | tctaccctca | gagactgcag | 780 |
| ctgacctggc | tggaaaacgg | caatgtgtcc | agaaccgaga | cagccagcac | cgtgaccgag | 840 |
| aacaaggatg | gcacctacaa | ttggatgagc | tggctgctcg | tgaatgtgtc | tgcccaccgg | 900 |
| gacgatgtga | agctgacatg | ccaggtggaa | cacgatggcc | agcctgccgt | gtctaagagc | 960 |
| cacgacctga | aggtgtccgc | tcatcccaaa | gagcagggct | ctaatactgc | cgccgagaac | 1020 |
| accggcagca | acgagagaaa | tatctacggc | gcttgtcctt | gggccgtttc | tggcgctaga | 1080 |
| gcctctcctg | gatctgccgc | ttctcccaga | ctgagagagg | gacctgagct | gagccctgat | 1140 |
| gatcctgctg | gactgctgga | tctgagacag | ggcatgtttg | cccagctggt | ggcccagaat | 1200 |
| gtgctgctga | ttgatggccc | tctgtcctgg | tacagcgatc | ctggacttgc | tggcgttagc | 1260 |
| ctgactggcg | gcctgagcta | caaagaggac | accaagaac | tggtggtggc | caaggccggc | 1320 |
| gtgtactacg | tgttctttca | gctggaactg | cggagagtgg | tggccggcga | aggatctgga | 1380 |
| tctgtgtctc | tggctctgca | tctgcagcct | ctgagatctg | ctgctggtgc | tgctgctctg | 1440 |
| gccctgacag | ttgatctgcc | tcctgcctct | agcgaggcca | gaaactccgc | ctttggcttc | 1500 |
| caaggcagac | tgctgcacct | gagcgctgga | cagagactgg | gagtccatct | gcacacagaa | 1560 |
| gccgagagcta | gacacgcctg | gcagctgaca | caaggcgcta | cagtgctggg | cctgttcaga | 1620 |
| gtgaccctg | agattccagc | cggcctgcca | tctcctagat | ctgag | | 1665 |

<210> SEQ ID NO 8
<211> LENGTH: 1647
<212> TYPE: DNA
<213> ORGANISM: Artificial sequence
<220> FEATURE:
<223> OTHER INFORMATION: Nucleic-acid sequence of SIRP alpha-41BBL

<400> SEQUENCE: 8

| | | | | | |
|---|---|---|---|---|---|
| gaagaggaac | tgcaagtgat | ccagcctgac | aagagcgtgc | tggtggctgc | tggcgaaaca | 60 |
| gccacactga | gatgtaccgc | cacctctctg | atccctgtgg | gccctatcca | gtggtttaga | 120 |

```
ggcgctggac ctggcagaga gctgatctac aaccagaaag agggacactt ccccagagtg    180
accaccgtgt ccgacctgac caagcggaac aacatggact tcagcatccg gatcggcaac    240
atcacccctg ccgatgccgg cacctactac tgcgtgaagt tcagaaaggg cagccccgac    300
gacgtcgagt ttaaaagcgg agccggcaca gagctgagcg tgcgggctaa accttctgct    360
cctgtggtgt ctggacctgc cgctagagct acacctcagc accgtgtc ttttacctgc      420
gagagccacg gcttcagccc cagagatatc accctgaagt ggttcaagaa cggcaacgag    480
ctgtccgact tccagaccaa cgtggaccct gtgggagaga gcgtgtccta cagcatccac    540
agcacagcca aggtggtgct gacccgggaa gatgtgcact cccaagtgat tgcgaggtg     600
gcccacgtta ccctgcaagg cgatcctctg agaggcaccg ccaatctgag cgagacaatc    660
cgggtgccac ctacactgga agtgacccag cagcctgtgc gggccgagaa tcaagtgaac    720
gtgacctgcc aagtgcggaa gttctaccct cagagactgc agctgacctg gctggaaaac    780
ggcaatgtgt ccagaaccga cagccagc accgtgaccg agaacaagga tggcacctac     840
aattggatga gctggctgct cgtgaatgtg tctgcccacc gggacgatgt gaagctgaca    900
tgccaggtgg aacacgatgg ccagcctgcc gtgtctaaga gccacgacct gaaggtgtcc    960
gctcatccca agagcagggg ctctaatact gccgccgaga caccggcag caacgagaga    1020
aatatctacg gcgcttgtcc ttgggccgtt tctggcgcta gagcctctcc tggatctgcc    1080
gcttctccca gactgagaga gggacctgag ctgagccctg atgatcctgc tggactgctg    1140
gatctgagac agggcatgtt tgcccagctg gtggcccaga atgtgctgct gattgatggc    1200
cctctgtcct ggtacagcga tcctggactt gctggcgtta gctgactgg cggcctgagc    1260
tacaaagagg acaccaaaga actggtggtg gccaaggccg gcgtgtacta cgtgttcttt    1320
cagctggaac tgcggagagt ggtggccggc gaaggatctg gatctgtgtc tctggctctg    1380
catctgcagc ctctgagatc tgctgctggt gctgctgctc tggccctgac agttgatctg    1440
cctcctgcct ctagcgaggc cagaaactcc gcctttggct tccaaggcag actgctgcac    1500
ctgagcgctg acagagact gggagtccat ctgcacacag aagccagagc tagacacgcc    1560
tggcagctga cacaaggcgc tacagtgctg ggcctgttca gagtgacccc tgagattcca    1620
gccggcctgc catctcctag atctgag                                        1647
```

<210> SEQ ID NO 9
<211> LENGTH: 504
<212> TYPE: PRT
<213> ORGANISM: Artificial sequence
<220> FEATURE:
<223> OTHER INFORMATION: Amino-acid sequence of full length SIRP alpha

<400> SEQUENCE: 9

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

```
Thr Lys Arg Asn Asn Met Asp Phe Ser Ile Arg Ile Gly Asn Ile Thr
                100                 105                 110

Pro Ala Asp Ala Gly Thr Tyr Tyr Cys Val Lys Phe Arg Lys Gly Ser
            115                 120                 125

Pro Asp Asp Val Glu Phe Lys Ser Gly Ala Gly Thr Glu Leu Ser Val
130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
    370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
        435                 440                 445

Asn His Thr Glu Tyr Ala Ser Ile Gln Thr Ser Pro Gln Pro Ala Ser
    450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
            500
```

<210> SEQ ID NO 10
<211> LENGTH: 1512
<212> TYPE: DNA
<213> ORGANISM: Artificial sequence
<220> FEATURE:
<223> OTHER INFORMATION: Nucleic-acid sequence of full length SIRP alpha

<400> SEQUENCE: 10

| | | |
|---|---|---|
| atggagcccg ccggcccggc ccccggccgc ctcgggccgc tgctctgcct gctgctcgcc | 60 |
| gcgtcctgcg cctggtcagg agtggcgggt gaggaggagc tgcaggtgat tcagcctgac | 120 |
| aagtccgtat cagttgcagc tggagagtcg gccattctgc actgcactgt gacctccctg | 180 |
| atccctgtgg ggcccatcca gtggttcaga ggagctggac cagcccggga attaatctac | 240 |
| aatcaaaaag aaggccactt cccccgggta caactgtttt cagagtccac aaagagagaa | 300 |
| aacatggact tttccatcag catcagtaac atcaccccag cagatgccgg cacctactac | 360 |
| tgtgtgaagt tccggaaagg agccctgac acggagttta agtctggagc aggcactgag | 420 |
| ctgtctgtgc gtgccaaacc ctctgccccc gtggtatcgg ccctgcggc gagggccaca | 480 |
| cctcagcaca cagtgagctt cacctgcgag tcccacggct ctcacccag agacatcacc | 540 |
| ctgaaatggt tcaaaaatgg gaatgagctc tcagacttcc agaccaacgt ggaccccgta | 600 |
| ggagagagcg tgtcctacag catccacagc acagccaagg tggtgctgac ccgcgaggac | 660 |
| gttcactctc aagtcatctg cgaggtggcc cacgtcacct gcaggggga ccctcttcgt | 720 |
| gggactgcca acttgtctga gaccatccga gttccaccca ccttggaggt tactcaacag | 780 |
| cccgtgaggg cagagaacca ggtgaatgtc acctgccagg tgaggaagtt ctaccccag | 840 |
| agactacagc tgacctggtt ggagaatgga aacgtgtccc ggacagaaac ggcctcaacc | 900 |
| gttacagaga caaggatgg tacctacaac tggatgagct ggctcctggt gaatgtatct | 960 |
| gcccacaggg atgatgtgaa gctcacctgc caggtggagc atgacgggca gccagcggtc | 1020 |
| agcaaaagcc atgacctgaa ggtctcagcc caccccgaagg agcagggctc aaataccgcc | 1080 |
| gctgagaaca ctggatctaa tgaacggaac atctatattg tggtgggtgt ggtgtgcacc | 1140 |
| ttgctggtgg ccctactgat ggcggccctc tacctcgtcc gaatcagaca aagaaaagcc | 1200 |
| cagggctcca cttcttctac aaggttgcat gagcccgaga agaatgccag agaaataaca | 1260 |
| caggacacaa atgatatcac atatgcagac ctgaacctgc caagggggaa gaagcctgct | 1320 |
| ccccaggctg cggagcccaa caaccacacg gagtatgcca gcattcagac cagcccgcag | 1380 |
| cccgcgtcgg aggacaccct cacctatgct gacctggaca tggtccacct caaccggacc | 1440 |
| cccaagcagc cggcccccaa gcctgagccg tccttctcag agtacgccag cgtccaggtc | 1500 |
| ccgaggaagt ga | 1512 |

<210> SEQ ID NO 11
<211> LENGTH: 1029
<212> TYPE: DNA
<213> ORGANISM: Artificial sequence
<220> FEATURE:
<223> OTHER INFORMATION: Nucleic-acid sequence encoding the
       extracellular domain of the human SIRP alpha protein

<400> SEQUENCE: 11

| | | |
|---|---|---|
| gaggaggagc tgcaggtgat tcagcctgac aagtccgtat cagttgcagc tggagagtcg | 60 |
| gccattctgc actgcactgt gacctccctg atccctgtgg ggcccatcca gtggttcaga | 120 |
| ggagctggac cagcccggga attaatctac aatcaaaaag aaggccactt cccccgggta | 180 |

| | |
|---|---|
| acaactgttt cagagtccac aaagagagaa aacatggact tttccatcag catcagtaac | 240 |
| atcaccccag cagatgccgg cacctactac tgtgtgaagt tccggaaagg gagccctgac | 300 |
| acggagttta agtctggagc aggcactgag ctgtctgtgc gtgccaaacc ctctgccccc | 360 |
| gtggtatcgg gccctgcggc gagggccaca cctcagcaca cagtgagctt cacctgcgag | 420 |
| tcccacggct tctcacccag agacatcacc ctgaaatggt tcaaaaatgg gaatgagctc | 480 |
| tcagacttcc agaccaacgt ggaccccgta ggagagagcg tgtcctacag catccacagc | 540 |
| acagccaagg tggtgctgac ccgcgaggac gttcactctc aagtcatctg cgaggtggcc | 600 |
| cacgtcacct gcaggggga ccctcttcgt gggactgcca acttgtctga gaccatccga | 660 |
| gttccaccca ccttggaggt tactcaacag cccgtgaggg cagagaacca ggtgaatgtc | 720 |
| acctgccagg tgaggaagtt ctaccccag agactacagc tgacctggtt ggagaatgga | 780 |
| aacgtgtccc ggacagaaac ggcctcaacc gttacagaga caaggatgg tacctacaac | 840 |
| tggatgagct ggctcctggt gaatgtatct gcccacaggg atgatgtgaa gctccacctgc | 900 |
| caggtggagc atgacgggca gccagcggtc agcaaaagcc atgacctgaa ggtctcagcc | 960 |
| cacccgaagg agcagggctc aaataccgcc gctgagaaca ctggatctaa tgaacggaac | 1020 |
| atctatatt | 1029 |

<210> SEQ ID NO 12
<211> LENGTH: 254
<212> TYPE: PRT
<213> ORGANISM: Artificial sequence
<220> FEATURE:
<223> OTHER INFORMATION: Amino-acid sequence of full length 41BBL

<400> SEQUENCE: 12

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Ala Ala Ala Cys Ala Val Phe
            35                  40                  45

Leu Ala Cys Pro Trp Ala Val Ser Gly Ala Arg Ala Ser Pro Gly Ser
        50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
                100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
        130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205
```

```
Gly Gln Arg Leu Gly Val His Leu His Thr Glu Ala Arg Ala Arg His
    210                 215                 220
Ala Trp Gln Leu Thr Gln Gly Ala Thr Val Leu Gly Leu Phe Arg Val
225                 230                 235                 240
Thr Pro Glu Ile Pro Ala Gly Leu Pro Ser Pro Arg Ser Glu
                245                 250
```

```
<210> SEQ ID NO 13
<211> LENGTH: 765
<212> TYPE: DNA
<213> ORGANISM: Artificial sequence
<220> FEATURE:
<223> OTHER INFORMATION: Nucleic-acid sequence of full length 41BBL

<400> SEQUENCE: 13
atggaatacg cctctgacgc ttcactggac cccgaagccc cgtggcctcc cgcgccccgc    60
gctcgcgcct gccgcgtact gccttgggcc ctggtcgcgg ggctgctgct gctgctgctg   120
ctcgctgccg cctgcgccgt cttcctcgcc tgccccctgg gccgtgtccgg ggctcgcgcc   180 tcgcccggct ccgcggccag cccgagactc cgcgagggtc ccgagctttc gcccgacgat   240
cccgccggcc tcttggacct gcggcagggc atgtttgcgc agctggtggc caaaatgtt   300 ctgctgatcg atgggcccct gagctggtac agtgacccag gcctggcagg cgtgtccctg   360
acggggggcc tgagctacaa agaggacacg aaggagctgg tggtggccaa ggctggagtc   420
tactatgtct tctttcaact agagctgcgg cgcgtggtgg ccggcgaggg ctcaggctcc   480
gtttcacttg cgctgcacct gcagccactg cgctctgctg ctggggccgc cgccctggct   540
ttgaccgtgg acctgccacc cgcctcctcc gaggctcgga actcggcctt cggtttccag   600
ggccgcttgc tgcacctgag tgccggccag cgcctgggcg tccatcttca cactgaggcc   660
agggcacgcc atgcctggca gcttacccag ggcgccacag tcttgggact cttccgggtg   720 accccgaaa tcccagccgg actcccttca ccgaggtcgg aataa                    765
```

```
<210> SEQ ID NO 14
<211> LENGTH: 615
<212> TYPE: DNA
<213> ORGANISM: Artificial sequence
<220> FEATURE:
<223> OTHER INFORMATION: Nucleic-acid sequence encoding the
      extracellular domain of the human 41BBL

<400> SEQUENCE: 14
gcctgcccct gggccgtgtc cggggctcgc gcctcgcccg gctccgcggc cagcccgaga    60
ctccgcgagg gtcccgagct ttcgcccgac gatcccgccg gcctcttgga cctgcggcag   120
ggcatgtttg cgcagctggt ggcccaaaat gttctgctga tcgatgggcc cctgagctgg   180
tacagtgacc caggcctggc aggcgtgtcc ctgacggggg gcctgagcta caaagaggac   240
acgaaggagc tggtggtggc caaggctgga gtctactatg tcttctttca actagagctg   300
cggcgcgtgg tggccggcga gggctcaggc tccgtttcac ttgcgctgca cctgcagcca   360
ctgcgctctg ctgctggggc cgccgccctg gctttgaccg tggacctgcc accgcctcc   420 tccgaggctc ggaactcggc cttcggtttc cagggccgct tgctgcacct gagtgccggc   480
cagcgcctgg gcgtccatct tcacactgag gccagggcac gccatgcctg gcagcttacc   540
cagggcgcca cagtcttggg actcttccgg gtgaccccg aaatcccagc cggactccct   600
tcaccgaggt cggaa                                                    615
```

<210> SEQ ID NO 15
<211> LENGTH: 1749
<212> TYPE: DNA
<213> ORGANISM: Artificial sequence
<220> FEATURE:
<223> OTHER INFORMATION: cloning sequence of His-tagged SIRP
alpha -41BBL in the vector

<400> SEQUENCE: 15

```
gaattcccgc cgccaccatg ggctggtcct gcatcattct gtttctggtg gccacagcca      60
ccggcgtgca ctctcaccat catcaccacc atgaagagga actgcaagtg atccagcctg     120
acaagagcgt gctggtggct gctggcgaaa cagccacact gagatgtacc gccacctctc     180
tgatccctgt gggccctatc cagtggttta gaggcgctgg acctggcaga gagctgatct     240
acaaccagaa agagggacac ttccccagag tgaccaccgt gtccgacctg accaagcgga     300
acaacatgga cttcagcatc cggatcggca acatcacccc tgccgatgcc ggcacctact     360
actgcgtgaa gttcagaaag ggcagccccg acgacgtcga gtttaaaagc ggagccggca     420
cagagctgag cgtgcgggct aaaccttctg ctcctgtggt gtctggacct gccgctagag     480
ctacacctca gcacaccgtg tcttttacct gcgagagcca cggcttcagc cccagagata     540
tcaccctgaa gtggttcaag aacggcaacg agctgtccga cttccagacc aacgtggacc     600
ctgtgggaga gagcgtgtcc tacagcatcc acagcacagc caaggtggtg ctgacccggg     660
aagatgtgca ctcccaagtg atttgcgagg tggcccacgt taccctgcaa ggcgatcctc     720
tgagaggcac cgccaatctg agcgagacaa tccgggtgcc acctacactg gaagtgaccc     780
agcagcctgt gcgggccgag aatcaagtga cgtgacctg ccaagtgcgg aagttctacc     840
ctcagagact gcagctgacc tggctggaaa acggcaatgt gtccagaacc gagacagcca     900
gcaccgtgac cgagaacaag gatggcacct acaattggat gagctggctg ctcgtgaatg     960
tgtctgccca ccgggacgat gtgaagctga catgccaggt ggaacacgat ggccagcctg    1020
ccgtgtctaa gagccacgac ctgaaggtgt ccgctcatcc caaagagcag ggctctaata    1080
ctgccgccga gaacaccggc agcaacgaga gaaatatcta cggcgcttgt ccttgggccg    1140
tttctggcgc tagagcctct cctggatctg ccgcttctcc cagactgaga gagggacctg    1200
agctgagccc tgatgatcct gctggactgc tggatctgag acagggcatg tttgcccagc    1260
tggtggccca gaatgctgct gctgattgatg gccctctgtc ctggtacagc gatcctggac    1320
ttgctggcgt tagcctgact ggcggcctga gctacaaaga ggacaccaaa gaactggtgg    1380
tggccaaggc cggcgtgtac tacgtgttct ttcagctgga actgcggaga gtggtggccg    1440
gcgaaggatc tggatctgtg tctctggctc tgcatctgca gcctctgaga tctgctgctg    1500
gtgctgctgc tctggccctg acagttgatc tgcctcctgc ctctagcgag gccagaaact    1560
ccgcctttgg cttccaaggc agactgctgc acctgagcgc tggacagaga ctgggagtcc    1620
atctgcacac agaagccaga gctagacacg cctggcagct gacacaaggc gctacagtgc    1680
tgggcctgtt cagagtgacc cctgagattc agccggcct gccatctcct agatctgagt    1740
gataagctt                                                            1749
```

SIRPALPHA-41BBL FUSION PROTEIN AND METHODS OF USE THEREOF

RELATED APPLICATIONS

This application is a National Phase of PCT Patent Application No. PCT/IL2018/050017 having International filing date of Jan. 4, 2018, which claims the benefit of priority under 35 USC § 119(e) of U.S. Provisional Patent Application No. 62/442,469, filed on Jan. 5, 2017. The contents of the above applications are all incorporated by reference as if fully set forth herein in their entirety.

SEQUENCE LISTING STATEMENT

The ASCII file, entitled 77773SequenceListing.txt, created on Jun. 26, 2019, comprising 42,324 bytes, submitted concurrently with the filing of this application is incorporated herein by reference. The sequence listing submitted herewith is identical to the sequence listing forming part of the international application.

BACKGROUND OF THE INVENTION

Dual Signaling Proteins (DSP), also known as Signal-Converting-Proteins (SCP), which are currently known in the art as bi-functional fusion proteins that link an extracellular portion of a type I membrane protein (extracellular amino-terminus), to an extracellular portion of a type II membrane protein (extracellular carboxyl-terminus), forming a fusion protein with two active sides (see, for example, U.S. Pat. Nos. 7,569,663 and 8,039,437, both of which are hereby incorporated by reference as if fully set forth herein).

SIRPα (signal-regulatory protein alpha) is a cell surface receptor of the immunoglobulin superfamily. SIRPα is expressed mainly on the surface of immune cells from the phagocyte lineage like macrophages and dendritic cells (DC). CD47 is the ligand of SIRPα. CD47 is a cell surface molecule in the immunoglobulin superfamily. CD47 functions as an inhibitor of phagocytosis through ligation of SIRPα expressed on phagocytes. CD47 is widely expressed on a majority of normal tissues. In this way, CD47 serves as a "don't eat me signal" and a marker of self, as loss of CD47 leads to homeostatic phagocytosis of aged or damaged cells. CD47 has been found to be expressed on multiple human tumor types. Tumors evade macrophage phagocytosis through the expression of antiphagocytic signals, including CD47. While CD47 is ubiquitously expressed at low levels on normal cells, multiple tumors express increased levels of CD47 compared to their normal cell counterparts and overexpression of CD47 enabled tumors to escape innate immune system surveillance through evasion of phagocytosis. 4-1BBL is the activating ligand of the 41BB receptor (CD137), a member of the TNF receptor superfamily and a potent activation-induced T cell costimulatory molecule. 41BBL naturally forms a homo-trimer but signaling via 4-1BB requires significant oligomerization of 4-1BBL. 4-1BBL is present on a variety of antigen presenting cells (APCs), including dendritic cells (DCs), B cells, and macrophages. The 4-1BB receptor is not detected (<3%) on resting T cells or T cell lines, however, 4-1BB is stably upregulated when T cells are activated. 4-1BB activation upregulates survival genes, enhances cell division, induces cytokine production and prevents activation induced cell death in T-cells.

Additional background art includes:
International Patent Application Publication No. WO2017059168;
International Patent Application Publication No. WO2001/049318;
International Patent Application Publication No. WO2016/139668;
International Patent Application Publication No. WO2014/106839;
International Patent Application Publication No. WO2012/042480;
US Patent Application Publication No. 20150183881;
US Patent Application Publication No. US20070110746;
US Patent Application Publication No. US20070036783; and
U.S. Pat. No. 9,562,087.

SUMMARY OF THE INVENTION

According to an aspect of some embodiments of the present invention there is provided a SIRPα-41BBL fusion protein comprising a single amino acid linker between the SIRPα and the 41BBL.

According to an aspect of some embodiments of the present invention there is provided a SIRPα-41BBL fusion protein in a form of at least a homo-trimer.

According to some embodiments of the invention, the at least homo-trimer is at least 140 kD in molecular weight as determined by SDS-PAGE.

According to some embodiments of the invention, the SIRPα-41BBL fusion protein comprises a linker between the SIRPα and the 41BBL.

According to some embodiments of the invention, the linker has a length of one to six amino acids.

According to some embodiments of the invention, the linker is a single amino acid linker.

According to some embodiments of the invention, the linker is not an Fc domain of an antibody or a fragment thereof.

According to some embodiments of the invention, the linker is glycine.

According to some embodiments of the invention, the SIRPα-41BBL fusion protein being soluble.

According to some embodiments of the invention, the SIRPα comprises an extracellular domain of the SIRPα or a functional fragment thereof.

According to some embodiments of the invention, the 41BBL comprises an extracellular domain of the 41BBL or a functional fragment thereof.

According to some embodiments of the invention, the fusion protein is capable of at least one of:
(i) binding CD47 and 41BB;
(ii) activating the 41BB signaling pathway in a cell expressing the 41BB;
(iii) co-stimulating immune cells expressing the 41BB; and/or
(iv) enhancing phagocytosis of pathologic cells expressing the CD47 by phagocytes compared to same in the absence of the SIRPα-41BBL fusion protein.

According to some embodiments of the invention, the SIRPα-41BBL fusion protein amino acid sequence comprises SEQ ID NO: 1.

According to some embodiments of the invention, the SIRPα-41BBL fusion protein amino acid sequence consists of SEQ ID NO: 1.

According to some embodiments of the invention, there is provided a polynucleotide encoding the SIRPα-41BBL fusion protein of the present invention.

According to some embodiments of the invention, there is provided a nucleic acid construct comprising the polynucleotide of the present invention, and a regulatory element for directing expression of the polynucleotide in a host cell.

According to some embodiments of the invention, the polynucleotide comprises SEQ ID NO: 8.

According to some embodiments of the invention, there is provided a host cell comprising the SIRPα-41BBL fusion protein of the present invention or the polynucleotide or the nucleic acid construct of the present invention.

According to some embodiments of the invention, there is provided a method of producing a SIRPα-41BBL fusion protein, the method comprising expressing in a host cell the polynucleotide or the nucleic acid construct of the present invention.

According to some embodiments of the invention, the method comprising isolating the fusion protein.

According to some embodiments of the invention, the cell is selected from the group consisting of CHO, PERC.6 and 293.

According to some embodiments of the invention, there is provided a method of treating cancer comprising administering the SIRPα-41BBL fusion protein of the present invention to a subject in need thereof.

According to some embodiments of the invention, there is provided a method of treating a disease that can benefit from activating immune cells comprising administering to a subject in need thereof the SIRPα-41BBL fusion protein of the present invention, the polynucleotide or the nucleic acid construct of the present invention or the host cell of any one of the present invention.

According to an aspect of some embodiments of the present invention there is provided an article of manufacture identified for the treatment of a disease that can benefit from activating immune cells comprising a packaging material packaging a therapeutic agent for treating the disease; and a SIRPα-41BBL fusion protein, a polynucleotide encoding same, a nucleic acid construct encoding same or a host cell expressing same.

According to some embodiments of the invention, the disease comprises a hyper-proliferative disease.

According to some embodiments of the invention, the hyper-proliferative disease comprises sclerosis or fibrosis, Idiopathic pulmonary fibrosis, psoriasis, systemic sclerosis/scleroderma, primary biliary cholangitis, primary sclerosing cholangitis, liver fibrosis, prevention of radiation-induced pulmonary fibrosis, myelofibrosis or retroperitoneal fibrosis.

According to some embodiments of the invention, the hyper-proliferative disease comprises cancer.

According to an aspect of some embodiments of the present invention there is provided a method of treating cancer comprising administering to a subject in need thereof an anti-cancer agent; and a SIRPα-41BBL fusion protein, a polynucleotide encoding same, a nucleic acid construct encoding same or a host cell expressing same.

According to some embodiments of the invention, the cancer is selected from the group consisting of lymphoma, leukemia, colon cancer, pancreatic cancer, ovarian cancer, lung cancer and squamous cell carcinoma.

According to some embodiments of the invention, the cells of the cancer express CD47.

According to some embodiments of the invention, the disease comprises a disease associated with immune suppression or medication induced immunosuppression.

According to some embodiments of the invention, the disease comprises HIV, Measles, influenza, LCCM, RSV, Human Rhinoviruses, EBV, CMV or Parvo viruses.

According to some embodiments of the invention, the disease comprises an infection.

According to some embodiments of the invention, diseased cells of the subject express CD47.

According to an aspect of some embodiments of the present invention there is provided a method of activating T cells, the method comprising in-vitro activating T cells in the presence of a SIRPα-41BBL fusion protein and cells expressing CD47.

According to an aspect of some embodiments of the present invention there is provided a method of activating phagocytes, the method comprising in-vitro activating phagocytes in the presence of a SIRPα-41BBL fusion protein and cells expressing CD47.

According to an aspect of some embodiments of the present invention there is provided a method of activating immune cells, the method comprising in-vitro activating immune cells in the presence of a SIRPα-41BBL fusion protein, a polynucleotide encoding same, a nucleic acid construct encoding same or a host cell expressing same.

According to some embodiments of the invention, the activating is in the presence of cells expressing CD47 or exogenous CD47.

According to some embodiments of the invention, the cells expressing the CD47 comprise pathologic cells.

According to some embodiments of the invention, the pathologic cells comprise cancer cells.

According to some embodiments of the invention, the cancer is selected from the group consisting of lymphoma, carcinoma and leukemia.

According to some embodiments of the invention, the activating is in the presence of an anti-cancer agent.

According to some embodiments of the invention, the anti-cancer agent comprises an antibody.

According to some embodiments of the invention, the antibody is selected from the group consisting of rituximab, cetuximab, trastuzumab, edrecolomab, almetuzumab, gemtuzumab, ibritumomab, panitumumab, Belimumab, Bevacizumab, Bivatuzumab mertansine, Blinatumomab, Blontuvetmab, Brentuximab vedotin, Catumaxomab, Cixutumumab, Daclizumab, Adalimumab, Bezlotoxumab, Certolizumab pegol, Citatuzumab bogatox, Daratumumab, Dinutuximab, Elotuzumab, Ertumaxomab, Etaracizumab, Gemtuzumab ozogamicin, Girentuximab, Necitumumab, Obinutuzumab, Ofatumumab, Pertuzumab, Ramucirumab, Siltuximab, Tositumomab, Trastuzumab and ipilimumab.

According to some embodiments of the invention, the antibody is selected from the group consisting of rituximab, cetuximab and alemtuzumab.

According to some embodiments of the invention, the method comprising adoptively transferring the immune cells following the activating to a subject in need thereof.

According to some embodiments of the invention, the subject is afflicted with a disease associated with the cells expressing the CD47.

According to some embodiments of the invention, the SIRPα-41BBL fusion protein comprises the SIRPα-41BBL fusion protein of the present invention, the polynucleotide or the nucleic acid construct comprises the polynucleotide or the nucleic acid construct of the present invention, and the host cell comprises the host cell of the present invention.

According to some embodiments of the invention, the immune cells comprise T cells.

According to some embodiments of the invention, the immune cells comprise phagocytes.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a photograph of western blot analysis of His-tagged SIRPα-41BBL (SEQ ID NO: 5) under reducing or non-reducing conditions. Following affinity purification, proteins (250 ng/well) were separated on SDS-PAGE gel under denaturing or non denaturing conditions, as indicated, followed by immunoblotting with an anti-His-tag antibody.

FIGS. 2A-B are photographs of western blot analysis of His-tagged SIRPα-41BBL (SEQ ID NO: 5) under reducing or non-reducing conditions. Following affinity purification, proteins (250 ng/well) were separated on SDS-PAGE gel under denaturing (FIG. 2A) or non-denaturing (FIG. 2B) conditions, followed by immunoblotting with an anti-41BBL antibody.

FIG. 2C is a photograph of coomassie blue staining of SDS-PAGE analysis of His-tagged SIRPα-41BBL (SEQ ID NO: 5) under reducing conditions treated or un-treated with de-glycosylase. His-tagged SIRPα-41BBL bands are marked with small black arrows.

FIGS. 3A-B are graphs demonstrating interaction of His-tagged SIRPα-41BBL (SEQ ID NO: 5) with its counterpart ligands, as determined by bio-layer interferometry Blitz® assay.

FIG. 3A demonstrates binding to CD47—the biosensor was pre-loaded with CD47:Fc and then incubated with His-tagged SIRPα-41BBL (SEQ ID NO: 5) or PD1-CD70 (SEQ ID NO: 6, as a negative control). FIG. 3B demonstrates binding to 41BB—the biosensor was pre-loaded with 41BB:Fc and then incubated with His-tagged SIRPα-41BBL (SEQ ID NO: 5) or PD1-CD70 (SEQ ID NO: 6, as a negative control).

FIGS. 4A-B are histograms demonstrating expression patterns of the indicated receptors on CHO-K1-WT cells (FIG. 4A) and CHO-KI-CD47 cells (FIG. 4B). The surface expression levels of 41BB and CD47 was determined by immuno-staining of each cell line with the corresponding antibodies, followed by flow cytometric analysis.

FIGS. 5A-B demonstrate binding of His-tagged SIRPα-41BBL protein (SEQ ID NO: 5) to CHO-K1-47 cells (FIG. 5A) but not to CHO-K1-WT cells (FIG. 5B). The cells were incubated with different concentrations of His-tagged SIRPα-41BBL protein (SEQ ID NO: 5) for 30 minutes, followed by immune-staining with anti-41BBL antibody and flow cytometry analysis. GMFI values were used to create a binding curve graph with a GraphPad Prism software.

FIGS. 8A-E demonstrate that His-tagged SIRPα-41BBL protein (SEQ ID NO: 5) triggers 41BB co-stimulatory signaling and potentiates T cell activation. FIG. 8A is a graph demonstrating IL-8 concentration in supernatant of HT1080-41BB cell cultures and co-cultures of HT1080-41BB and CHO cells following treatment with His-tagged SIRPα-41BBL protein (SEQ ID NO: 5). FIG. 8B is a graph demonstrating IL-8 concentration in supernatant of HT1080-41BB cell cultures and co-cultures of HT1080-41BB and CHO-CD47 cells following treatment with His-tagged SIRPα-41BBL protein (SEQ ID NO: 5). FIG. 8C is a graph demonstrating T cells activation, as evaluated by CD25 expression, in T cells cultured for 3 days in 96-wells plates coated with CD47:Fc and treated with a sub-optimal concentration of anti-CD3/anti-CD38 beads and increasing concentrations of His-tagged SIRPα-41BBL (SEQ ID NO: 5). FIGS. 8D-E shows representative dot plots (FIG. 8D) and a summarizing graph (mean±standard error, two independent donors were taken in two independent experiments. Each donor was analyzed in triplicates. FIG. 8E are dot plots demonstrating T cells activation, as evaluated by CD25 expression, in co-cultures of T cells isolated from peripheral blood of healthy volunteers mixed with DLD-1 cells and treated for 3 days with a sub-optimal concentration of anti-CD3/anti-CD28 beads with or without His-tagged SIRPα-41BBL protein (SEQ ID NO: 5).

FIG. 9A is a histogram demonstrating CD47 expression on the surface of MV4-11 cells, FIG. 9B demonstrates binding of His-tagged SIRPα-41BBL protein (SEQ ID NO: 5) to MV4-11 cells. The cells were incubated with Fc-blocker for 15 minutes on ice followed by incubation with different concentrations of His-tagged SIRPα-41BBL protein (SEQ ID NO: 5) for 30 minutes, immuno-staining with anti-41BBL antibody and flow cytometry analysis. FIG. 9C is a graph showing that incubation of MV4-11 cells with different concentrations of His-tagged SIRPα-41BBL protein (SEQ ID NO: 5) for up to 72 hours did not show any direct killing effect, as determined by PI staining.

FIG. 10A is a graph demonstrating IFN-γ concentration detected in the culture supernatant of human PBMCs incubated for 40 hours with different concentrations of His-tagged SIRPα-41BBL protein (SEQ ID NO: 5) in the presence of anti-CD3 or anti-CD3 plus IL2, as indicated. FIG. 10B is a graph demonstrating IFN-γ concentration detected in the culture supernatant of human PBMCs co-cultured with human cancer MV-4-11 cells and incubated for 40 hours with different concentrations of His-tagged SIRPα-41BBL protein (SEQ ID NO: 5), with or without anti-CD3; and with or without IL2, as indicated.

FIGS. 11A-L demonstrate that SIRPα-41BBL potentiates granulocyte-mediated phagocytosis. FIG. 11A shows a representative gating strategy of the flow cytometric phagocytosis analysis. FIG. 11B is a graph demonstrating phagocytosis of B-cell lymphoma cell line BJAB by granulocytes following treatment with the indicated concentrations of His-tagged SIRPα-41BBL protein (SEQ ID NO: 5). FIG. 11C is a graph demonstrating phagocytosis of the indicated B-cell lymphoma cell lines by granulocytes obtained from 2-3 individual donors incubated with or without His-tagged SIRPα-41BBL protein (SEQ ID NO: 5). FIG. 11D is a graph demonstrating phagocytosis of the indicated B-cell lymphoma cell lines by granulocytes following treatment with rituximab with or without His-tagged SIRPα-41BBL protein (SEQ ID NO: 5). FIG. 11E is a graph demonstrating phagocytosis of the indicated carcinoma cell lines by granulocytes obtained from 3-6 individual donors incubated with or without His-tagged SIRPα-41BBL protein (SEQ ID NO: 5). FIG. 11F is a graph demonstrating phagocytosis of the indicated carcinoma cell lines by granulocytes following treatment with cetuximab with or without His-tagged SIRPα-41BBL protein (SEQ ID NO: 5). FIG. 11G is a graph demonstrating phagocytosis of the indicated myeloid leukemia cell lines by granulocytes obtained from 3 individual donors incubated for 2 hours with or without His-tagged SIRPα-41BBL protein (SEQ ID NO: 5). FIG. 11H is a graph demonstrating phagocytosis of the indicated myeloid leukemia cell lines by granulocytes obtained from 3 individual donors incubated for 24 hours with or without His-tagged SIRPα-41BBL protein (SEQ ID NO: 5). FIG. 11I is a graph demonstrating phagocytosis of HL60 and MOLM13 by granulocytes following treatment with the indicated concentrations of His-tagged SIRPα-41BBL protein (SEQ ID NO: 5). FIG. 11J is a graph demonstrating phagocytosis of primary acute myeloid leukaemia cells by granulocytes following 2 hours or 24 hours treatment with the indicated concentrations of His-tagged SIRPα-41BBL protein (SEQ ID NO: 5). FIG. 11K is a graph demonstrating phagocytosis (mean±standard error) of primary acute myeloid leukaemia cells by allogeneic granulocytes obtained from 5 individual donors following 2 hours or 24 hours incubation with or without 2.5 μg/ml His-tagged SIRPα-41BBL protein (SEQ ID NO: 5). FIG. 11L shows phagocytosis of DLD1 cancer cells by polymorphonuclear cells treated for 2 hours with soluble SIRPα, soluble 41BBL, combination of both or His tagged-SIRPα-41BBL fusion protein (SEQ ID NO: 5).

FIG. 12A shows representative microscopic pictures of co-cultures of macrophages and B-cell lymphoma cell line U2932 pre-stained V450 following 2 hours of incubation with or without His-tagged SIRPα-41BBL protein (SEQ ID NO: 5) and with or without the monoclonal antibody rituximab (mAb). Adhered macrophages are visible in bright-field, with V450-labelled cancer cells being visible as bright cells. Dark arrows indicate viable tumour cells. White arrows indicate tumor cells that have been phagocytosed by macrophages.

FIG. 12B is a graph demonstrating macrophage-mediated phagocytosis of U2932 cells following treatment with the indicated concentrations of His-tagged SIRPα-41BBL protein (SEQ ID NO: 5). FIG. 12C is a graph demonstrating macrophage-mediated phagocytosis of U2932 cells following treatment with rituximab with or without His-tagged SIRPα-41BBL protein (SEQ ID NO: 5). FIG. 12D is a graph demonstrating macrophage-induced phagocytosis (mean±standard error) of primary B-cell malignant chronic lymphocytic leukaemia incubated with or without His-tagged SIRPα-41BBL protein (SEQ ID NO: 5) and with or without alemtuzumab, FIGS. 13A-B demonstrate that treatment of CT-26 inoculated mice with His-tagged SIRPα-41BBL protein (SEQ ID NO: 5) reduces tumor volume FIG. 13A is a schematic illustration of experiment timelines: mice were inoculated S.C. with $1 \times 10^6$ CT-26 cells on day 0, PBS control, aPD1 or SIRPα-41BBL were injected on days 3, 7 and 10. FIG. 13B is a graph demonstrating mean±standard error) tumor volume in the three treatment groups.

FIGS. 14A-B demonstrate that His-tagged SIRPα-41BBL protein (SEQ ID NO: 5) is effective for the treatment of mice inoculated with P388 syngeneic leukemia tumor. FIG. 14A is a schematic illustration of experiment timelines: mice were inoculated I.P. with $1 \times 10^6$ P388 cells on day 0, PBS control, aPD1 or SIRPα-41BBL were injected on days 1, 3, 5, and 7. FIG. 14B is a graph demonstrating spleen weight in the three treatment groups upon sacrifice.

FIGS. 15A-C demonstrate that His-tagged SIRPα-41BBL protein (SEQ ID NO: 5) decreases tumor burden in the BM of NSG mice inoculated with human leukemia tumor. FIG. 15A is a schematic illustration of experiment timelines: mice were irradiated 24 hr before inoculation of MV4.11 cells, thirteen (13) days later mice were inoculated with human PBMCs, treatment started 4 hours later. 5 animals per group were administered every-other-day (EOD) injections with four intraperitoneal of His-tagged SIRPα-41BBL protein (100 μg/injection) or its soluble buffer (PBS) (on days 13, 15, 17 and 19). Twenty-four (24) hours after the last injection mice were sacrificed. FIG. 15B shows the number of leukemic cells in the BM as was determined using flow cytometry. FIG. 15C shows spleen weight in mg.

DESCRIPTION OF DETAILED EMBODIMENTS OF THE INVENTION

Figure 6:
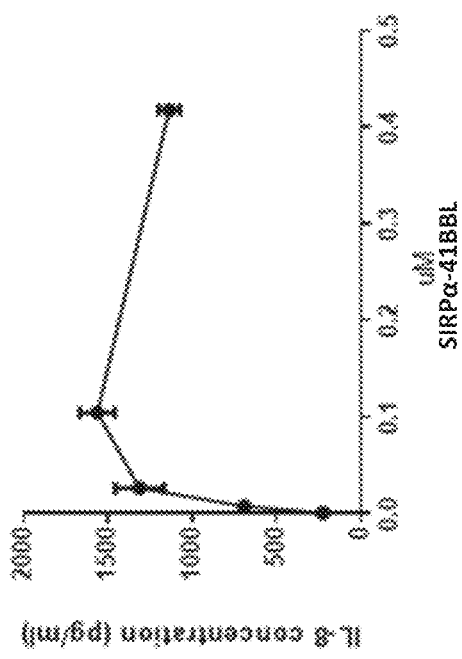
FIG. 6 is a graph demonstrating that His-tagged SIRPα-41BBL protein (SEQ ID NO: 5) promotes TNFR signaling as demonstrated by IL-8 secretion from HT1080-41BB cells in medium containing FBS.

The present invention, in some embodiments thereof, relates to a SIRPα-41BBL fusion protein and methods of use thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Dual Signaling Proteins (DSP), also known as Signal-Converting-Proteins (SCP), which are currently known in the art as bi-functional fusion proteins that link an extracellular portion of a type I membrane protein (extracellular amino-terminus), to an extracellular portion of a type II membrane protein (extracellular carboxyl-terminus), forming a fusion protein with two active sides.

Surprisingly, it was found that a specific fusion protein may be advantageously administered to subjects suffering from cancerous diseases, depending upon the presence of tumors that have tumor-infiltrating lymphocytes (TILs) in the tumor micro-environment as well as tumors with relatively high expression of CD47 on the tumor cells or in the tumor micro-environment.

As is illustrated hereinunder and in the examples section, which follows, the present inventors have produced a his-tagged SIRPα-41BBL fusion protein (SEQ ID NO: 5) and show that the fusion protein (SEQ ID NO: 5) contains both domains and produced in the form of at least trimers (Experiments 1A-B, FIGS. 1 and 2A-C). Following, the present inventors demonstrate that the produced his-tagged SIRPα-41BBL fusion protein (SEQ ID NO: 5) retains functional binding activity for its cognate receptors CD47 and 41BB (Experiments 1C-D, FIGS. 3A-B, 4A-B and 5A-B) and can trigger 41BB co-stimulation and activation of cells expressing 41BB (e.g. T cells, PBMCs) wherein presence of CD47 augments this activity (Experiments 2-3 and 3A-B, FIGS. 6-7, 8A-E 9A-C and 10A-B). In addition, the inventors demonstrate that the His-tagged SIRPα-41BBL (SEQ ID NO: 5) through its SIRPα domain augments phagocytic uptake of various malignant cell types, including primary malignant cells, particularly in combination treatment with various therapeutic monoclonal antibodies currently in clinical use (Experiment 4 FIGS. 11A-L and 12A-D). The inventors further demonstrate that his-tagged SIRPα-41BBL fusion protein (SEQ ID NO: 5) is effective for the treatment of tumors as shown in in-vivo colon carcinoma and leukemia mouse tumor models (Experiments 5 and 5A-C, FIGS. 13A-B, 14A-B and 15A-C).

Consequently, the present teachings suggest SIRPα-41BBL fusion proteins, polynucleotides encoding same and host cells expressing same; and uses of same in e.g. activating immune cells (via co-stimulation) in general and treating diseases that can benefit from activating immune cells (e.g. cancer) in particular.

Thus, according to a first aspect of the present invention, there is provided a SIRPα-41BBL fusion protein or any variants or fragments thereof or a SIRPα-41BBL fusion protein, which is at least about 70%, homologous to the sequence as set forth in SEQ ID No. 4 optionally with a linker therebetween.

According to another aspect of the present invention, there is provided a SIRPα-41BBL fusion protein comprising a single amino acid linker between said SIRPα and said 41BBL.

According to another aspect of the present invention, there is provided a SIRPα-41BBL fusion protein in a form of at least a homo-trimer.

According to specific embodiments, at least 10%, at least 20%, at least 30%, at least 40%, at least 50%, at least 60%, at least 70%, at least 80%, at least 90%, at least 95% of the SIRPα-41BBL fusion protein is in a form of at least a homo-trimer, each possibility represents a separate embodiment of the present invention.

According to specific embodiments, the at least homo-trimer comprises a homo-trimer.

According to specific embodiments, the at least homo-trimer comprises a homo-tetramer.

According to specific embodiments, the at least homo-trimer comprises a homo-pentamer.

According to specific embodiments, the at least homo-trimer comprises a homo-hexamer.

Methods of determining trimerization are well known in the art and include, but are not limited to SDS-PAGE, NATIVE-PAGE, SEC-HPLC, 2D gels, gel filtration, SEC MALLS, Analytical ultracentrifugation (AUC) Mass spectrometry (MS), capillary gel electrophoresis (CGE).

According to specific embodiments the at least homo-trimer is at least 140 kD, at least 160 kD, at least 180 kD at least 200 kD, at least 220 kD, at least 240 kD in molecular weight as determined by SDS-PAGE.

According to specific embodiments the at least homo-trimer is at least 140 kD in molecular weight as determined by SDS-PAGE.

According to specific embodiments, the at least homo-trimer is at least 200 kD in molecular weight as determined by SDS-PAGE.

As used herein the term "SIRPα (Signal Regulatory Protein Alpha, also known as CD172a)" refers to the polypeptide of the SIRP1 gene (Gene ID 140885) or a functional homolog e.g., functional fragment thereof. According to specific embodiments, the term "SIRPα" refers to a functional homolog of SIRPα polypeptide. According to specific embodiments, SIRPα is human SIRPα. According to a specific embodiment, the SIRPα protein refers to the human protein, such as provided in the following GenBank Number NP_005009.

As used herein, a "functional SIRPα" is capable of binding its cognate receptor CD47 [also known as integrin associated protein (IAP)].

As use herein, the phrase "functional homolog" or "functional fragment" when related to SIRPα, refers to a portion of the polypeptide which maintains the activity of the full length SIRPα e.g., CD47 binding.

According to a specific embodiment, the CD47 protein refers to the human protein, such as provided in the following GenBank Numbers NP_001768 or NP_942088.

Assays for testing binding are well known in the art and include, but not limited to flow cytometry, BiaCore, bio-layer interferometry Blitz® assay, HPLC.

According to specific embodiments, the SIRPα binds CD47 with a Kd of 0.1-100 µM, 0.1-10 µM, 1-10 µM, 0.1-5 µM, or 1-2 µM as determined by SPR, each possibility represented a separate embodiment of the present invention.

According to specific embodiments, the SIRPα comprises an extracellular domain of said SIRPα or a functional fragment thereof.

According to specific embodiments, SIRPα amino acid sequence comprises SEQ ID NO: 9.

According to specific embodiments, SIRPα amino acid sequence consists of SEQ ID NO: 9.

According to specific embodiments, SIRPα nucleic acid sequence comprises SEQ ID NO: 10.

According to specific embodiments, SIRPα nucleic acid sequence consists of SEQ ID NO: 10.

According to specific embodiments, SIRPα amino acid sequence comprises SEQ ID NO: 2.

According to specific embodiments, SIRPα amino acid sequence consists of SEQ ID NO: 2.

According to specific embodiments, SIRPα nucleic acid sequence comprises SEQ ID NO: 11.

According to specific embodiments, SIRPα nucleic acid sequence consists of SEQ ID NO: 11.

The term "SIRPα" also encompasses functional homologues (naturally occurring or synthetically/recombinantly produced), which exhibit the desired activity (i.e., binding CD47). Such homologues can be, for example, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID NO: 2 or 9; or at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same (as further described hereinbelow).

Sequence identity or homology can be determined using any protein or nucleic acid sequence alignment algorithm such as Blast, ClustalW, and MUSCLE.

The homolog may also refer to an ortholog, a deletion, insertion, or substitution variant, including an amino acid substitution, as further described hereinbelow.

According to specific embodiments, the SIRPα polypeptide may comprise conservative amino acid substitutions as further described hereinbelow.

According to specific embodiments, SIRPα amino acid sequence comprises 100-500 amino acids, 150-450 amino acids, 200-400 amino acids, 250-400 amino acids, 300-400 amino acids, 320-420 amino acids, 340-350 amino acids, each possibility represents a separate embodiment of the present invention.

According to specific embodiments, SIRPα amino acid sequence is 300-400 amino acids in length.

According to specific embodiments, SIRPα amino acid sequence is 340-450 amino acids in length.

According to specific embodiments, SIRPα amino acid sequence is 343 amino acids in length.

As used herein the term "41BBL (also known as CD137L and TNFSF9)" refers to the polypeptide of the TNFSF9 gene (Gene ID 8744) or a functional homolog e.g., functional fragment thereof. According to specific embodiments, the term "41BBL" refers to a functional homolog of 41BBL polypeptide. According to specific embodiments, 41BBL is human 41BBL. According to a specific embodiment, the 41BBL protein refers to the human protein, such as provided in the following GenBank Number NP_003802.

According to specific embodiments, the 41BBL comprises an extracellular domain of said 41BBL or a functional fragment thereof.

According to specific embodiments, 41BBL amino acid sequence comprises SEQ ID NO: 12.

According to specific embodiments, 41BBL amino acid sequence consists of SEQ ID NO: 12.

According to specific embodiments, 41BBL nucleic acid sequence comprises SEQ ID NO: 13.

According to specific embodiments, 41BBL nucleic acid sequence consists of SEQ ID NO: 13.

According to specific embodiments, 41BBL amino acid sequence comprises SEQ ID NO: 3.

According to specific embodiments, 41BBL amino acid sequence consists of SEQ ID NO: 3.

According to specific embodiments, 41BBL nucleic acid sequence comprises SEQ ID NO: 14.

According to specific embodiments, 41BBL nucleic acid sequence consists of SEQ ID NO: 14.

The term "41BBL" also encompasses functional homologues (naturally occurring or synthetically/recombinantly produced), which exhibit the desired activity (as defined hereinbelow). Such homologues can be, for example, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID NO: 3, 12; or at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same (as further described hereinbelow).

According to specific embodiments, the 41BBL polypeptide may comprise conservative amino acid substitutions, as further described hereinbelow.

According to specific embodiments, 41BBL amino acid sequence comprises 100-300 amino acids, 150-250 amino acids, 100-250 amino acids, 150-220 amino acids, 180-220 amino acids, 190-210 amino acids, each possibility represents a separate embodiment of the present invention.

According to specific embodiments, 41BBL amino acid sequence is 190-210 amino acids in length.

According to specific embodiments, 41BBL amino acid sequence is 204 amino acids in length.

As used herein, a "functional 41BBL" is capable of least one of:
(i) binding its cognate receptor 41BB (also known as CD137),
(ii) activating 41BB signaling pathway in an immune cell expressing 41BB; and/or
(iii) activating immune cells expressing said 41BB.

According to specific embodiments, functional 41BBL is capable of (i), (ii), (iii), (i)+(ii), (i)+(iii), (ii)+(iii).

According to specific embodiments, functional 41BBL is capable of (i)+(ii)+(iii).

As use herein, the phrase "functional homolog" or "functional fragment" when related to 41BBL, refers to a portion of the polypeptide which maintains the activity of the full length 41BBL e.g., binding 41BB, activating 41BB signaling pathway, activating immune cells expressing 41BB.

According to a specific embodiment, the 41BB protein refers to the human protein, such as provided in the following GenBank Number NP_001552.

Assays for testing binding are well known in the art and are further described hereinabove According to specific embodiments, the 41BBL binds 41BB with a Kd of about 0.1-1000 nM, 0.1-100 nM, 1-100 nM, or 55.2 nM as determined by SPR, each possibility represents a separate embodiment of the claimed invention.

As used herein the terms "activating" or "activation" refer to the process of stimulating an immune cell (e.g. T cell, B cell, NK cell, phagocytic cell) that results in cellular proliferation, maturation, cytokine production, phagocytosis and/or induction of regulatory or effector functions.

According to specific embodiments, activating comprises co-stimulating.

As used herein the term "co-stimulating" or "co-stimulation" refers to transmitting a secondary antigen independent stimulatory signal (e.g. 41BB signal) resulting in activation of the immune cell.

According to specific embodiments, activating comprises suppressing an inhibitory signal (e.g. CD47 signal) resulting in activation of the immune cell.

Methods of determining signaling of a stimulatory or inhibitory signal are well known in the art and also disclosed in the Examples section which follows, and include, but are not limited to, binding assay using e.g. BiaCore, HPLC or flow cytometry, enzymatic activity assays such as kinase activity assays, and expression of molecules involved in the signaling cascade using e.g.

PCR, Western blot, immunoprecipitation and immunohistochemistry. Additionally or alternatively, determining transmission of a signal (co-stimulatory or inhibitory) can be effected by evaluating immune cell activation or function. Methods of evaluating immune cell activation or function are well known in the art and include, but are not limited to, proliferation assays such as CFSE staining, MTS, Alamar blue, BRDU and thymidine incorporation, cytotoxicity assays such as CFSE staining, chromium release, Calcin AM, cytokine secretion assays such as intracellular cytokine staining, ELISPOT and ELISA, expression of activation markers such as CD25, CD69, CD137, CD107a, PD1, and CD62L using flow cytometry.

According to specific embodiments, determining the signaling activity or activation is effected in-vitro or ex-vivo e.g. in a mixed lymphocyte reaction (MLR), as further described hereinbelow.

For the same culture conditions the signaling activity or the immune cell activation or function are generally expressed in comparison to the signaling, activation or function in a cell of the same species but not contacted with the SIRPα-41BBL fusion protein, a polynucleotide encoding same or a host cell encoding same; or contacted with a vehicle control, also referred to as control.

The terms "DSP" and "fusion protein", "chimeric protein" or "chimera" are used herein interchangeably, and refer to an amino acid sequence having two or more parts which are not found together in a single amino acid sequence in nature.

In one embodiment, the present invention is directed to a fusion protein comprising a SIRPα-41BBL, (hereinafter, SIRPα-41BBL fusion protein) or any variants or fragments thereof optionally with a linker therebetween.

SIRPα-41BBL is a Dual Signaling Protein (DSP) chimera protein fusing the extracellular domains of two different human membrane proteins. The N terminal domain is the extracellular domain of the human SIRPα (gene: SIRPA), which is a type 1 membrane protein, and the C terminal domain of the chimera is the extracellular domain of the human 41BBL (gene: 41BBL), which is a type 2 membrane protein.

According to specific embodiments, the SIRPα-41BBL fusion protein is soluble (i.e., not immobilized to a synthetic or a naturally occurring surface).

According to specific embodiments, the SIRPα-41BBL fusion protein is immobilized to a synthetic or a naturally occurring surface.

According to specific embodiments, the SIRPα-41BBL does not comprise a linker between the SIRPα and the 41BBL.

In some embodiment, the SIRPα-41BBL comprises a linker which may be at any length.

Hence, according to specific embodiments the SIRPα-41BBL fusion protein comprises a linker between said SIRPα and said 41BBL.

Any linker known in the art can be used with specific embodiments of the invention.

According to specific embodiments, the linker may be derived from naturally-occurring multi-domain proteins or is an empirical linker as described, for example, in Chichili et al., (2013), Protein Sci. 22(2): 153-167, Chen et al., (2013), Adv Drug Deliv Rev. 65(10): 1357-1369, the entire contents of which are hereby incorporated by reference. In some embodiments, the linker may be designed using linker designing databases and computer programs such as those described in Chen et al., (2013), Adv Drug Deliv Rev. 65(10): 1357-1369 and Crasto et al (2000), Protein Eng. 13(5):309-312, the entire contents of which are hereby incorporated by reference.

According to specific embodiments, the linker is a synthetic linker such as PEG.

According to specific embodiments, the linker is an Fc domain or the hinge region of an antibody (e.g., of IgG, IgA, IgD or IgE) or a fragment thereof.

According to other specific embodiments, the linker is not an Fc domain or a hinge region of an antibody or a fragment thereof.

According to specific embodiments, the linker may be functional. For example, without limitation, the linker may function to improve the folding and/or stability, improve the expression, improve the pharmacokinetics, and/or improve the bioactivity of the SIRPα-41BBL fusion protein. In another example, the linker may function to target the SIRPα-41BBL fusion protein to a particular cell type or location.

According to specific embodiments, the linker is a polypeptide.

In some embodiments, the SIRPα-41BBL comprises a linker at a length of one to six amino acids.

According to specific embodiments, the linker is substantially comprised of glycine and/or serine residues (e.g. about 30%, or about 40%, or about 50%, or about 60%, or about 70%, or about 80%, or about 90%, or about 95%, or about 97% or 100% glycines and serines).

According to specific embodiments, the linker is a single amino acid linker.

In some embodiments of the invention, the amino acid which links SIRPα and 41BBL is glycine, also referred to herein as SIRPα-G-41BBL fusion protein.

According to specific embodiments, the SIRPα-41BBL fusion protein amino acid sequence comprises SEQ ID NO: 1.

According to specific embodiments, the SIRPα-41BBL fusion protein amino acid sequence consists of SEQ ID NO: 1.

In some embodiments, the term "SIRPα-G-41BBL fusion protein" refers to a protein identified by SEQ ID NO. 1:

Amino-acid sequence of the chimera protein (SIRPα-G-41BBL):
<u>EEELQVIQPDKSVLVAAGETATLRCTATSLIPVGPIQWFRGAGPGRELIY</u>

<u>NQKEGHFPRVTTVSDLTKRNNMDFSIRIGNITPADAGTYYCVKFRKGSPD</u>

<u>DVEFKSGAGTELSVRAKPSAPVVSGPAARATPQHTVSFTCESHGFSPRDI</u>

<u>TLKWFKNGNELSDFQTNVDPVGESVSYSIHSTAKVVLTREDVHSQVICEV</u>

<u>AHVTLQGDPLRGTANLSETIRVPPTLEVTQQPVRAENQVNVTCQVRKFYP</u>

<u>QRLQLTWLENGNVSRTETASTVTENKDGTYNWMSWLLVNVSAHRDDVKLT</u>

<u>CQVEHDGQPAVSKSHDLKVSAHPKEQGSNTAAENTGSNERNIYG</u>ACPWAV

SGARASPGSAASPRLREGPELSPDDPAGLLDLRQGMFAQLVAQNVLLIDG

PLSWYSDPGLAGVSLTGGLSYKEDTKELVVAKAGVYYVFFQLELRRVVAG

EGSGSVSLALHLQPLRSAAGAAALALTVDLPPASSEARNSAFGFQGRLLH

LSAGQRLGVHLHTEARARHAWQLTQGATVLGLFRVTPEIPAGLPSPRSE

The extracellular domain of the human SIRPα protein is underlined i.e.

(SEQ ID NO. 2)
EEELQVIQPDKSVLVAAGETATLRCTATSLIPVGPIQWFRGAGPGRELIY

NQKEGHFPRVTTVSDLTKRNNMDFSIRIGNITPADAGTYYCVKFRKGSPD

DVEFKSGAGTELSVRAKPSAPVVSGPAARATPQHTVSFTCESHGFSPRDI

TLKWFKNGNELSDFQTNVDPVGESVSYSNISTAKVVLTREDVHSQVICEV

AHVTLQGDPLRGTANLSETIRVPPTLEVTQQPVRAENQVNVTCQVRKFYP

QRLQLTWLENGNVSRTETASTVTENKDGTYNWMSWLLVNVSAHRDDVKLT

CQVEHDGQPAVSKSHDLKVSAHPKEQGSNTAAENTGSNERNIY

The extracellular domain of the human 41BBL is bold i.e.

(SEQ ID NO. 3)
ACPWAVSGARASPGSAASPRLREGPELSPDDPAGLLDLRQGMFAQLVAQN

VLLIDGPLSWYSDPGLAGVSLTGGLSYKEDTKELVVAKAGVYYVFFQLEL

-continued
RRVVAGEGSGSVSLALHLQPLRSAAGAAALALTVDLPPASSEARNSAFGF

QGRLLHLSAGQRLGVHLHTEARARHAWQLTQGATVLGLFRVTPEIPAGLP

SPRSE

According to specific embodiments, the amino acid sequence of SIRPα-G-41BBL is at least about 70%, 75%, 80%, 85%, 90%, 95%, 96%, 97%, 98% or 99% homologous to the amino acid sequence as set forth in SEQ ID No. 1 or to the polynucleotide sequence encoding same.

In some embodiments, there is provided a SIRPα-41BBL fusion protein, which is at least about 70%, 75%, 80%, 85%, 90%, 95%, 96%, 97%, 98% or 99% homologous to the sequence as set forth in SEQ ID No. 4 optionally with a linker between SIRPα peptide or the ECD thereof and 41BBL peptide or the ECD thereof, wherein SEQ ID No. 4 is:

EEELQVIQPDKSVLVAAGETATLRCTATSLIPVGPIQWFRGAGPGRELIY

NQKEGHFPRVTTVSDLTKRNNMDFSIRIGNITPADAGTYYCVKFRKGSPD

DVEFKSGAGTELSVRAKPSAPVVSGPAARATPQHTVSFTCESHGFSPRDI

TLKWFKNGNELSDFQTNVDPVGESVSYSIHSTAKVVLTREDVHSQVICEV

AHVTLQGDPLRGTANLSETIRVPPTLEVTQQPVRAENQVNVTCQVRKFYP

QRLQLTWLENGNVSRTETASTVTENKDGTYNWMSWLLVNVSAHRDDVKLT

CQVEHDGQPAVSKSHDLKVSAHPKEQGSNTAAENTGSNERNIYACPWAVS

GARASPGSAASPRLREGPELSPDDPAGLLDLRQGMFAQLVAQNVLLIDGP

LSWYSDPGLAGVSLTGGLSYKEDTKELVVAKAGVYYVFFQLELRRVVAGE

GSGSVSLALHLQPLRSAAGAAALALTVDLPPASSEARNSAFGFQGRLLHL

SAGQRLGVHLHTEARARHAWQLTQGATVLGLFRVTPEIPAGLPSPRSE

In some embodiments, there is provided a SIRPα-41BBL as set forth in SEQ ID No. 4 optionally with a linker between SIRPα peptide or the ECD thereof and 41BBL peptide or the ECD thereof, wherein SEQ ID No. 4 is:

EEELQVIQPDKSVLVAAGETATLRCTATSLIPVGPIQWFRGAGPGRELIY

NQKEGHFPRVTTVSDLTKRNNMDFSIRIGNITPADAGTYYCVKFRKGSPD

DVEFKSGAGTELSVRAKPSAPVVSGPAARATPQHTVSFTCESHGFSPRDI

TLKWFKNGNELSDFQTNVDPVGESVSYSNISTAKVVLTREDVHSQVICEV

AHVTLQGDPLRGTANLSETIRVPPTLEVTQQPVRAENQVNVTCQVRKFYP

QRLQLTWLENGNVSRTETASTVTENKDGTYNWMSWLLVNVSAHRDDVKLT

CQVEHDGQPAVSKSHDLKVSAHPKEQGSNTAAENTGSNERNIYACPWAVS

GARASPGSAASPRLREGPELSPDDPAGLLDLRQGMFAQLVAQNVLLIDGP

LSWYSDPGLAGVSLTGGLSYKEDTKELVVAKAGVYYVFFQLELRRVVAGE

GSGSVSLALHLQPLRSAAGAAALALTVDLPPASSEARNSAFGFQGRLLHL

SAGQRLGVHLHTEARARHAWQLTQGATVLGLFRVTPEIPAGLPSPRSE

In additional embodiments, the SIRPA-G-41BBL fusion protein may be a variant and/or derivative of the amino acid sequence shown in SEQ ID NO. 1. A number of such variants are known in the art, see as for example in Weiskopf et al, 2013; Young Won, et al, 2010 and Rabu, et al, 2005; Hereby incorporated by reference as if fully set forth herein.

According to specific embodiments, the SIRPα-41BBL fusion protein is capable of least one of:
  (i) binding CD47 and 41BB,
  (ii) activating 41BB signaling pathway in an immune cell (e.g. T cell) expressing 41BB;
  (iii) activating immune cells (e.g. T cells) expressing said 41BB; and/or
  (iv) enhancing phagocytosis of pathologic cells expressing CD47 by phagocytes compared to same in the absence of SIRPα-41BBL fusion protein.

According to specific embodiments, the SIRPα-41BBL fusion protein is capable of (i), (ii), (iii), (iv), (i)+(ii), (i)+(iii), (i)+(iv), (ii)+(iii), (ii)+(iv), (i)+(ii)+(iii), (i)+(ii)+(iv), (ii)+(iii)+(iv).

According to specific embodiments, the SIRPα-41BBL fusion protein is capable of (i)+(ii)+(iii)+(iv).

Methods of determining binding, activating 41BB signaling pathway and activating immune cells are well known in the art and are further described hereinabove and below and in the Examples section which follows.

According to specific embodiments, the SIRPα-41BBL fusion protein enhances phagocytosis of pathologic cells expressing CD47 by phagocytes.

Methods of analyzing phagocytosis are well known in the art and are also disclosed in Experiment 4 in the Examples section which follows; and include for examples killing assays, flow cytometry and/or microscopic evaluation (live cell imaging, fluorescent microscopy confocal microscopy, electron microscopy).

According to specific embodiments the enhancement in phagocytosis is at least 1.5 fold, at least 2 fold, at least 3 fold, at least 5 fold, at least 10 fold, or at least 20 fold as compared to same in the absence of the SIRPα-41BBL fusion protein, the polynucleotide or nucleic acid construct encoding same or the host cell expressing same of the present invention, as determined by e.g. flow cytometry or microscopic evaluation.

According to other specific embodiments the increase in survival is by at least 5%, by at least a 10%, at least 20%, at least 30%, at least 40%, at least 50%, at least 60%, at least 70%, at least 80%, at least 90%, at least 95% or at least 100% as compared to same in the absence of the SIRPα-41BBL fusion protein, the polynucleotide or nucleic acid construct encoding same or the host cell expressing same of the present invention, as determined by e.g. flow cytometry or microscopic evaluation.

As the compositions of some embodiments of present invention (e.g. the fusion protein, a polynucleotide or nucleic acid encoding same or a host cell expressing same) are capable of activating immune cells, they can be used in method of activating immune cells, in-vitro, ex-vivo and/or in-vivo.

Thus, according to an aspect of the present invention, there is provided a method of activating immune cells, the method comprising in-vitro or ex-vivo activating immune cells in the presence of a SIRPα-41BBL fusion protein, a polynucleotide encoding same, a nucleic acid construct encoding same or a host cell expressing same.

According to another aspect of the present invention, there is provided a method of activating T cells, the method comprising in-vitro or ex-vivo activating T cells in the presence of a SIRPα-41BBL fusion protein and cells expressing CD47.

According to another aspect of the present invention, there is provided a method of activating phagocytes, the method comprising in-vitro activating phagocytes in the presence of a SIRPα-41BBL fusion protein and cells expressing CD47.

According to specific embodiments, the immune cells express 41BB.

According to specific embodiments, the immune cells comprise peripheral mononuclear blood cells (PBMCs).

As used herein the term "peripheral mononuclear blood cells (PBMCs)" refers to a blood cell having a single nucleus and includes lymphocytes, monocytes and dendritic cells (DCs).

According to specific embodiments, the PBMCs are selected from the group consisting of dendritic cells (DCs), T cells, B cells, NK cells and NKT cells.

According to specific embodiments, the PBMCs comprise T cells, B cells, NK cells and NKT cells.

Methods of obtaining PBMCs are well known in the art, such as drawing whole blood from a subject and collection in a container containing an anti-coagulant (e.g. heparin or citrate); and apheresis. Following, according to specific embodiments, at least one type of PBMCs is purified from the peripheral blood. There are several methods and reagents known to those skilled in the art for purifying PBMCs from whole blood such as leukapheresis, sedimentation, density gradient centrifugation (e.g. ficoll), centrifugal elutriation, fractionation, chemical lysis of e.g. red blood cells (e.g. by ACK), selection of specific cell types using cell surface markers (using e.g. FACS sorter or magnetic cell separation techniques such as are commercially available e.g. from Invitrogen, Stemcell Technologies, Cellpro, Advanced Magnetics, or Miltenyi Biotec.), and depletion of specific cell types by methods such as eradication (e.g. killing) with specific antibodies or by affinity based purification based on negative selection (using e.g. magnetic cell separation techniques, FACS sorter and/or capture ELISA labeling).

Such methods are described for example in THE HANDBOOK OF EXPERIMENTAL IMMUNOLOGY, Volumes 1 to 4, (D. N. Weir, editor) and FLOW CYTOMETRY AND CELL SORTING (A. Radbruch, editor, Springer Verlag, 2000).

According to specific embodiments, the immune cells comprise tumor infiltrating lymphocytes.

As used herein the term "tumor infiltrating lymphocytes (TILs) refers to mononuclear white blood cells that have left the bloodstream and migrated into a tumor.

According to specific embodiments, the TILs are selected from the group consisting of T cells, B cells, NK cells and monocytes.

Methods of obtaining TILs are well known in the art, such as obtaining tumor samples from a subject by e.g. biopsy or necropsy and preparing a single cell suspension thereof. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Following, the at least one type of TILs can be purified from the cell suspension. There are several methods and reagents known to those skilled in the art for purifying the desired type of TILs, such as selection of specific cell types using cell surface markers (using e.g. FACS sorter or magnetic cell separation techniques such as are commercially available e.g. from Invitrogen, Stemcell Technologies, Cellpro, Advanced Magnetics, or Miltenyi Biotec.), and depletion of specific cell types by methods such as eradication (e.g. killing) with specific antibodies or by affinity based purification based on negative selection (using e.g. magnetic cell separation techniques, FACS sorter and/or capture ELISA labeling). Such methods are described for example in THE HANDBOOK OF EXPERIMENTAL IMMUNOLOGY, Volumes 1 to 4, (D. N. Weir, editor) and FLOW CYTOMETRY AND CELL SORTING (A. Radbruch, editor, Springer Verlag, 2000).

According to specific embodiments, the immune cells comprise phagocytes.

As used herein, the term "phagocytes" refer to a cell that is capable of phagocytosis and include both professional and non-professional phagocytes. Methods of analyzing phagocytosis are well known in the art and are further disclosed hereinabove and below. According to specific embodiments, the phagocytic cells are selected from the group consisting of monocytes, dendritic cells (DCs) and granulocytes.

According to specific embodiments, the phagocytes comprise granulocytes.

According to specific embodiments, the phagocytes comprise monocytes.

According to specific embodiments, the immune cells comprise monocytes.

According to specific embodiments, the term "monocytes" refers to both circulating monocytes and to macrophages (also referred to as mononuclear phagocytes) present in a tissue.

According to specific embodiments, the monocytes comprise macrophages. Typically, cell surface phenotype of macrophages include CD14, CD40, CD11b, CD64, F4/80 (mice)/EMR1 (human), lysozyme M, MAC-1/MAC-3 and CD68.

According to specific embodiments, the monocytes comprise circulating monocytes. Typically, cell surface phenotypes of circulating monocytes include CD14 and CD16 (e.g. CD14++CD16-, CD14+CD16++, CD14++CD16+).

According to specific embodiments, the immune cells comprise DCs

As used herein the term "dendritic cells (DCs)" refers to any member of a diverse population of morphologically similar cell types found in lymphoid or non-lymphoid tissues. DCs are a class of professional antigen presenting cells, and have a high capacity for sensitizing HLA-restricted T cells. DCs include, for example, plasmacytoid dendritic cells, myeloid dendritic cells (including immature and mature dendritic cells), Langerhans cells, interdigitating cells, follicular dendritic cells. Dendritic cells may be recognized by function, or by phenotype, particularly by cell surface phenotype. These cells are characterized by their distinctive morphology having veil-like projections on the cell surface, intermediate to high levels of surface HLA-class II expression and ability to present antigen to T cells, particularly to naive T cells (See Steinman R, et al., Ann. Rev. Immunol. 1991; 9:271-196.). Typically, cell surface phenotype of DCs include CD1a+, CD4+, CD86+, or HLA-DR. The term DCs encompasses both immature and mature DCs.

According to specific embodiments, the immune cells comprise granulocytes.

As used herein, the term "granulocytes" refer to polymorphonuclear leukocytes characterized by the presence of granules in their cytoplasm.

According to specific embodiments, the granulocytes comprise neutrophils.

According to specific embodiments, the granulocytes comprise mast-cells.

According to specific embodiments the immune cells comprise T cells.

As used herein, the term "T cells" refers to a differentiated lymphocyte with a CD3+, T cell receptor (TCR)+ having either CD4+ or CD8+ phenotype. The T cell may be either an effector or a regulatory T cell.

As used herein, the term "effector T cells" refers to a T cell that activates or directs other immune cells e.g. by producing cytokines or has a cytotoxic activity e.g., CD4+, Th1/Th2, CD8+ cytotoxic T lymphocyte.

As used herein, the term "regulatory T cell" or "Treg" refers to a T cell that negatively regulates the activation of other T cells, including effector T cells, as well as innate immune system cells. Treg cells are characterized by sustained suppression of effector T cell responses. According to a specific embodiment, the Treg is a CD4+CD25+Foxp3+ T cell.

According to specific embodiments, the T cells are CD4+ T cells.

According to other specific embodiments, the T cells are CD8+ T cells.

According to specific embodiments, the T cells are memory T cells. Non-limiting examples of memory T cells include effector memory CD4+ T cells with a CD3+/CD4+/CD45RA−/CCR7− phenotype, central memory CD4+ T cells with a CD3+/CD4+/CD45RA−/CCR7+ phenotype, effector memory CD8+ T cells with a CD3+/CD8+ CD45RA−/CCR7-phenotype and central memory CD8+ T cells with a CD3+/CD8+CD45RA−/CCR7+ phenotype.

According to specific embodiments, the T cells comprise engineered T cells transduced with a nucleic acid sequence encoding an expression product of interest.

According to specific embodiments, the expression product of interest is a T cell receptor (TCR) or a chimeric antigen receptor (CAR).

As used herein the phrase "transduced with a nucleic acid sequence encoding a TCR" or "transducing with a nucleic acid sequence encoding a TCR" refers to cloning of variable co- and β-chains from T cells with specificity against a desired antigen presented in the context of MHC. Methods of transducing with a TCR are known in the art and are disclosed e.g. in Nicholson et al. Adv Hematol. 2012; 2012:404081; Wang and Rivibre Cancer Gene Ther. 2015 March; 22(2):85-94); and Lamers et al, Cancer Gene Therapy (2002) 9, 613-623.

As used herein, the phrase "transduced with a nucleic acid sequence encoding a CAR" or "transducing with a nucleic acid sequence encoding a CAR" refers to cloning of a nucleic acid sequence encoding a chimeric antigen receptor (CAR), wherein the CAR comprises an antigen recognition moiety and a T-cell activation moiety. A chimeric antigen receptor (CAR) is an artificially constructed hybrid protein or polypeptide containing an antigen binding domain of an antibody (e.g., a single chain variable fragment (scFv)) linked to T-cell signaling or T-cell activation domains. Method of transducing with a CAR are known in the art and are disclosed e.g. in Davila et al. Oncoimmunology. 2012 Dec. 1; 1(9):1577-1583; Wang and Rivibre Cancer Gene Ther. 2015 March; 22(2):85-94); Maus et al. Blood. 2014 Apr. 24; 123(17):2625-35; Porter D L The New England journal of medicine. 2011, 365(8):725-733; Jackson H J, Nat Rev Clin Oncol. 2016; 13(6):370-383; and Globerson-Levin et al. Mol Ther. 2014; 22(5):1029-1038.

According to specific embodiments, the immune cells comprise B cells.

As used herein the term "B cells" refers to a lymphocyte with a B cell receptor (BCR)+, CD19+ and or B220+ phenotype. B cells are characterized by their ability to bind a specific antigen and elicit a humoral response.

According to specific embodiments, the immune cells comprise NK cells.

As used herein the term "NK cells" refers to differentiated lymphocytes with a CD16+CD56+ and/or CD57+ TCR− phenotype. NK are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

According to specific embodiments, the immune cells comprise NKT cells.

As used herein the term "NKT cells" refers to a specialized population of T cells that express a semi-invariant αβ T-cell receptor, but also express a variety of molecular markers that are typically associated with NK cells, such as NK1.1. NKT cells include NK1.1+ and NK1.1−, as well as CD4+, CD4−, CD8+ and CD8− cells. The TCR on NKT cells is unique in that it recognizes glycolipid antigens presented by the MHC I-like molecule CD1d. NKT cells can have either protective or deleterious effects due to their abilities to produce cytokines that promote either inflammation or immune tolerance.

According to specific embodiments, the immune cells are obtained from a healthy subject.

According to specific embodiments, the immune cells are obtained from a subject suffering from a pathology (e.g. cancer).

According to specific embodiments, the activating is in the presence of cells expressing CD47 or exogenous CD47.

According to specific embodiments, the activating is in the presence of exogenous CD47, According to specific embodiments, the exogenous CD47 is soluble.

According to other specific embodiments, the exogenous CD47 is immobilized to a solid support.

According to specific embodiments, the activating is in the presence of cells expressing CD47.

According to specific embodiments, the cells expressing the CD47 comprise pathologic (diseased) cells.

According to specific embodiments, the cells expressing the CD47 comprise cancer cells.

According to specific embodiments, the activating is in the presence of a stimulatory agent capable of at least transmitting a primary activating signal [e.g. ligation of the T-Cell Receptor (TCR) with the Major Histocompatibility Complex (MHC)/peptide complex on the Antigen Presenting Cell (APC)] resulting in cellular proliferation, maturation, cytokine production, phagocytosis and/or induction of regulatory or effector functions of the immune cell. According to specific embodiments, the stimulator agent can also transmit a secondary co-stimulatory signal.

Methods of determining the amount of the stimulatory agent and the ratio between the stimulatory agent and the immune cells are well within the capabilities of the skilled in the art and thus are not specified herein.

The stimulatory agent can activate the immune cells in an antigen-dependent or -independent (i.e. polyclonal) manner.

According to specific embodiments, stimulatory agent comprises an antigen non-specific stimulator.

Non-specific stimulators are known to the skilled in the art. Thus, as a non-limiting example, when the immune cells comprise T cells, antigen non-specific stimulator can be an agent capable of binding to a T cell surface structure and induce the polyclonal stimulation of the T cell, such as but not limited to anti-CD3 antibody in combination with a co-stimulatory protein such as anti-CD28 antibody. Other non-limiting examples include anti-CD2, anti-CD137, anti-CD134, Notch-ligands, e.g. Delta-like 1/4, Jagged1/2 either alone or in various combinations with anti-CD3. Other agents that can induce polyclonal stimulation of T cells include, but not limited to mitogens, PHA, PMA-ionomycin, CEB and CytoStim (Miltenyi Biotech). According to specific embodiments, the antigen non-specific stimulator comprises anti-CD3 and anti-CD28 antibodies. According to specific embodiments, the T cell stimulator comprises anti-CD3 and anti-CD28 coated beads, such as the CD3CD28 MACSiBeads obtained from Miltenyi Biotec.

According to specific embodiments, the stimulatory agent comprises an antigen-specific stimulator.

Non-limiting examples of antigen specific T cell stimulators include an antigen-loaded antigen presenting cell [APC, e.g. dendritic cell] and peptide loaded recombinant MHC. Thus, for example, a T cells stimulator can be a dendritic cell preloaded with a desired antigen (e.g. a tumor antigen) or transfected with mRNA coding for the desired antigen.

According to specific embodiments, the antigen is a cancer antigen.

As used herein, the term "cancer antigen" refers to an antigen is overexpressed or solely expressed by a cancerous cell as compared to a non-cancerous cell. A cancer antigen may be a known cancer antigen or a new specific antigen that develops in a cancer cell (i.e. neoantigens).

Non-limiting examples for known cancer antigens include MAGE-AI, MAGE-A2, MAGE-A3, MAGE-A4, MAGE-AS, MAGE-A6, MAGE-A7, MAGE-AS, MAGE-A9, MAGE-AIO, MAGE-All, MAGE-A12, GAGE-I, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), MAGE-C1/CT7, MAGE-C2, NY-ESO-1, LAGE-1, SSX-1, SSX-2(HOM-MEL-40), SSX-3, SSX-4, SSX-5, SCP-1 and XAGE, melanocyte differentiation antigens, p53, ras, CEA, MUCI, PMSA, PSA, tyrosinase, Melan-A, MART-I, gplOO, gp75, alphaactinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-All, hsp70-2, KIAA0205, Mart2, Mum-2, and 3, neo-PAP, myosin class I, OS-9, pml-RAR alpha fusion protein, PTPRK, K-ras, N-ras, Triosephosphate isomerase, GnTV, Herv-K-mel, NA-88, SP17, and TRP2-Int2, (MART-I), E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, plSOerbB-3, c-met, nm-23Hl, PSA, TAG-72-4, CA 19-9, CA 72-4, CAM 17.1, NuMa, K-ras, alpha.-fetoprotein, 13HCG, BCA225, BTAA, CA 125, CA 15-3 (CA 27.29\BCAA), CA 195, CA 242, CA-50, CAM43, CD68\KP1, C0-029, FGF-5, 0250, Ga733 (EpCAM), HTgp-175, M344, MA-50, MG7-Ag, MOV18, NB\170K, NYCO-I, RCASI, SDCCAG16, TA-90 (Mac-2 binding protein\cyclophilin C-associated protein), TAAL6, TAG72, TLP, TPS, tyrosinase related proteins, TRP-1, or TRP-2.

Other tumor antigens that may be expressed are well-known in the art (see for example WO00/20581; Cancer Vaccines and Immunotherapy (2000) Eds Stern, Beverley and Carroll, Cambridge University Press, Cambridge). The sequences of these tumor antigens are readily available from public databases but are also found in WO 1992/020356 AI, WO 1994/005304 AI, WO 1994/023031 AI, WO 1995/020974 AI, WO 1995/023874 AI & WO 1996/026214 AI.

Alternatively, or additionally, a tumor antigen may be identified using cancer cells obtained from the subject by e.g. biopsy.

Thus, according to specific embodiments, the stimulatory agent comprises a cancer cell.

According to specific embodiments, the activating is in the presence of an anti-cancer agent.

According to specific embodiments, the immune cells are purified following the activation.

Thus, the present invention also contemplated isolated immune cells obtainable according to the methods of the present invention.

According to specific embodiments, the immune cells used and/or obtained according to the present invention can be freshly isolated, stored e.g., cryopreserved (i.e. frozen) at e.g. liquid nitrogen temperature at any stage for long periods of time (e.g., months, years) for future use; and cell lines.

Methods of cryopreservation are commonly known by one of ordinary skill in the art and are disclosed e.g. in International Patent Application Publication Nos. WO2007054160 and WO 2001039594 and US Patent Application Publication No. US20120149108.

According to specific embodiments, the cells obtained according to the present invention can be stored in a cell bank or a depository or storage facility.

Consequently, the present teachings further suggest the use of the isolated immune cells and the methods of the present invention as, but not limited to, a source for adoptive immune cells therapies for diseases that can benefit from activating immune cells e.g. a hyper-proliferative disease; a disease associated with immune suppression and infections.

Thus, according to specific embodiments, method of the present invention comprise adoptively transferring the immune cells following said activating to a subject in need thereof.

According to specific embodiments, there is provided the immune cells obtainable according to the methods of the present invention are for use in adoptive cell therapy.

The cells used according to specific embodiments of the present invention may be autologous or non-autologous; they can be syngeneic or non-syngeneic: allogeneic or xenogeneic to the subject; each possibility represents a separate embodiment of the present invention.

The present teachings also contemplates the use of the compositions of the present invention (e.g. the fusion protein, a polynucleotide or nucleic acid construct encoding same or a host cell expressing same) in methods of treating a disease that can benefit from activating immune cells.

Thus, according to another aspect of the present invention, there is provided a method of treating a disease that can benefit from activating immune cells comprising administering to a subject in need thereof the SIRPα-41BBL fusion protein, a polynucleotide or nucleic acid construct encoding same or a host cell encoding same.

According to another aspect of the present invention, there is provided the SIRPα-41BBL fusion protein, a polynucleotide or nucleic acid construct encoding same or a host cell encoding same for use in the treatment of a disease that can benefit from activating immune cells.

The term "treating" or "treatment" refers to inhibiting, preventing or arresting the development of a pathology (disease, disorder or medical condition) and/or causing the reduction, remission, or regression of a pathology or a symptom of a pathology. Those of skill in the art will understand that various methodologies and assays can be used to assess the development of a pathology, and similarly, various methodologies and assays may be used to assess the reduction, remission or regression of a pathology.

As used herein, the term "subject" includes mammals, e.g., human beings at any age and of any gender. According to specific embodiments, the term "subject" refers to a subject who suffers from the pathology (disease, disorder or medical condition). According to specific embodiments, this term encompasses individuals who are at risk to develop the pathology.

According to specific embodiments, the subject is afflicted with a disease associated with cells expressing CD47.

According to specific embodiments, diseases cells of the subject express CD47.

As used herein the phrase "a disease that can benefit from activating immune cells" refers to diseases in which the subject's immune response activity may be sufficient to at least ameliorate symptoms of the disease or delay onset of symptoms, however for any reason the activity of the subject's immune response in doing so is less than optimal.

Non-limiting examples of diseases that can benefit from activating immune cells include hyper-proliferative diseases, diseases associated with immune suppression, immunosuppression caused by medication (e.g. mTOR inhibitors, calcineurin inhibitor, steroids) and infections.

According to specific embodiments, the disease comprises a hyper-proliferative disease.

According to specific embodiments, the hyper-proliferative disease comprises sclerosis or fibrosis, Idiopathic pulmonary fibrosis, psoriasis, systemic sclerosis/scleroderma, primary biliary cholangitis, primary sclerosing cholangitis, liver fibrosis, prevention of radiation-induced pulmonary fibrosis, myelofibrosis or retroperitoneal fibrosis.

According to other specific embodiments, the hyper-proliferative disease comprises cancer.

Thus, according to another aspect of the present invention, there is provided a method of treating cancer comprising administering the SIRPα-41BBL fusion protein to a subject in need thereof.

As used herein, the term cancer encompasses both malignant and pre-malignant cancers.

With regard to pre-malignant or benign forms of cancer, optionally the compositions and methods thereof may be applied for halting the progression of the pre-malignant cancer to a malignant form.

Cancers which can be treated by the methods of some embodiments of the invention can be any solid or non-solid cancer and/or cancer metastasis.

According to specific embodiments, the cancer comprises malignant cancer.

Examples of cancer include but are not limited to, carcinoma, lymphoma, blastoma, sarcoma, and leukemia. More particular examples of such cancers include squamous cell cancer, lung cancer (including small-cell lung cancer, non-small-cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); Burkitt lymphoma, Diffused large B cell lymphoma (DLBCL), small lymphocytic (SL) NHL; intermediate grade/follicular NHL; intermediate grade diffuse NHL; high grade immunoblastic NHL; high grade lymphoblastic NHL; high-grade small non-cleaved cell NHL; bulky disease NHL; mantle cell lymphoma; AIDS-related lymphoma; and Waldenstrom's Macroglobulinemia); T cell lymphoma, Hodgkin lymphoma, chronic lymphocytic leukemia (CLL); acute lymphoblastic leukemia (ALL); Acute myeloid leukemia (AML), Acute promyelocytic leukemia (APL), Hairy cell leukemia; chronic myeloblastic leukemia (CML); and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. The cancerous conditions amenable for treatment of the invention include metastatic cancers.

According to specific embodiments, the cancer comprises pre-malignant cancer.

Pre-malignant cancers (or pre-cancers) are well characterized and known in the art (refer, for example, to Berman J J. and Henson D E., 2003. Classifying the precancers: a metadata approach. BMC Med Inform Decis Mak. 3:8). Classes of pre-malignant cancers amenable to treatment via the method of the invention include acquired small or microscopic pre-malignant cancers, acquired large lesions with nuclear atypia, precursor lesions occurring with inherited hyperplastic syndromes that progress to cancer, and acquired diffuse hyperplasias and diffuse metaplasias. Examples of small or microscopic pre-malignant cancers include HGSIL (High grade squamous intraepithelial lesion of uterine cervix), AIN (anal intraepithelial neoplasia), dysplasia of vocal cord, aberrant crypts (of colon), PIN (prostatic intraepithelial neoplasia).

Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma. Examples of precursor lesions occurring with inherited hyperplastic syndromes that progress to cancer include atypical mole syndrome, C cell adenomatosis and MEA. Examples of acquired diffuse hyperplasias and diffuse metaplasias include AIDS, atypical lymphoid hyperplasia, Paget's disease of bone, post-transplant lymphoproliferative disease and ulcerative colitis.

In some embodiments of the invention, the diseases to be treated by a fusion protein comprising SIRPα or the ECD thereof and 41BBL or ECD thereof, such as for example, SIRPα-G-41BBL are: Leukemia, Chronic myelomonocytic leukemia (CMML), Chronic myelogenous leukemia (CML), Acute myeloid leukemia (AML), Non Hodgkin lymphoma (NHL), Diffuse Large B Cell Lymphoma (DLBCL), B cell Chronic Lymphocytic Leukemia (B-CLL), Mantle Cell Lymphoma (MCL), Follicular Lymphoma (FL), Marginal Zone Lymphoma (MZL), Pre-B acute lymphoblastic leukemia (pre-B ALL), Leiomyosarcoma, Ovarian cancer, Breast cancer, Colon cancer, Bladder cancer, Glioblastoma, Hepatocellular carcinoma, Prostate cancer, Acute lymphoblastic leukemia (ALL), Multiple Myeloma, Non-small-cell lung carcinoma (NSCLC), Colorectal cancer, Melanoma, Head and Neck Cancer, Marginal Zone B-cell Lymphoma, Pancreatic Ductal Adenocarcinoma, Brain cancer According to some embodiments of the invention the indications the diseases to be treated by a fusion protein comprising SIRPα or the ECD thereof and 41BBL or ECD thereof, such as for example, SIRPα-G-41BBL are: Acute myeloid leukemia, Bladder Cancer, Breast Cancer, chronic lymphocytic leukemia, Chronic myelogenous leukemia, Colorectal cancer, Diffuse large B-cell lymphoma, Epithelial Ovarian Cancer, Epithelial Tumor, Fallopian Tube Cancer, Follicular Lymphoma, Glioblastoma multiform, Hepatocellular carcinoma, Head and Neck Cancer, Leukemia, Lymphoma, Mantle Cell Lymphoma, Melanoma, Mesothelioma, Multiple Myeloma, Nasopharyngeal Cancer, Non Hodgkin lymphoma, Non-small-cell lung carcinoma, Ovarian Cancer, Prostate Cancer, Renal cell carcinoma.

According to specific embodiments, the cancer is selected from the group consisting of lymphoma, leukemia, colon cancer, pancreatic cancer, ovarian cancer, lung cancer and squamous cell carcinoma.

According to specific embodiments, the cancer is selected from the group consisting of lymphoma, carcinoma and leukemia.

According to specific embodiments, the cancer is colon carcinoma.

According to specific embodiments, the cancer is ovarian carcinoma.

According to specific embodiments, the cancer is lung carcinoma.

According to specific embodiments, the cancer is head and neck carcinoma.

According to specific embodiments, the cancer is leukemia.

According to specific embodiments, the leukemia is selected from the group consisting of acute nonlymphocytic leukemia, chronic lymphocytic leukemia, acute granulocytic leukemia, chronic granulocytic leukemia, acute promyelocytic leukemia, adult T-cellleukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, ( )ross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

According to specific embodiments, the leukemia is promyelocytic leukemia, acute myeloid leukemia or chronic myelogenous leukemia.

According to specific embodiments, the cancer is lymphoma.

According to specific embodiments, the lymphoma is B cell lymphoma

According to specific embodiments, the lymphoma is T cell lymphoma.

According to other specific embodiments, the lymphoma is Hodgkins lymphoma.

According to specific embodiments, the lymphoma is non-Hodgkins lymphoma.

According to specific embodiments, the non-Hodgkin's Lymphoma is a selected from the group consisting of aggressive NHL, transformed NHL, indolent NHL, relapsed NHL, refractory NHL, low grade non-Hodgkin's Lymphoma, follicular lymphoma, large cell lymphoma, B-cell lymphoma, T-cell lymphoma, Mantle cell lymphoma, Burkitt's lymphoma, NK cell lymphoma, diffuse large B-cell lymphoma, acute lymphoblastic lymphoma, and cutaneous T cell cancer, including mycosos fungoides/Sezry syndrome.

According to specific embodiments, the cancer is multiple myeloma.

According to at least some embodiments, the multiple myeloma is selected from the group consisting of multiple myeloma cancers which produce light chains of kappa-type and/or light chains of lambda-type; aggressive multiple myeloma, including primary plasma cell leukemia (PCL); benign plasma cell disorders such as MGUS (monoclonal gammopathy of undetermined significance), Waldenstrom's macroglobulinemia (WM, also known as lymphoplasmacytic lymphoma) which may proceed to multiple myeloma; smoldering multiple myeloma (SMM), indolent multiple myeloma, premalignant forms of multiple myeloma which may also proceed to multiple myeloma; primary amyloidosis.

A Suggested Mode of Action of SIRPα-41BBL

In one embodiment of the invention, the chimera SIRPα-41BBL can be used for treating of cancer via the following possible mode-of-action:

- Due to the relatively high expression of CD47 on the surface of tumor cells and in the tumor micro-environment, the SIRPα moiety of the SIRPα-41BBL chimera will target the molecule to tumor and metastasis sites, and will bind the chimera to CD47 within the tumor micro-environment.
- Targeting the chimera to the tumor cells or/and tumor micro-environment will facilitate an increase in SIRPα-41BBL concertation in the tumor micro-environment and subsequent oligomerization of the 4-1BBL moiety of the chimera at the tumor site. Since oligomerization of 4-1BBL is a necessary step for 4-1BB signaling, this 4-1BBL binding and oligomerization will deliver a 4-1BB co-stimulatory signal that will promote activation of T-cells, B cells, NK cells, especially Tumor-Infiltrating Lymphocytes (TILs), and other immune cells at the tumor site, to kill cancer cells.
- In addition to the 41BBL-41BB co-stimulatory signal, the binding of the chimera's SIRPα moiety to CD47 in the tumor site will compete with the endogenous SIRPα expressed on macrophages and dendritic cells, thus, removing the inhibition on these cells and further contributing to the phagocytosis of tumor cells and to activation of dendritic cells and T cells in the tumor micro-environment.

The above activities of SIRPA-41BBL are anticipated to lead to a synergistic effect on the activation of TILs, dendritic cells and macrophages within the tumor micro-environment, which is expected to be more specific and robust effect as compared to the effect of each peptide or ECD thereof separately, as well as when using the two different peptides or ECD thereof in combination.

Thus, according to specific embodiments, the cancer is defined by the presence of tumors that have tumor-infiltrating lymphocytes (TILs) in the tumor micro-environment and/or tumors with expression of CD47 in the tumor micro-environment.

According to specific embodiments, the cancer is defined by the presence of tumors that have tumor-infiltrating lymphocytes (TILs) in the tumor micro-environment and/or tumors with a relatively high expression of CD47 in the tumor micro-environment.

According to specific embodiments, cells of the cancer express CD47.

According to specific embodiments, the disease comprises a disease associated with immune suppression or immunosuppression caused by medication (e.g. mTOR inhibitors, calcineurin inhibitor, steroids).

According to specific embodiments, the disease comprises HIV, Measles, influenza, LCCM, RSV, Human Rhinoviruses, EBV, CMV, Parvo viruses.

According to specific embodiments, the disease comprises an infection.

As used herein, the term "infection" of "infectious disease" refers to a disease induced by a pathogen. Specific examples of pathogens include, viral pathogens, bacterial pathogens e.g., intracellular mycobacterial pathogens (such as, for example, *Mycobacterium tuberculosis*), intracellular bacterial pathogens (such as, for example, *Listeria monocytogenes*), or intracellular protozoan pathogens (such as, for example, *Leishmania* and *Trypanosoma*).

Specific types of viral pathogens causing infectious diseases treatable according to the teachings of the present invention include, but are not limited to, retroviruses, circoviruses, parvoviruses, papovaviruses, adenoviruses, herpesviruses, iridoviruses, poxviruses, hepadnaviruses, picornaviruses, caliciviruses, togaviruses, flaviviruses, reoviruses, orthomyxoviruses, paramyxoviruses, rhabdoviruses, bunyaviruses, coronaviruses, arenaviruses, and filoviruses.

Specific examples of viral infections which may be treated according to the teachings of the present invention include, but are not limited to, human immunodeficiency virus (HIV)-induced acquired immunodeficiency syndrome (AIDS), influenza, rhinoviral infection, viral meningitis, Epstein-Barr virus (EBV) infection, hepatitis A, B or C virus infection, measles, papilloma virus infection/warts, cytomegalovirus (CMV) infection, Herpes simplex virus infection, yellow fever, Ebola virus infection, rabies, etc.

According to specific embodiments, the compositions of the present invention (e.g. SIRPα-41BBL fusion protein, polynucleotide or nucleic acid construct encoding same and/or host-cell expressing same) can be administered to a subject in combination with other established or experimental therapeutic regimen to treat a disease that can benefit from activating immune cells (e.g. cancer) including, but not limited to analgesics, chemotherapeutic agents, radiotherapeutic agents, cytotoxic therapies (conditioning), hormonal therapy, antibodies and other treatment regimens (e.g., surgery) which are well known in the art.

According to specific embodiments, the compositions of the present invention (e.g. SIRPα-41BBL fusion protein, polynucleotide or nucleic acid construct encoding same and/or host-cell expressing same) can be administered to a subject in combination with adoptive cell transplantation such as, but not limited to transplantation of bone marrow cells, hematopoietic stem cells, PBMCs, cord blood stem cells and/or induced pluripotent stem cells.

According to specific embodiments, the therapeutic agent administered in combination with the composition of the invention comprises an anti-cancer agent.

Thus, according to another aspect of the present invention, there is provided a method of treating cancer comprising administering to a subject in need thereof an anti-cancer agent; and a SIRPα-41BBL fusion protein, a polynucleotide encoding same, a nucleic acid construct encoding same or a host cell expressing same.

Anti-cancer agents that can be use with specific embodiments of the invention include, but are not limited to the anti-cancer drugs Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-

1263, of Goodman and Gilman's "The Pharmacological Basis of Therapeutics", Eighth Edition, 1990, McGraw-Hill, Inc. (Health Professions Division).

According to specific embodiments, the anti-cancer agent comprises an antibody.

According to specific embodiments, the antibody is selected from the group consisting of rituximab, cetuximab, trastuzumab, edrecolomab, alemtuzumab, gemtuzumab, ibritumomab, panitumumab, Belimumab, Bevacizumab, Bivatuzumab mertansine, Blinatumomab, Blontuvetmab, Brentuximab vedotin, Catumaxomab, Cixutumumab, Daclizumab, Adalimumab, Bezlotoxumab, Certolizumab pegol, Citatuzumab bogatox, Daratumumab, Dinutuximab, Elotuzumab, Ertumaxomab, Etaracizumab, Gemtuzumab ozogamicin, Girentuximab, Necitumumab, Obinutuzumab, Ofatumumab, Pertuzumab, Ramucirumab, Siltuximab, Tositumomab, Trastuzumab and ipilimumab.

According to specific embodiments, the antibody is selected from the group consisting of rituximab and cetuximab.

According to specific embodiments, the therapeutic agent administered in combination with the composition of the invention comprises an anti-infection agent (e.g. antibiotics and anti-viral agents)

According to specific embodiments, the therapeutic agent administered in combination with the composition of the invention comprises an immune suppressor agent (e.g. GCSF and other bone marrow stimulators, steroids)

According to specific embodiments the combination therapy has an additive effect.

According to specific embodiments, the combination therapy has a synergistic effect.

According to another aspect of the present invention there is provided an article of manufacture identified for the treatment of a disease that can benefit from activating immune cells comprising a packaging material packaging a therapeutic agent for treating said disease; and a SIRPα-41BBL fusion protein, a polynucleotide encoding same, a nucleic acid construct encoding same or a host cell expressing same.

According to specific embodiments, the therapeutic agent for treating said disease; and a SIRPα-41BBL fusion protein, a polynucleotide encoding same, a nucleic acid construct encoding same or a host cell expressing same are packages in separate containers.

According to specific embodiments, the therapeutic agent for treating said disease; and a SIRPα-41BBL fusion protein, a polynucleotide or a nucleic acid encoding same, a nucleic acid construct encoding same or a host cell expressing same are packages in a co-formulation.

As used herein, in one embodiment, the term "amino acid derivative" or "derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —NH-G(Sc)-C(0)-Q or —OC(O)G($S_c$)-Q, wherein Q is —SR, —NRR or alkoxyl, R is hydrogen or alkyl, $S_c$ is a side chain of a naturally occurring or non-naturally occurring amino acid and G is $C_1$-$C_2$ alkyl. In certain embodiments, G is Ci alkyl and Sc is selected from the group consisting of hydrogen, alkyl, heteroalkyl, arylalkyl and heteroarylalkyl.

As used herein, in one embodiment, the term "peptide", "polypeptide" or "protein" which are interchangeably used herein may be derived from a natural biological source, synthesized, or produced by recombinant technology. It may be generated in any manner known in the art of peptide or protein synthesis, including by chemical synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965. One or more of the amino acids may be modified, for example, by the addition of a chemical entity such as a carbohydrate group, a phosphate group, a farnesyl group, an isofamesyt group, a fatty acid group, an acyl group (e.g., acetyl group), a linker for conjugation, functionalization, or other known protecting/blocking groups. Modifications to the peptide or protein can be introduced by gene synthesis, site-directed (e.g., PCR based) or random mutagenesis (e.g., EMS) by exonuclease deletion, by chemical modification, or by fusion of polynucleotide sequences encoding a heterologous domain or binding protein, for example.

As used herein, in one embodiment, the term "peptide," may be fragments, derivatives, analogs, or variants of the foregoing peptides, and any combination thereof. Fragments of peptides, as that term or phrase is used herein, include proteolytic fragments, as well as deletion fragments. Variants of peptides include fragments and peptides with altered amino acid sequences due to amino acid substitutions, deletions, or insertions.

Variants may occur naturally or be non-naturally occurring. Examples include fusion proteins, peptides having one or more residues chemically derivatized by reaction of a functional side group, and peptides that contain one or more naturally occurring amino acid derivatives of the twenty standard amino acids. These modifications may also include the incorporation of D-amino acids, or other non-encoded amino-acids. In one embodiment, none of the modifications should substantially interfere with the desired biological activity of the peptide, fragment thereof. In another embodiment, modifications may alter a characteristic of the peptide, fragment thereof, for instance stability or half-life, without interfering with the desired biological activity of the peptide, fragment thereof. In one embodiment, as used herein the terms "peptide" and "protein" may be used interchangeably having all the same meanings and qualities.

In one embodiment, to facilitate recovery, the expressed coding sequence can be engineered to encode the peptide of the present invention and fused cleavable moiety. In one embodiment, a fusion protein can be designed so that the peptide can be readily isolated by affinity chromatography; e.g., by immobilization on a column specific for the cleavable moiety. In one embodiment, a cleavage site is engineered between the peptide and the cleavable moiety and the peptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, each of the peptides that forms the fusion protein (also termed here "the peptide") of the present invention can also be synthesized using in vitro expression systems. In one embodiment, in vitro synthesis methods are well known in the art and the components of the system are commercially available.

In one embodiment, production of a peptide of this invention is using recombinant DNA technology. A "recombinant" peptide, or protein refers to a peptide, or protein produced by recombinant DNA techniques; i.e., produced from cells transformed by an exogenous DNA construct encoding the desired peptide or protein.

Thus, according to another aspect of the present invention, there is provided an isolated polynucleotide comprising a nucleic acid sequence encoding any of the above described fusion proteins.

According to specific embodiments, the polynucleotide comprises SEQ ID NO: 8.

According to specific embodiments, the polynucleotide consists of SEQ ID NO: 8.

According to specific embodiments, the polynucleotide is least about 70%, 75%, 80%, 85%, 90%, 95%, 96%, 97%, 98% or 99% homologous to the nucleic sequence as set forth in SEQ ID No. 8.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

To express exogenous SIRPα-41BBL in mammalian cells, a polynucleotide sequence encoding SIRPα-41BBL is preferably ligated into a nucleic acid construct suitable for mammalian cell expression. Such a nucleic acid construct includes a promoter sequence for directing transcription of the polynucleotide sequence in the cell in a constitutive or inducible manner.

Hence, according to specific embodiments, there is provided nucleic acid construct comprising the polynucleotide and a regulatory element for directing expression of said polynucleotide in a host cell.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the peptide from a host cell in which it is placed. Preferably the signal sequence for this purpose is a mammalian signal sequence or the signal sequence of the polypeptide variants of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of SIRPα-41BBL mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types.

Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

It will be appreciated that the individual elements comprised in the expression vector can be arranged in a variety of configurations. For example, enhancer elements, promoters and the like, and even the polynucleotide sequence(s) encoding a SIRPα-41BBL can be arranged in a "head-to-tail" configuration, may be present as an inverted complement, or in a complementary configuration, as an anti-parallel strand. While such variety of configuration is more likely to occur with non-coding elements of the expression vector, alternative configurations of the coding sequence within the expression vector are also envisioned.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p205. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus Autographa californica nucleopolyhedrovirus (AcMNPV) as described in Liang C Y et al., 2004 (Arch Virol. 149: 51-60).

Recombinant viral vectors are useful for in vivo expression of SIRPα-41BBL since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of some embodiments of the invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

As mentioned, other than containing the necessary elements for the transcription and translation of the inserted coding sequence, the expression construct of some embodiments of the invention can also include sequences engineered to enhance stability, production, purification, yield or toxicity of the expressed peptide. For example, the expression of a fusion protein or a cleavable fusion protein comprising the SIRPα-41BBL protein of some embodiments of the invention and a heterologous protein can be engineered. Such a fusion protein can be designed so that the fusion protein can be readily isolated by affinity chromatography; e.g., by immobilization on a column specific for the heterologous protein. Where a cleavage site is engineered between the SIRPα-41BBL protein and the heterologous protein, the SIRPα-41BBL protein can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

The present invention also contemplates cells comprising the composition described herein.

Thus, according to specific embodiments, there is provided a host cell comprising the SIRPα-41BBL fusion protein, the polynucleotide encoding same or the nucleic acid construct encoding same.

As mentioned hereinabove, a variety of prokaryotic or eukaryotic cells can be used as host-expression systems to express the polypeptides of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

Examples of bacterial constructs include the pET series of E. coli expression vectors (Studier et al. (1990) Methods in Enzymol. 185:60-89).

Examples of eukaryotic cells which may be used along with the teachings of the invention include but are not limited to, mammalian cells, fungal cells, yeast cells, insect cells, algal cells or plant cells.

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Other expression systems such as insects and mammalian host cell systems which are well known in the art can also be used by some embodiments of the invention.

According to specific embodiments the cell is a mammalian cell.

According to specific embodiment, the cell is a human cell.

According to a specific embodiment, the cell is a cell line.

According to another specific embodiment, the cell is a primary cell.

The cell may be derived from a suitable tissue including but not limited to blood, muscle, nerve, brain, heart, lung, liver, pancreas, spleen, thymus, esophagus, stomach, intestine, kidney, testis, ovary, hair, skin, bone, breast, uterus, bladder, spinal cord, or various kinds of body fluids. The cells may be derived from any developmental stage including embryo, fetal and adult stages, as well as developmental origin i.e., ectodermal, mesodermal, and endodermal origin.

Non limiting examples of mammalian cells include monkey kidney CV1 line transformed by SV40 (COS, e.g. COS-7, ATCC CRL 1651); human embryonic kidney line (HEK293 or HEK293 cells subcloned for growth in suspension culture, Graham et al., J. Gen Virol., 36:59 1977); baby hamster kidney cells (BHK, ATCC CCL 10); mouse sertoli cells (TM4, Mather, Biol. Reprod., 23:243-251 1980); monkey kidney cells (CV1 ATCC CCL 70); African green monkey kidney cells (VERO-76, ATCC CRL-1587); human cervical carcinoma cells (HeLa, ATCC CCL 2); NIH3T3, Jurkat, canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 1982); MRC 5 cells; FS4 cells; and a human hepatoma line (Hep G2), PER.C6, K562, and Chinese hamster ovary cells (CHO).

According to some embodiments of the invention, the mammalian cell is selected from the group consisting of a Chinese Hamster Ovary (CHO), HEK293, PER.C6, HT1080, NS0, Sp2/0, BHK, Namalwa, COS, HeLa and Vero cell.

According to some embodiments of the invention, the host cell comprises a Chinese Hamster Ovary (CHO), PER.C6 and 293 (e.g., Expi293F) cell.

According to another aspect of the present invention, there is provided a method of producing a SIRPα-41BBL fusion protein, the method comprising expressing in a host cell the polynucleotide or the nucleic acid construct described herein.

According to specific embodiments, the methods comprising isolating the fusion protein.

According to specific embodiments, recovery of the recombinant polypeptide is effected following an appropriate time in culture. The phrase "recovering the recombinant polypeptide" refers to collecting the whole fermentation medium containing the polypeptide and need not imply additional steps of separation or purification. Notwithstanding the above, polypeptides of some embodiments of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, mix mode chromatography, metal affinity chromatography, Lectins affinity chromatography, chromatofocusing and differential solubilization.

In some embodiments, the recombinant peptides, fragments thereof or peptides are synthesized and purified; their therapeutic efficacy can be assayed either in vivo or in vitro. In one embodiment, the activities of the recombinant fragments or peptides of the present invention can be ascertained using various assays including cell viability, survival of transgenic mice, and expression of megakaryocytic and lymphoid RNA markers.

In one embodiment, a peptide of this invention comprises at least 3 amino acids. In another embodiment, a peptide comprises at least 5 amino acids. In another embodiment, a peptide comprises at least 10 amino acids. In another embodiment, a peptide comprises at least 20 amino acids. In another embodiment, a peptide comprises at least 25 amino acids. In other embodiments, a peptide comprises at least 30 amino acids or at least 50 amino acids or 75 amino acids, or 100 amino acids, or 125 amino acids, or 150 amino acids, or 200 amino acids, or 250 amino acids or 300 amino acids or 350 amino acids or 400 amino acids. In one embodiment, a peptide of this invention consists essentially of at least 5 amino acids. In another embodiment, a peptide consists essentially of at least 10 amino acids. In other embodiments, a peptide consists essentially of at least 30 amino acids or at least 50 amino acids or 75 amino acids, or 100 amino acids, or 125 amino acids, or 150 amino acids, or 200 amino acids, or 250 amino acids or 300 amino acids or 350 amino acids or 400 amino acids. In one embodiment, a peptide of this invention consists of at least 5 amino acids. In another embodiment, a peptide consists of at least 10 amino acids. In other embodiments, a peptide consists of at least 30 amino acids or at least 50 amino acids or 75 amino acids, or 100 amino acids, or 125 amino acids, or 150 amino acids, or 200 amino acids, or 250 amino acids or 300 amino acids or 350 amino acids or 400 amino acids or 500 or 600 or 700 amino acids.

As used herein, in one embodiment, the terms "peptide" and "fragment" may be used interchangeably having all the same meanings and qualities. As used herein in, in one embodiment the term "peptide" includes native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into bacterial cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided herein under.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylamine (Nol), ring-methylated derivatives of Phe, halogenated derivatives of Phe or o-methyl-Tyr.

In one embodiment, the peptide of this invention further comprises a detectable tag. As used herein, in one embodiment the term "detectable tag" refers to any moiety that can be detected by a skilled practitioner using art known techniques. Detectable tags for use in the screening methods of the present invention may be peptide sequences. Optionally the detectable tag may be removable by chemical agents or by enzymatic means, such as proteolysis. For example the term "detectable tag" includes chitin binding protein (CBP)-tag, maltose binding protein (MBP)-tag, glutathione-S-transferase (GST)-tag, poly(His)-tag, FLAG tag, Epitope tags, such as, V5-tag, c-myc-tag, and HA-tag, and fluorescence tags such as green fluorescent protein (GFP), red fluorescent protein (RFP), yellow fluorescent protein (YFP), blue fluorescent protein (BFP), and cyan fluorescent protein (CFP); as well as derivatives of these tags, or any tag known in the art. The term "detectable tag" also includes the term "detectable marker".

In one embodiment, a peptide of this invention is an isolated peptide. Such an isolated peptide may include a peptide-tag.

The peptides of some embodiments of the invention are preferably utilized in a linear form, although it will be appreciated that in cases where cyclicization does not severely interfere with peptide characteristics, cyclic forms of the peptide can also be utilized.

As used herein, in one embodiment the term "amino acid" refers to naturally occurring and synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl.

Since the present peptides are preferably utilized in therapeutics or diagnostics which require the peptides to be in soluble form, the peptides of some embodiments of the invention preferably include one or more non-natural or natural polar amino acids, including but not limited to serine and threonine which are capable of increasing peptide solubility due to their hydroxyl-containing side chain.

As used herein, in one embodiment the phrase "Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations", which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant", including where the alteration results in the substitution of an amino acid with a chemically similar amino acid. Conservative substitution tables providing functionally similar amino acids are well known in the art. Guidance concerning which amino acid changes are likely to be phenotypically silent can also be found in Bowie et al., 1990, Science 247: 1306 1310. Such conservatively modified variants are in addition to and do not exclude polymorphic variants, interspecies homologs, and alleles. Typical conservative substitutions include but are not limited to: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Amino acids can be substituted based upon properties associated with side chains, for example, amino acids with polar side chains may be substituted, for example, Serine (S) and Threonine (T); amino acids based on the electrical charge of a side chains, for example, Arginine (R) and Histidine (H); and amino acids that have hydrophobic side chains, for example, Valine (V) and Leucine (L). As indicated, changes are typically of a minor nature, such as conservative amino acid substitutions that do not significantly affect the folding or activity of the protein.

Protein Chemical Modifications

In the present invention any part of a protein of the invention may optionally be chemically modified, i.e. changed by addition of functional groups. For example the side amino acid residues appearing in the native sequence may optionally be modified, although as described below alternatively other parts of the protein may optionally be modified, in addition to or in place of the side amino acid residues. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to any one of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

As used herein the term "chemical modification", when referring to a protein or peptide according to the present invention, refers to a protein or peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

Other types of modifications optionally include the addition of a cycloalkane moiety to a biological molecule, such as a protein, as described in PCT Application No. WO 2006/050262, hereby incorporated by reference as if fully set forth herein. These moieties are designed for use with biomolecules and may optionally be used to impart various properties to proteins.

Furthermore, optionally any point on a protein may be modified. For example, pegylation of a glycosylation moiety on a protein may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

By "PEGylated protein" is meant a protein, or a fragment thereof having biological activity, having a polyethylene glycol (PEG) moiety covalently bound to an amino acid residue of the protein.

By "polyethylene glycol" or "PEG" is meant a polyalkylene glycol compound or a derivative thereof, with or without coupling agents or derivatization with coupling or activating moieties (e.g., with thiol, triflate, tresylate, azirdine, oxirane, or preferably with a maleimide moiety). Compounds such as maleimido monomethoxy PEG are exemplary or activated PEG compounds of the invention. Other polyalkylene glycol compounds, such as polypropylene glycol, may be used in the present invention. Other appropriate polyalkylene glycol compounds include, but are not limited to, charged or neutral polymers of the following types: dextran, colominic acids or other carbohydrate based polymers, polymers of amino acids, and biotin derivatives.

Altered Glycosylation Protein Modification

Proteins of the invention may be modified to have an altered glycosylation pattern (i.e., altered from the original or native glycosylation pattern). As used herein, "altered" means having one or more carbohydrate moieties deleted, and/or having at least one glycosylation site added to the original protein.

Glycosylation of proteins is typically either N-linked or O-linked. N-linked refers to the attachment of the carbohydrate moiety to the side chain of an asparagine residue. The tripeptide sequences, asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to proteins of the invention is conveniently accomplished by altering the amino acid sequence of the protein such that it contains one or more of the above-described tripeptide sequences (for N-linked glycosylation sites). The alteration may also be made by the addition of, or substitution by, one or more serine or threonine residues in the sequence of the original protein (for O-linked glycosylation sites). The protein's amino acid sequence may also be altered by introducing changes at the DNA level.

Another means of increasing the number of carbohydrate moieties on proteins is by chemical or enzymatic coupling of glycosides to the amino acid residues of the protein. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, CRC Crit. Rev. Biochem., 22: 259-306 (1981).

Removal of any carbohydrate moieties present on proteins of the invention may be accomplished chemically, enzymatically or by introducing changes at the DNA level. Chemical deglycosylation requires exposure of the protein to trifluoromethanesulfonic acid, or an equivalent compound. This treatment results in the cleavage of most or all sugars except the linking sugar (N-acetylglucosamine or N-acetylgalactosamine), leaving the amino acid sequence intact.

Chemical deglycosylation is described by Hakimuddin et al., Arch. Biochem. Biophys., 259: 52 (1987); and Edge et al., Anal. Biochem., 118: 131 (1981). Enzymatic cleavage of carbohydrate moieties on proteins can be achieved by the use of a variety of endo- and exo-glycosidases as described by Thotakura et al., Meth. Enzymol., 138: 350 (1987).

Pharmaceutical Compositions

The compositions (e.g. SRIPα-41BBL fusion protein, polynucleotide encoding same, nucleic acid construct encoding same and/or cells) of some embodiments of the invention can be administered to an organism per se, or in a pharmaceutical composition where it is mixed with suitable carriers or excipients.

The present invention, in some embodiments, features a pharmaceutical composition comprising a therapeutically effective amount of a therapeutic agent according to the present invention. According to the present invention the therapeutic agent could be a polypeptide as described herein. The pharmaceutical composition according to the present invention is further used for the treatment of cancer or an immune related disorder as described herein. The therapeutic agents of the present invention can be provided to the subject alone, or as part of a pharmaceutical composition where they are mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the composition (e.g. SIRPα-41BBL fusion protein, polynucleotide, nucleic acid construct and/or cells described herein) accountable for the biological effect.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., a polypeptide, a polynucleotide, a nucleic acid construct and/or cell as described herein, may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition according to at least some embodiments of the present invention also may include a pharmaceutically acceptable anti-oxidants. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. A pharmaceutical composition according to at least some embodiments of the present invention also may include additives such as detergents and solubilizing agents (e.g., TWEEN 20 (polysorbate-20), TWEEN 80 (polysorbate-80)) and preservatives (e.g., Thimersol, benzyl alcohol) and bulking substances (e.g., lactose, mannitol).

Examples of suitable aqueous and nonaqueous carriers that may be employed in the pharmaceutical compositions according to at least some embodiments of the present invention include water, buffered saline of various buffer content (e.g., Tris-HCl, acetate, phosphate), pH and ionic strength, ethanol, polyols (such as glycerol, propylene glycol, polyethylene glycol, and the like), and suitable mixtures thereof, vegetable oils, such as olive oil, and injectable organic esters, such as ethyl oleate.

Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions according to at least some embodiments of the present invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the present invention are dictated by and directly dependent on (a) the unique characteristics of the active compound and the particular therapeutic effect to be achieved, and (b) the limitations inherent in the art of compounding such an active compound for the treatment of sensitivity in individuals.

Techniques for formulation and administration of drugs may be found in "Remington's Pharmaceutical Sciences," Mack Publishing Co., Easton, Pa., latest edition, which is incorporated herein by reference.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

A composition of the present invention can be administered via one or more routes of administration using one or more of a variety of methods known in the art. As will be appreciated by the skilled artisan, the route and/or mode of administration will vary depending upon the desired results. Preferred routes of administration for therapeutic agents according to at least some embodiments of the present invention include intravascular delivery (e.g. injection or infusion), intravenous, intramuscular, intradermal, intraperitoneal, subcutaneous, spinal, oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intracerebral, and convection enhanced diffusion), CNS delivery (e.g. intrathecal, perispinal, and intra-spinal) or parenteral (including subcutaneous, intramuscular, intraperitoneal, intravenous (IV) and intradermal), transdermal (either passively or using iontophoresis or electroporation), transmucosal (e.g., sublingual administration, nasal, vaginal, rectal, or sublingual), administration or administration via an implant, or other parenteral routes of administration, for example by injection or infusion, or other delivery routes and/or forms of administration known in the art. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion or using bioerodible inserts, and can be formulated in dosage forms appropriate for each route of administration. In a specific embodiment, a protein, a therapeutic agent or a pharmaceutical composition according to at least some embodiments of the present invention can be administered intraperitoneally or intravenously.

Compositions of the present invention can be delivered to the lungs while inhaling and traverse across the lung epithelial lining to the blood stream when delivered either as an aerosol or spray dried particles having an aerodynamic diameter of less than about 5 microns. A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected. For the polypeptide compositions disclosed herein, the polynucleotides and nucleic acids constructs encoding the same and the cells described herein, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For polypeptide compositions, generally dosage levels of 0.0001 to 100 mg/kg of body weight daily are administered to mammals and more usually 0.001 to 20 mg/kg. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration 5 times per week, 4 times per week, 3 times per week, 2 times per week, once per week, once every two weeks, once every three weeks, once every four weeks, once a month, once every 3 months or once every three to 6 months.

Generally, for intravenous injection or infusion, dosage may be lower. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the present invention are dictated by and directly dependent on (a) the unique characteristics of the active compound and the particular therapeutic effect to be achieved, and (b) the limitations inherent in the art of compounding such an active compound for the treatment of sensitivity in individuals.

Optionally the polypeptide formulation may be administered in an amount between 0.0001 to 100 mg/kg weight of the patient/day, preferably between 0.001 to 20.0 mg/kg/day, according to any suitable timing regimen. A therapeutic composition according to at least some embodiments according to at least some embodiments of the present invention can be administered, for example, three times a day, twice a day, once a day, three times weekly, twice weekly or once weekly, once every two weeks or 3, 4, 5, 6, 7 or 8 weeks. Moreover, the composition can be administered over a short or long period of time (e.g., 1 week, 1 month, 1 year, 5 years).

Alternatively, therapeutic agent such as the compositions disclosed herein can be administered as a sustained release formulation, in which case less frequent administration is required. Dosage and frequency vary depending on the half-life of the therapeutic agent in the patient. In general, human antibodies show the longest half-life, followed by humanized antibodies, chimeric antibodies, and nonhuman antibodies. The half-life for fusion proteins may vary widely. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of a polypeptide as disclosed herein preferably results in a decrease in severity of disease symptoms, an increase in frequency and duration of disease symptom-free periods, an increase in lifespan, disease remission, or a prevention or reduction of impairment or disability due to the disease affliction.

One of ordinary skill in the art would be able to determine a therapeutically effective amount, especially in light of the detailed disclosure provided herein, based on such factors as the subject's size, the severity of the subject's symptoms, and the particular composition or route of administration selected.

In certain embodiments, the polypeptide, polynucleotide, nucleic acid construct or cells compositions are administered locally, for example by injection directly into a site to be treated.

Typically, the injection causes an increased localized concentration of the polypeptide, polynucleotide, nucleic acid construct or cells compositions which is greater than that which can be achieved by systemic administration. The polypeptide compositions can be combined with a matrix as described above to assist in creating an increased localized concentration of the polypeptide compositions by reducing the passive diffusion of the polypeptides out of the site to be treated.

Pharmaceutical compositions of the present invention may be administered with medical devices known in the art. For example, in an optional embodiment, a pharmaceutical composition according to at least some embodiments of the present invention can be administered with a needles hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in an optional embodiment, a therapeutic composition according to at least some embodiments of the present invention can be administered with a needles hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art. In certain embodiments, to ensure that the therapeutic compounds according to at least some embodiments of the present invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J Physiol. 1233:134); p120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

Formulations for Parenteral Administration

In a further embodiment, compositions disclosed herein, including those containing peptides and polypeptides, are administered in an aqueous solution, by parenteral injection. The formulation may also be in the form of a suspension or emulsion. In general, pharmaceutical compositions are provided including effective amounts of a peptide or polypeptide, polynucleotide, nucleic acid construct or cells described herein, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., water soluble antioxidants such as ascorbic acid, sodium metabisulfite, cysteine hydrochloride, sodium bisulfate, sodium metabisulfite, sodium sulfite; oil-soluble antioxidants, such as ascorbyl palmitate, butylated hydroxyanisole (BHA), butylated hydroxytoluene (BHT), lecithin, propyl gallate, alpha-tocopherol; and metal chelating agents, such as citric acid, ethylenediamine tetraacetic acid (EDTA), sorbitol, tartaric acid, phosphoric acid), and preservatives (e.g., Thimersol, benzyl alcohol) and bulking substances (e.g., lactose, mannitol). Examples of non-aqueous solvents or vehicles are ethanol, propylene glycol, polyethylene glycol, vegetable oils, such as olive oil and corn oil, gelatin, and injectable organic esters such as ethyl oleate. The formulations may be freeze dried (lyophilized) or vacuum dried and redissolved/resuspended immediately before use. The formulation may be sterilized by, for example, filtration through a bacteria retaining filter, by incorporating sterilizing agents into the compositions, by irradiating the compositions, or by heating the compositions.

Formulations for Topical Administration

Various compositions (e.g., polypeptides) disclosed herein can be applied topically. Topical administration does not work well for most peptide formulations, although it can be effective especially if applied to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets or lozenges.

Transdermal formulations may also be prepared. These will typically be ointments, lotions, sprays, or patches, all of which can be prepared using standard technology. Transdermal formulations will require the inclusion of penetration enhancers.

Controlled Delivery Polymeric Matrices

Various compositions (e.g., polypeptides) disclosed herein may also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of polypeptides or nucleic acids encoding the polypeptides, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release, 5:13-22 (1987); Mathiowitz, et al., Reactive Polymers, 6:275-283 (1987); and Mathiowitz, et al., J. Appl Polymer ScL, 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

EXAMPLES

Proof of Concept (POC) Experiments
Manufacturing of a His-Tagged SIRPα-41BBL

For initial POC analysis, a histidine-tagged protein is produced. A cDNA sequence, coding for a 6-His-tagged SIRPα-41BBL, is sub-cloned into a mammalian expression vector. Transfection-grade plasmid preparation is used for plasmid transfection into Expi293 cells or other cell-lines. The supernatant of the Expi293 expressing cells (100 ml scale) is assessed for SIRPα-41BBL production by reduced and non-reduced SDS-PAGE and Western blot (WB) with an anti-His antibody. His-tagged SIRPα-41BBL is then purified from a positive supernatant by one-step affinity based purification (Nickel beads). The production of the tagged chimera protein is verified by SDS-PAGE and Western blot analysis using specific antibodies against each domain of the molecule (i.e. the extracellular domain each of SIRPα and 41BBL).

Experiment 1A—Production of a His-Tagged SIRPα-41BBL Fusion Protein

Production of His-tag SIRPα-41BBL fusion protein (SEQ ID NO: 5) was effected in Expi293F cells transfected by a pcDNA3.4 expression vector cloned with coding sequence for the full fusion protein. The sequence was cloned into the vector using EcoRI and HindIII restriction enzymes, with addition of Kozak sequence, artificial signal peptide and 6 His-tag in the N terminus and a stop codon in the C terminus (SEQ ID NO: 15).

The protein was collected from the supernatant of cell culture, and purified by one-step purification by HisTrap™ FF Crude column.

Experiment 1B—the Produced SIRPα-41BBL Fusion Protein Contains Both Domains

Materials—

His-tagged SIRPα-41BBL protein (SEQ ID NO: 5) produced as described in Experiment 1A hereinabove, Protein marker: Spectra BR (Thermo Fisher Scientific, cat #26634), anti-SIRPα (SHPS1) (Cell Signaling, cat #13379), anti-41BB-L (BioVision, 5369-100), mouse-anti-His mAb (GenScript, Cat.No. A00186), secondary Goat Anti-Rabbit IgG (H+L)-HRP Conjugate (1:3333) (R&D, cat #170-6515), Recombinant hSIRPα 0.1 mg/ml (4546-SA-050) R&D, Recombinant h41BB-L (TNFSF9) 0.1 mg/ml (8460 LF) Cell Signaling Stripping buffer (Thermoscientific, cat #21059), Protein De-glycosylation Mix: (NEB p6044).

Methods—

Proteins (250 ng per lane) were treated at denaturing or non denaturing conditions (in sample buffer containing P3-mercaptoethanol and boiled for 5 minutes at 95° C., or, in sample buffer without P3-mercaptoethanol without heating, respectively) and separated on 12% SDS-PAGE gel, followed by Western blotting. De-glycosylation treatment was effected by PNGase F enzyme according to the Protein De-glycosylation Mix manufacturer instructions.

Results—

Western blot analysis of His-tagged SIRPα-41BBL (SEQ ID NO: 5) separated on a SDS-PAGE under denaturing conditions followed by immunoblotting with an anti His-tag antibody (FIG. 1) or an anti-41BBL antibody (FIG. 2A) demonstrated that both the N-terminal side of the molecule and the C-terminal side of the molecule are present. Although the predicted molecular weight of the protein according to its amino acid sequence is approximately 60 kDa, the protein migrated in denaturing conditions as approximately the size of 85 kDa. This shift was found to be related to the glycosylation of the protein, as determined by treating the protein with PNGase F enzyme that removes almost all N-linked oligosaccharides from glycoproteins. Following the treatment, a major band of around 60 kDa was observed (FIG. 2C).

When separated on a SDS-PAGE under non-denaturing conditions (FIGS. 1 and 2B) the His-tagged SIRPα-41BBL (SEQ ID NO: 5) was detected at the same molecular weight, as in the denaturing conditions (FIGS. 1, 2A and 2B). Additional bands of higher molecular weight were also detected, which were stronger under the non denaturing conditions compared to the denaturing conditions. This might suggest a formation of a multimer, probably a trimer according to the size of the multimer and the fact that 41BBL protein naturally tends to form trimers (Eun-Young et al, 2010, THE JOURNAL OF BIOLOGICAL CHEMISTRY VOL. 285, NO. 12, pp. 9202-9210).

Experiment 1C—Binding Analysis of the SIRPα and 4-1BBL Moieties of the Chimera to CD47 and 41BB The binding of the SIRPα domain of the molecule to CD47 and the binding of the 41BBL domain of the molecule to 41BB was determined by the bio-layer interferometry Blitz® assay.

Materials—

CD47:FC (Sino Biological, cat #12283-HO2H), 41BB:FC (Sino Biological, cat #10041-HO3H), His-tagged SIRPα-41BBL protein (SEQ ID NO: 5) produced as described in Experiment 1A hereinabove; PD1-CD70 protein (SEQ ID NO: 6, as a negative control).

Methods and Results—

The biosensor was pre-loaded with CD47:Fc, which led to a stable association plateau (FIG. 3A). Upon subsequent incubation with his-tagged SIRPα-41BBL (SEQ ID NO: 5)

a rapid association of the his-tagged SIRPα-41BBL to CD47:Fc was detected (FIG. 3A). Similar incubation with control protein PD1-CD70 (composed of a PD-1 domain fused to CD70, SEQ ID NO: 6), did not lead to any binding to CD47:Fc (FIG. 3A). Furthermore, when the biosensor was not pre-loaded with CD47:Fc, the his-tagged SIRPα-41BBL did not associate (FIG. 3A, bottom line). Upon reaching a stable association plateau, the biosensor was washed with medium to determine the off-rate of the his-tagged SIRPα-41BBL from CD47:Fc. The dissociation of the his-tagged SIRPα-41BBL from the CD47:Fc-loaded biosensor was very slow, suggesting stable interaction of SIRPα with CD47.

Upon similar loading of the biosensor with 41BB:Fc, binding of the 41BBL unit of his-tagged SIRPα-41BBL (SEQ ID NO: 5) was evaluated (FIG. 3B). As with the SIRPα domain, the 41BBL domain of the his-tagged SIRPα-41BBL rapidly bound to its target receptor (FIG. 3B), with the off-rate for the 41BBL/41BB interaction being also very slow, as evident from the limited dissociation occurring during the last dissociation phase. Control treatment with a PD1-CD70 (SEQ ID NO: 6), lacking the 41BBL domain, did not result in any detectable binding to 41BBL:Fc (FIG. 3B). Further, in the absence of pre-loading with 41BB:Fc, His-tagged SIRPα-41BBL did not detectably bind to the biosensor (FIG. 3B, bottom line).

Taken together, both domains of His-tagged SIRPα-41BBL (SEQ ID NO: 5) retain functional binding activity for their cognate receptors.

Experiment 1D—Binding Analysis of the SIRPα and 41BBL Moieties of the Chimera to CD47

The binding of the SIRPα domain of the molecule to human CD47 is evaluated by using HT1080 cells or CHO-K1 cell or another cell line overexpressing CD47 or with a cancer cell line that is known to express CD47 at high levels. CD47 knock-out cells are serving as negative control. Cells are stained with different concentrations of His-tagged SIRPα-41BBL, and then by a secondary anti 41BBL antibody. Binding is analyzed by flow cytometry using fluorescence-activated cell sorting (FACS). The use of different concentrations of the chimera allows to determine the affinity of the molecule to the CD47. In this binding test, a recombinant SIRPα is also used as competitor to the SIRPα-41BBL in order to verify the specificity of the binding. Antibodies that block the interaction between SIRPα and CD47 can be used as well for the same purpose.

The binding of the 41BBL moiety of the chimera to human 41BB is tested by using HT1080 cells or another cell line that are overexpressing 41BB. Cells are stained with different concentrations of SIRPα-41BBL and then by a secondary anti SIRPα antibody, and binding affinity is analyzed by FACS. In this binding test, a recombinant 41BBL is used as a competitor to the SIRPα-41BBL in order to verify the specificity of the binding. Antibodies that block the interaction between 41BB and 41BBL can be used for the same purpose as well.

Materials—

His-tagged SIRPα-41BBL protein (SEQ ID NO: 5) produced as described in Experiment 1A hereinabove; CHO-WT and CHO-CD47 cell lines (Bommel et al, 2017), Fixable Viability Dye (BD Biosciences, cat #562247), Human Fc blocker, True stain FCX (Biolegend, cat #422302), and the following antibodies:

|  | Target | Fluor | Cat# | Manufacturer |
| --- | --- | --- | --- | --- |
| Antibodies used for receptor staining | anti 41BB (CD137) IgG1 | APC | 309810 400122 |  |
|  | anti CD47 IgG2b | Alexa 647 | MCA2514A647 MCA691A647 | BioRad |
| Antibodies used for Binding assay | anti 41BBL IgG1, K | PE | 311504 400112 | Biolegend |

Methods—

For expression assays, cells (0.5 M cells/sample) were immuno-stained with the indicated antibodies, followed by Flow cytometry analysis. For binding assays, cells were pre-incubated with human Fc blocker prior to incubation with different concentrations (0.01-50 g/ml) of the His-tagged SIRPα-41BBL protein (SEQ ID NO: 5) for 30 minutes on ice, followed by immuno-staining with antibodies against the "free" arm of the molecule (41BBL), fixation and analysis by flow cytometry.

Results—

As shown in FIGS. 4A-B, CHO-K1-WT cells do not express CD47 nor 41BB; while CHO-K1-CD47 cells express CD47 but do not express 41BB.

Binding assays showed that His-tagged SIRPα-41BBL (SEQ ID NO: 5) binds to CHO-CD47 cells in as dose dependent manner, while it doesn't bind to CHO-WT cells (FIGS. 5A-B).

Taken together, the N terminal of His-tagged SIRPα-41BBL protein (SEQ ID NO: 5) can bind CD47 overexpressed on the surface of cells.

Experiment 2—Activation of the 41BB Receptor by the Chimera

The activation effect of the 41BB receptor by the His-tagged SIRPα-41BBL is tested by using HT1080 cells or another cell line that are overexpressing the 41BB receptor. Specifically, the HT1080-41BB cell line is overexpressing 41BB and is known to secrete IL-8 upon binding of 41BBL (Wyzgol, et al, 2009, The Journal of Immunology). Upon binding of 41BBL to the 41BB receptor on the surface of these cells, a signaling pathway is activated resulting in secretion of IL8. The cells are incubated in the presence of the His-tagged SIRPα-41BBL in different concentrations and IL8 secretion to the culture media is determined by ELISA. The oligomerization is tested by addition of anti-His-tag cross linking antibody in different concentrations. With the addition of the anti-His-tag Ab, the chimera molecules will be cross linked and form oligomers, resulting in an increased IL8 secretion. Anti SIRPα antibody can be used for the same purpose as well (cross linking the SIRPα moiety of the molecule).

The oligomerization is also tested by co-culturing the cells overexpressing the 41BB receptor with HT1080 cells that are overexpressing human CD47 or with cancer cell line that are highly expressing CD47. The SIRPα-41BBL binds to the CD47 that is expressed on the HT1080 or cancer cells and the 41BBL moiety is presented to the HT1080 that are overexpressing the 41BB receptor. Due to this presentation of several molecules in close vicinity, the requirement for oligomerization is fulfilled.

The activation of the 41BBL receptor by His-tagged SIRPα-41BBL can be compared to that of its parts, namely, recombinant SIRPα or 41BBL alone or in combination.

Materials—

His-tagged SIRPα-41BBL protein (SEQ ID NO: 5) produced as described in Experiment 1A hereinabove, HT1080-41BB cells (Lang et al 2015), IL-8 ELISA kit (cat #D8000C, R&D), DMEM (cat #01-055-1A, Biological industries), FBS (cat #10270106, Rhenium), AIM V (serum free medium) (ThermoScientific).

Methods—

HT1080-41BB cells (5000 per well) were incubated for 24 hours with different concentrations of His-tagged SIRPα-41BBL protein (SEQ ID NO: 5). IL-8 concentration in the supernatant was determined by IL-8 ELISA kit according to the manufacturer's protocol. Serum free medium was used for some of the experiments to eliminate relatively high background that was detected using medium with FBS.

Results—

Figure 7:
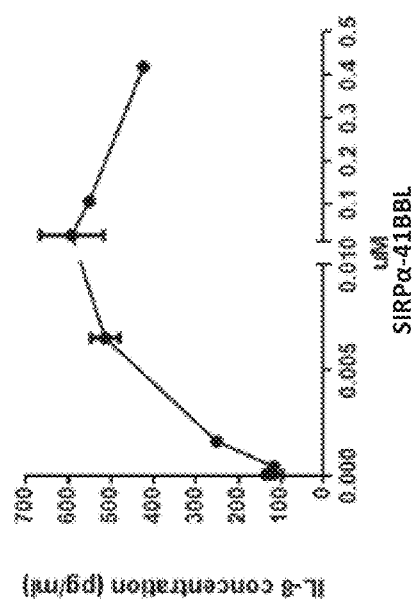
FIG. 7 is a graph demonstrating that His-tagged SIRPα-41BBL protein (SEQ ID NO: 5) promotes TNFR signaling as demonstrated by IL-8 secretion from HT1080-41BB cells in serum free media.

Several independent experiments showed the functionality of SIRPα-41BBL: His-tagged SIRPα-41BBL protein (SEQ ID NO: 5) was able to trigger TNFR signaling as determined by IL8 secretion by HT1080-41BBL cells, in a dose dependent manner both in medium containing FBS (FIG. 6) and in Serum free medium (FIG. 7).

Experiment 3—Activation of T-Cells by SIRPα-41BBL

The effect of SIRPα-41BBL on the activation of T-cells is tested using either T-cells in human healthy donor PBMCs or by using human TILs. The T-cells are first co-cultured with human carcinoma cancer cells and treated with anti CD3 and anti Epcam1 bispecific antibodies to induce T-cell activation and then with the SIRPα-41BBL. The anti CD3/Epcam1 antibody is delivering the first signal for activation of T cells against the Epcam1 expressing cancer cells. The SIRPα-41BBL molecule is interacting with CD47 expressed on the surface of cancer cells, this interaction facilitates the presentation and oligomerization of the molecule and by that, enables the interaction of the 41BBL moiety with 41BB receptor on The T cell and delivery of a second co-stimulatory signal to the T cell. The activation level of the T cells is determined by measuring several parameters; Firstly, by testing the expression of activation markers on the surface of the T cells, (for example: CD25, CD69, CD62L, CD137, CD107a, PD1 etc.). Expression of activation markers is tested by staining the cells with specific antibodies and flow cytometry analysis (FACS). A second way to determine T cell activation is by measuring inflammatory cytokine secretion (for example: IL2, IL6, IL8, INF gamma etc.). Secretion of inflammatory cytokine is tested by ELISA. Proliferation of T cells is measured by pre-staining of T cells with CFSE (carboxyfluorescein succinimidyl ester) and determining deviation of cells by CFSE dilution that is determined by FACS. An additional parameter that is tested is the killing of the cancer cells that is measured by pre-labeling the cancer cells using Calcine-AM reagent and measuring Calcine release into the culture medium using luminescence plate reader.

The effect of SIRPα-41BBL on the activation of TILs is tested on TILs that are extracted from tumors and then co-cultured with the tumor cancer cells and treated with SIRPα-41BBL. The first signal for activation of T cells is delivered by the cancer cells via MHC class I: peptide—TCR (T cell receptor) pathway. The SIRPα-41BBL fusion protein is interacting with CD47 expressed on the surface of the tumor cells, this interaction facilitates the presentation and oligomerization of the molecule and accordingly enables the interaction of the 41BBL moiety with 41BB receptor on the T cell and delivery of a second co-stimulatory signal to the T cell. Activation level of the TILs and killing of tumor cells is determined in the same way as described (activation markers, cytokine secretion, proliferation and killing of tumor cells).

The activation of T-cells by His-SIRPα-41BBL can be compared to that of its parts, namely, recombinant SIRPα or 41BBL alone or in combination.

Experiment 3A—SIRPα-41BBL Protein Demonstrates T Cell Co-Stimulatory Activity

Materials—

His-tagged SIRPα-41BBL protein (SEQ ID NO: 5) produced as described in Experiment 1A hereinabove; HT1080-41BB, CHO-WT, CHO-K1-CD47 and DLD1 cell lines (Bommel et al 2017, Lang et al 2015, ATCC-CCL-221), freshly isolated human T cells, IL8 Elisa kit (R&D systems, cat #DY208), CD47:FC (Sino Biological, cat #12283-HO2H), Anti-CD3/anti-CD28 activation beads (Life Technologies, cat #11131D), Anti CD25 antibody (Immuno Tools, cat #21270256), Lymphoprep (Stemcell, 07851) Name: CD14 MicroBeads, human (miltenyi Biotec, 130-050-201).

Methods and Results—

Upon treatment of single cultures of HT1080 cells transduced with 41BB (HT1080-41BB) with His-tagged SIRPα-41BBL (SEQ ID NO: 5), minimal production of IL-8 was detected following 24 hours of incubation (FIG. 8A). Similarly, treatment with His-tagged SIRPα-41BBL (SEQ ID NO: 5) minimally induced IL-8 secretion when HT1080-41BB cells were mixed with wild-type CHO cells (FIG. 8A). However, treatment with His-tagged SIRPα-41BBL (SEQ ID NO: 5) of mixed cultures of HT1080-41BB with CHO-CD47 (enabling the SIRPα domain to bind to CHO-CD47 and present cross-linked 41BBL to HT1080-41BB), triggered a strong increase in IL-8 secretion that peaked at 2000 pg/mL (FIG. 8B). Thus, binding of the His-tagged SIRPα-41BBL protein (SEQ ID NO: 5) to CD47 is beneficial in order to stimulate IL-8 secretion upon 41BBL/41BB interaction.

Next, the potential induction of T cell activation by the 41BBL domain of His-tagged SIRPα-41BBL (SEQ ID NO: 5) was evaluated. PBMCs were isolated from blood of healthy donors with Lymphoprep according to manufacturer's instructions. Cells were then stained with CD14 MicroBeads and T cells were isolated according to manufacturer's instructions with the MACS sorting system. To this end, freshly isolated T cells were added to CD47-Fc coated plates and activated with sub-optimal concentrations of anti-CD3/anti-CD28 activation beads for 3 days. Following treatment, a clear increase in the percentage of activated CD25+ T cells was detected in the His-tagged SIRPα-41BBL treated cells (FIG. 8C), with an optimum induction at ~2.5 µg/ml. In subsequent mixed cultures of DLD-1 cells and T cells, the treatment with His-tagged SIRPα-41BBL protein (SEQ ID NO: 5) increased the percentage of CD25+ T cells (FIGS. 8C-E), indicating that SIRPα-41BBL protein can activate T cells. Thus, binding of His-tagged SIRPα-41BBL protein (SEQ ID NO: 5) to CD47 enables 41BBL/41BB-mediated co-stimulation and activation of T cells.

Taken together, these data provide clear evidence that upon CD47-mediated binding, His-tagged SIRPα-41BBL protein (SEQ ID NO: 5) gains 41BBL-mediated co-stimulatory activity that can augment T cell activation.

Experiment 3B—SIRPα-41BBL Protein Augments Human PBMCs Activation

Materials—

His-tagged SIRPα-41BBL protein (SEQ ID NO: 5) produced as described in Experiment 1A hereinabove; INF-γ ELISA Kit [cat #900-TM27, cat #900-T00—Elisa Buffer Kit (TMB)], RPMI (cat #01-100-1A, Biological industries), FBS (cat #12657-029, Gibco), L-Glutamine (cat #25030-24, Gibco), Pen/Strep (cat #15140-122, Gibco), Leaf purified Anti-human CD3 (cat #BLG-317315, BioLegend), Recombinant human IL2 (cat #202-IL-500, R&D Systems), Human Peripheral Blood Mononuclear Cells (PBMCs) isolated from healthy donor peripheral blood by Ficoll-Paque (cat #17-1440-03, GE Healthcare), anti-CD47 antibody (cat #MCA2514A647, Biorad), anti-41BBL antibody (cat #311504, Biolegend), MV4-11 human leukemia cells (ATCC, Abraham et al 2017).

Methods—

MV4-11 cells were tested for CD47 expression and binding of His-tagged SIRPα-41BBL by flow cytometry. Human PBMCs were isolated from healthy donor peripheral blood using Ficoll-Paque method (Grienvic et al. 2016). Following, PBMCs were cultured for 40 hours with addition of different concentrations of His-tagged SIRPα-41BBL protein (SEQ ID NO: 5), in the presence of anti-CD3 (30 ng/ml) or anti-CD3 plus IL2 (1000 U/ml). The experiment was effected with or without co-culture with CD47 expressing human cancer cell line MV4-11 (ratio 1:1). INF-γ concentration in the cells supernatant was determined by INF-γ ELISA kit according to the manufacturer's protocol.

Results—

Human PBMCs, including NK cells, NKT cells, CD4+ and CD8+ effector cells, are known to secrete pro-inflammatory Interferon-γ (INF-γ) in response to activation. The activation of a T cell requires two signals: ligation of the T-Cell Receptor (TCR) with the Major Histocompatibility Complex (MHC)/peptide complex on the Antigen Presenting Cell (APC) and cross-linking of co-stimulatory receptors on the T cell with the corresponding ligands on the APC. 41BB, is a T cell co-stimulatory receptor induced by ligation of 41BBL. 41BB transmits a potent costimulatory signal to both CD8+ and CD4+ T cells, promoting their expansion, survival, differentiation, and cytokine expression. Its ligand, 41BBL, is a membrane protein, which provides a co-stimulatory signal to T cells.

In this experiment the functionality of SIRPα-41BBL molecule in enhancing human PBMCs activation was evaluated.

Figure 9A:
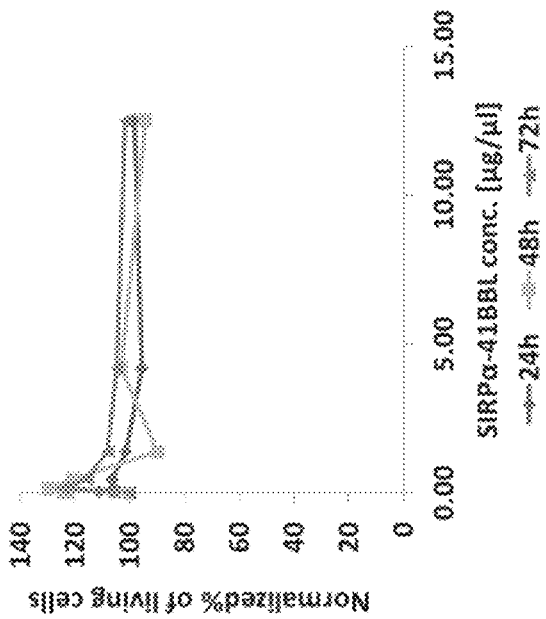
FIGS. 9A-C demonstrate that SIRPα-41BBL does not have a direct killing effect on MV4-11 cancer cells.
Figure 9B:
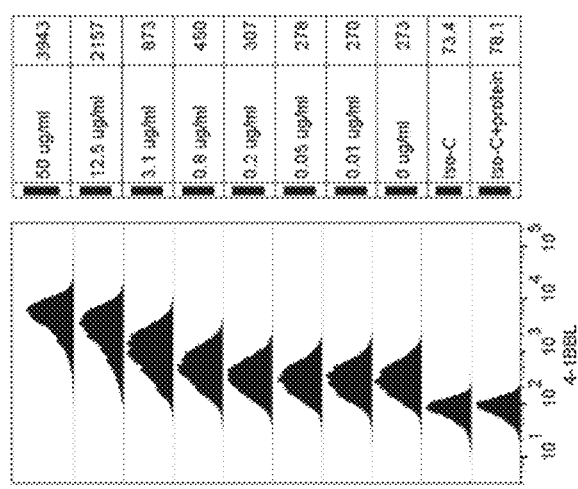
Figure 9C:
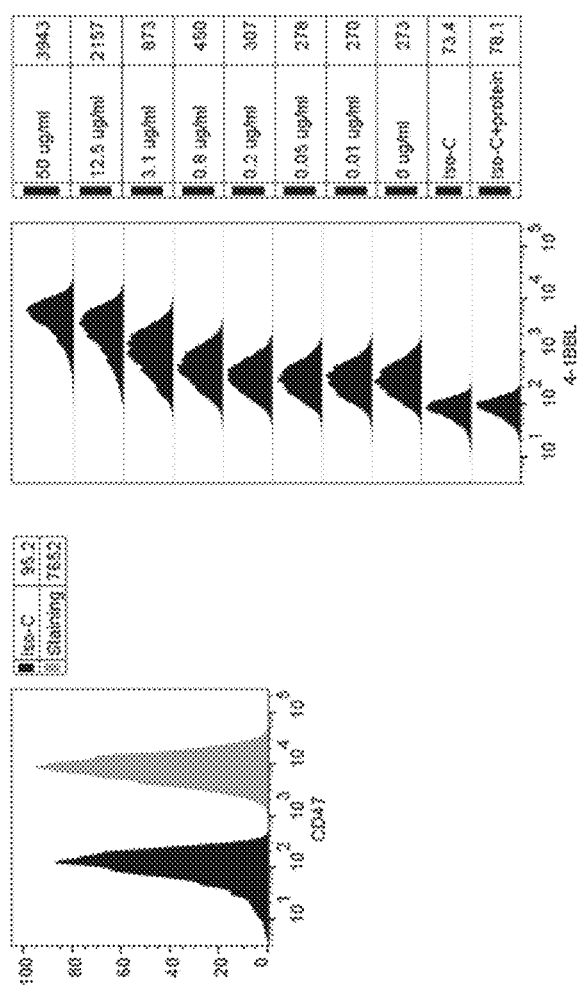

CD47 is present on the surface of MV4-11 cells and His-tagged SIRPα-41BBL protein (SEQ ID NO: 5) bound these cells in a dose dependent manner (FIGS. 9A-B). Incubation of MV4-11 cells with different concentrations of His-tagged SIRPα-41BBL protein (SEQ ID NO: 5) up to 72 hours did not show any direct killing effect (FIG. 9C).

Figure 10A:
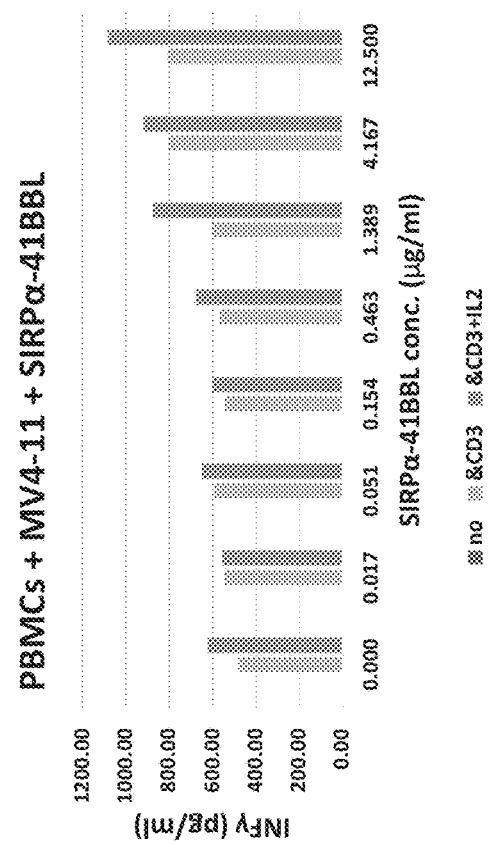
FIGS. 10A-B demonstrate that SIRPα-41BBL promotes INF-γ secretion from anti-CD3 primed human PBMCs.

Addition of His-tagged SIRPα-41BBL protein (SEQ ID NO: 5) enhanced the activation of PBMCs in a dose depended manner, as can be seen by an increase in INF-γ secretion by PBMCs that were stimulated with anti-CD3 antibody, with or without the addition of IL2 (FIG. 10A).

Figure 10B:
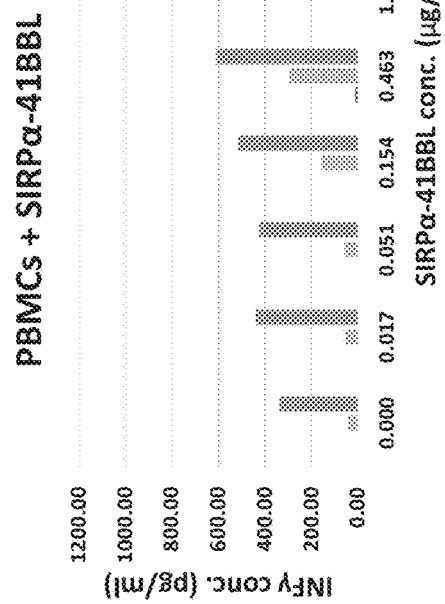

Co-culturing PBMCs with human cell line MV4-11 and stimulating the cells with anti CD3 antibody resulted in INF-γ secretion, probably due to direct stimulation of the PBMCs cells by the MV4-11 cells. Treatment with His-tagged SIRPα-41BBL protein (SEQ ID NO: 5) had a moderate effect that was more pronounced when added together with IL2 (FIG. 10B).

Taken together, His-tagged SIRPα-41BBL protein (SEQ ID NO: 5) augments activation of human PBMCs, as can be seen by increase in IFN-γ secretion Experiment 4—Effect of SIRPα-41BBL on Granulocytes and Macrophages SIRPα is an inhibitory receptor expressed on the cell surface of e.g. phagocytic cells. CD47, the ligand for SIRPα, is extensively expressed on tumor cells. Upon engaging of SIRPα by CD47, SIRPα delivers a "don't eat me" signal to phagocytic cells. By interaction of SIRPα-41BBL with CD47, it should block the endogenous interaction of CD47 with SIRPα and by that block the "don't eat me" signal, allowing the engulfment of the tumor cells by phagocytic cells.

The effect of SIRPα-41BBL on granulocytes, macrophages and other phagocytic cells, is tested in-vitro in a co-culture assay using granulocytes or M1 macrophages from healthy donors co-cultured with fluorescently labeled CD47 expressing cancer cells. SIRPα-41BBL is added to the co-culture in different concentrations and phagocytosis is determined by measuring the fluorescent uptake by the granulocytes or M1 macrophages, using flow cytometry. The phagocytic cells are identified and distinguished from the cancer cells by staining for specific surface markers (like CD11b).

The phagocytic effect in this experiment can be enhanced using Therapeutic Anti-Tumor antibodies (such as Rituximab, Cetuximab, Trastuzumab, Alemtuzumab, etc.) Similar experiment is done using autologous granulocytes from cancer patient co-cultured with primary autologous malignant cells as well.

Materials—

His-tagged SIRPα-41BBL protein (SEQ ID NO: 5) produced as described in Experiment 1A hereinabove, Human leukocytes isolated from peripheral blood, tumor cell lines: BJAB, U2932, Raji, Sudhl6, DLD1, H292, FADU, OVCR, MOLM13, K562, OCIAML3, HL60 (ATCC), vybrant DiD (Invitrogen, cat #V22887), cell proliferation dye V450 (Thermofishr, 65-0842-85), Lymphoprep (Stemcell technology, 07851) Recombinant human SIRPα (sino biological, 11612-H08H) Recombinant human 41BBL (R&D systems, 2295-4L/CF).

Methods and Results—

Leukocytes were isolated from peripheral blood of healthy donors. In short, whole blood was mixed with PBS containing EDTA at ratio of 1:1 and mixed with lymphoprep. To obtain neutrophils, PBMCs were removed following lymphoprep and cell pellet was harvested. Cell pellet was mixed with erythrocytes lysis buffer at a ratio of 1:10 and incubated at 4° C. for 30-45 minutes. Following, neutrophils were harvested by centrifugation at 450 g/5 minutes and washed twice with PBS containing EDTA Isolated leukocytes were mixed with tumor cells, that had been pre-stained with vybrant DiD, at a 1:1 ratio. The uptake of tumor cells by granulocytes was subsequently evaluated using flow cytometry (for gating strategy see FIG. 11A). In such mixed cultures, granulocytes minimally phagocytose tumor cells in the absence of any stimulus (FIG. 11A). However, when mixed cultures of leukocytes and Ramos B-NHL cells were treated with increasing concentration of His-tagged SIRPα-41BBL (SEQ ID NO: 5), a clear dose-dependent induction of phagocytosis by granulocytes was detected, with an optimum effect achieved at 2.5 μg/ml (FIGS. 11A-B). Similar pro-phagocytic activity of single agent treatment with His-tagged SIRPα-41BBL protein (SEQ ID NO: 5) was detected toward a panel of B-cell lymphoma cell lines, yielding an increase in phagocytosis of 15% to 20% compared to untreated cultures (FIG. 11C).

Following, the mixed cultures were treated with a combination of His-tagged SIRPα-41BBL protein (SEQ ID NO: 5) and the anti-CD20 antibody rituximab. As shown in FIG. 11D, treatment with low sub-optimal concentration of rituximab already triggered phagocytosis by granulocytes, the extent of which depended on the leukocytes donor and cell line (FIG. 11D, white diamond squares). However, combination treatment with rituximab and His-tagged SIRPα-41BBL protein (SEQ ID NO: 5) further increased phagocytic uptake of all B-NHL cell lines tested (FIG. 11D, black diamond squares).

To determine whether combination of SIRPα-41BBL with other therapeutic antibodies would similarly augment phagocytosis, a panel of carcinoma cell lines was mixed with leukocytes. Phagocytosis by granulocytes was evaluated upon treatment with His-tagged SIRPα-41BBL protein (SEQ ID NO: 5) with or without the anti-EGFR antibody cetuximab. In all carcinoma cell lines tested, single agent treatment with the His-tagged SIRPα-41BBL already strongly triggered phagocytic uptake of cancer cells (FIG. 11E), with up to 80% of granulocytes phagocytosing DLD-1 cells. Upon combination treatment with His-tagged SIRPα-41BBL and cetuximab, the phagocytic uptake of cancer cells was increased even further (FIG. 11F): for example, in the squamous cell carcinoma line FaDu, over 90% were phagocytosed, suggesting an additive or even synergistic effect of cetuximab with SIRPα-41BBL for this but also other cell lines.

Subsequent analysis of phagocytosis of several acute myeloid leukemia cell lines revealed that most of these cell lines did not respond to treatment with His-tagged SIRPα-41BBL protein (SEQ ID NO: 5) alone (FIG. 11G). A notable exception here was HL60, an acute promyelocytic leukemia cell line, with an increase in HL60 phagocytosis of ~10-20% (depending on the donor) compared to untreated cultures, following 2 hours of incubation. Upon prolonged treatment of up to 24 hours, granulocyte-mediated phagocytosis of K562 (chronic myelogenous leukemia) and Oci-AML3 (acute myeloid leukemia) was also strongly increased compared to untreated cultures, whereas HL60 uptake at this extended time-point was already very high in the untreated control cultures (FIG. 11H). Increasing the His-tagged SIRPα-41BBL (SEQ ID NO: 5) dose at the 2 hours' time-point further increased phagocytosis of HL60, but not of MOLM13 (FIG. 11I).

Importantly, also primary AML blasts, obtained from an AML patient with complex karyotype, were phagocytosed upon treatment with His-tagged SIRPα-41BBL (SEQ ID NO: 5) in a dose-dependent manner (FIG. 11J). In an extended panel of allogeneic granulocytes from five healthy donors, these primary AML blasts were strongly phagocytosed within 2 hours with a median increase in phagocytosis of ~35% compared to untreated cultures (FIG. 11K). Moreover, following 24 hours the phagocytosis in untreated cultures was increased, but was still enhanced upon His-tagged SIRPα-41BBL (SEQ ID NO: 5) treatment (FIG. 11K).

Figure 12A:
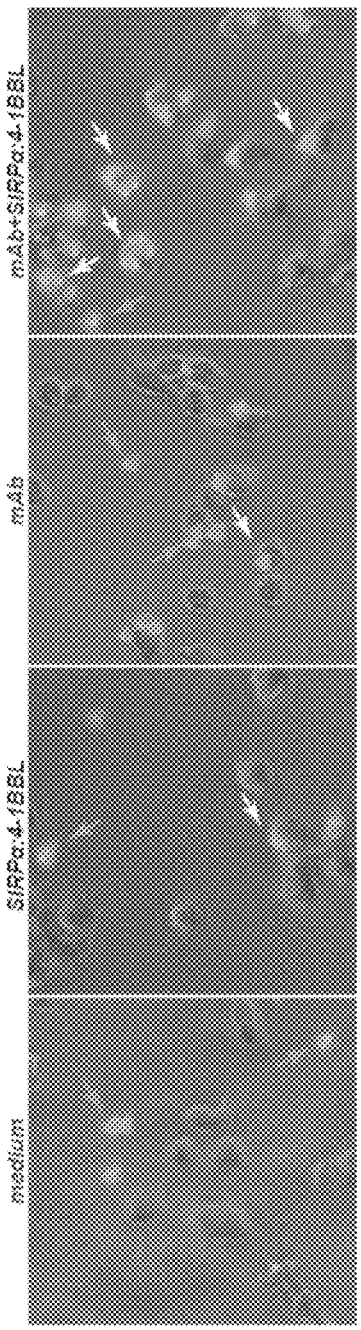
FIGS. 12A-D demonstrate that SIRPα-41BBL potentiates macrophage-mediated phagocytosis.

To further establish the potential of SIRPα-41BBL to stimulate phagocytosis, similar experiments were performed using monocyte-derived macrophages. Shortly, monocytes were enriched from isolated PBMCs from healthy donors by MACS sorting using CD14 magnetic MicroBeads (Miltenyi Biotec). Monocytes were differentiated into macrophages (M0) in RPMI 1640 culture medium+10% FCS supplemented with GM-CSF (50 ng/ml) and M-CSF (50 ng/ml) for 7 days. To generate type 1 macrophages, M0 cells were primed by LPS and IFN-γ for additional 24 hours. Following, the In vitro differentiated macrophages were mixed with B-cell lymphoma cell line U2932 that was pre-stained with the cell proliferation dye V450. Macrophages were mixed with U2932 for 2 hours; and phagocytic uptake of cancer cells was determined by fluorescent microscopy (representative microscopy pictures are shown in FIG. 12A, with dark arrows indicating viable cancer cells and white arrows indicating phagocytosed cancer cells in macrophages). Treatment with His-tagged SIRPα-41BBL (SEQ ID NO: 5) had a limited activity in this setting (FIG. 12B). Treatment with rituximab induced a strong increase in of phagocytosis (FIG. 12C, white diamond squares), which was further augmented by co-treatment with His-tagged SIRPα-41BBL (SEQ ID NO: 5) in the majority of donors at varying rituximab concentrations (FIG. 12C, black diamond squares).

Figure 11L:
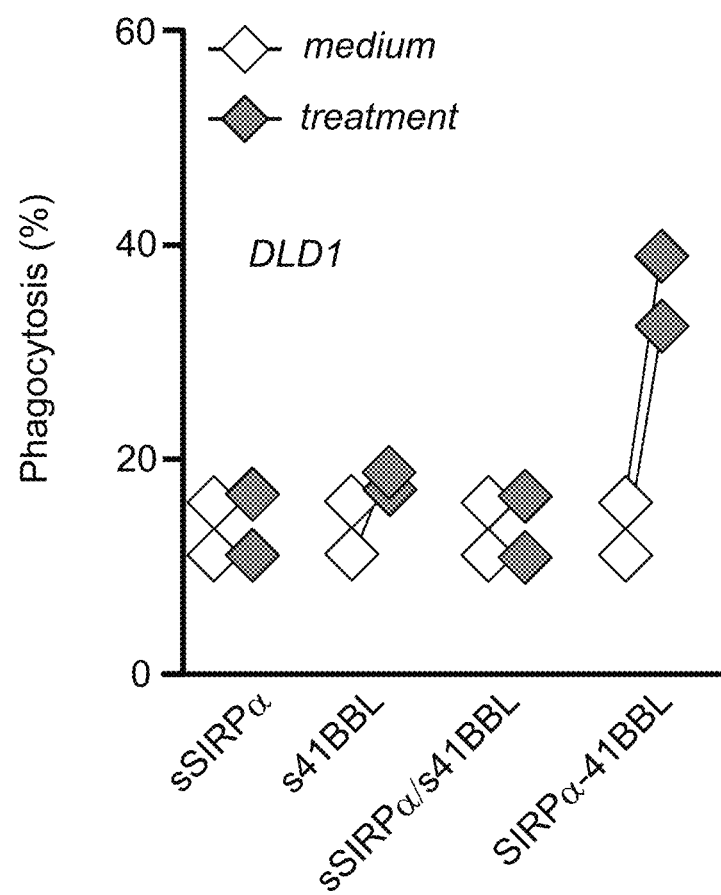
Figure 12D:
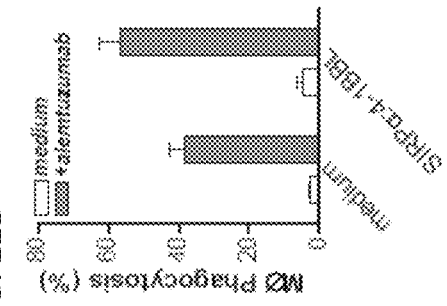
Figure 12C:
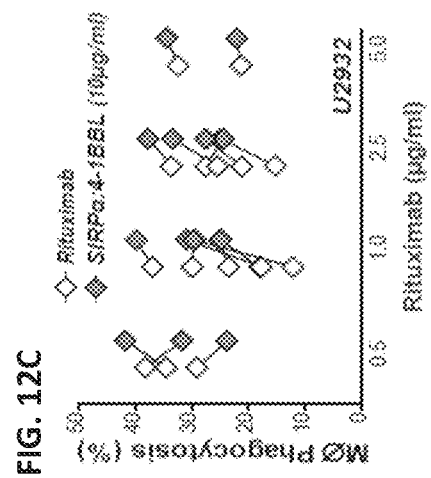
Figure 12B:
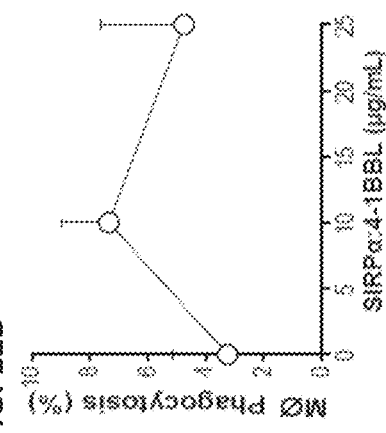

Further, in a mixed culture experiment with primary B-cell chronic lymphocytic leukaemia (B-CLL) blasts and autologous patient-derived macrophages, treatment with the anti-CD52 antibody alemtuzumab (as these blasts were highly positive for CD52) alone induced macrophage-induced phagocytosis of nearly 40% (FIG. 11D); treatment with His-tagged SIRPα-41BBL (SEQ ID NO: 5) alone had a minimal pro-phagocytic activity; but in this primary sample the combination of His-tagged SIRPα-41BBL (SEQ ID NO: 5) and alemtuzumab augmented phagocytosis (by ~20% as compared to treatment with alemtuzumab) (FIG. 12D).

Moreover, the effect of the his-tagged SIRPα-41BBL fusion protein (SEQ ID NO: 5) on phagocytes was superior in comparison to the effects of soluble SIRPα alone, soluble 41BBL alone, or their combination (FIG. 11L).

Taken together, His-tagged SIRPα-41BBL (SEQ ID NO: 5) through its SIRPα domain augments both granulocyte and macrophage-mediated phagocytic uptake of various malignant cell types, including primary malignant cells, particularly in combination treatment with various therapeutic monoclonal antibodies currently in clinical use.

Experiment 5—In-Vivo Proof of Concept

The effects of SIRPα-41BBL, both on the targeting and activation of T, NK and B cells and on the activation of phagocytic and dendritic cells, is tested in-vivo in mouse models. The mouse His-tagged SIRPα-41BBL fusion protein is produced and purified as tagged protein in the same way as the human molecule. Mouse tumor models are generated by injecting mice with mouse cancer cells that are known to form tumors that express mouse CD47. Mice are treated with the mouse or human His-tagged-SIRPα-41BBL fusion protein molecule. Tumor size, mice survival and inflammatory reaction in the tumor site are monitored.

Similar experiments can be performed in a humanized mouse model using human tumors. This model is constructed using mice that are lacking any mouse immune system (Nude/SCID/NSG mice). A human-like immune system is established in these mice by injection of only human T cells or PBMCs or by using genetically engineered mice that possess a fully humanized immune system. The mice are inoculated with human cancer cells and treated with the human His-tagged SIRPα-41BBL molecule. Tumor size, mice survival and inflammatory reaction in the tumor site are monitored in this model as well.

The in-vivo efficacy of His-SIRPα-41BBL can be compared to that of its parts, namely, recombinant SIRPα or 41BBL alone or in combination.

Experiment 5A—SIRPα-41BBL protein inhibits tumor growth in mice inoculated with syngeneic colon carcinoma Materials—

Mice autoclaved food and bedding (Ssniff, Soest, Germany), Female Balb/C mice (Janvier, Saint Berthevin Cedex, France), CT-26 mouse colon carcinoma cell line (ATCC-CRL-2638), anti-mouse PD-1 antibody (BioXcell, West Lebanon, USA), His-tagged SIRPα-41BBL protein (SEQ ID NO: 5) produced as described in Experiment 1A hereinabove, PBS Methods—

Mice were maintained in individually ventilated cages in groups of four mice per cage. The mice received autoclaved food and bedding and acidified (pH 4.0) tap water ad libitum. The animal facility was equipped with an automatic 12 hours light/dark regulation, temperature regulation at 22±2° C., and relative humidity of 50±10%. Female Balb/C mice were inoculated subcutaneously with $1 \times 10^6$ CT-26 cells and treatment started three days later. Following random assignment, 10 animals per group were administered twice weekly with three intravenous injections of His-tagged SIRPα-41BBL protein (SEQ ID NO: 5) (100 µg/injection) or its soluble buffer (PBS). 5 mg/kg anti-mouse PD1 at the same schedule were included as a therapeutic reference (FIG. 13A). All administrations were performed in the morning, without anesthesia. Tumor volume was determined three times per week using caliper measurements, and the individual volumes were calculated by the formula: V=([width]2×length)/2. All animal experiments were done in accordance with the United Kingdom Coordinating Committee on Cancer Research regulations for the Welfare of Animals (Workman et al., Committee of the National Cancer Research Institute. Guidelines for the welfare of animals in cancer research. Br J Cancer 2010; 102:1555-77) and of the German Animal Protection Law and approved by the local responsible authorities (Gen0030/15).

Results—

In this Experiment, the in-vivo effect of SIRPα-41BBL was evaluated using the CT-26 mouse colon cancer model. Treatment of CT-26 inoculated mice with His-tagged SIRPα-41BBL protein (SEQ ID NO: 5) reduced the tumor volume (by about 36% at max) (FIG. 13B).

Experiment 5B—SIRPα-41BBL Protein is Effective for the Treatment of Mice Inoculated with a Syngeneic Leukemic Tumor Materials—

Mice autoclaved food and bedding (Ssniff, Soest, Germany), Female DBA/2 mice (Janvier, Saint Berthevin Cedex, France), P388 Leukaemia cell line (Max-Delbrueck-Center for Molecular Medicine, Berlin, Germany), anti-mouse PD-1 antibody (BioXcell, West Lebanon, USA), His-tagged SIRPα-41BBL protein (SEQ ID NO: 5), PBS Methods—

Mice were maintained in individually ventilated cages in groups of four mice per cage. They received autoclaved food and bedding and acidified (pH 4.0) tap water ad libitum. The animal facility was equipped with an automatic 12 hours light/dark regulation, temperature regulation at 22±2° C., and relative humidity of 50±10%. Female DBA/2 mice were inoculated intraperitoneally with $1 \times 10^6$ P388 cells and treatment started the day after. Following random assignment, ten animals per group were administered every second day with four intravenous injections of His-tagged SIRPα-41BBL protein (SEQ ID NO: 5) (100 µg/injection) or its soluble buffer (PBS). 5 mg/kg anti-mouse PD1 at the same schedule were included as a therapeutic reference. All administrations were performed in the morning, without anesthesia. Mice bearing P388 were weighed daily and once the mice became moribund, they were sacrificed, and the ascites volume was determined. Furthermore, spleen and liver from each mouse was taken and weighed.

All animal experiments were done in accordance with the United Kingdom Coordinating committee on Cancer Research regulations for the Welfare of Animals (Workman et al., committee of the National Cancer Research Institute. Guidelines for the welfare of animals in cancer research. Br J Cancer 2010; 102:1555-77) and of the German Animal Protection Law and approved by the local responsible authorities (Gen0030/1

Results—

In this experiment, the in-vivo effect of SIRPα-41BBL was evaluated using the P388 mouse ascites leukemia model. In this model, spleen weight is a marker for disease severity, due to the fact that the spleen serves as draining lymph node for the ascites. Treatment of P388 mouse leukemia inoculated mice with His-tagged SIRPα-41BBL protein (SEQ ID NO: 5) was effective, as can be seen by the significant reduction in spleen weight (19%, P-value=0.03) (FIG. 14B) pointing of a better disease prognosis.

Experiment 5C—SIRPα-41BBL Protein Decreases Tumor Burden in the BM of NSG Mice Inoculated with Human Leukemia Tumor Materials—

Female NSG (NOD-scid gamma mice) mice at the age of 12-16 weeks (Jackson Laboratory), MV4.11 Acute Myeloid Leukemia cell-line (ATCC-CRL-9591), anti-mouse CD45 antibody (eBioscience, San Diego, Calif., USA), anti-human CD45 antibody (eBioscience, San Diego, Calif., USA), anti-human CD123 antibody (BD Pharmingen, USA), His-tagged SIRPα-41BBL protein (SEQ ID NO: 5) produced as described in Experiment 1A hereinabove, PBS. Human PBMCs were isolated from healthy donor peripheral blood using Ficoll-Paque method (Sigma-Aldrich Israel Ltd.).

Methods—

Mice were maintained in individually ventilated cages in groups of 5 mice per cage. The mice received autoclaved food and bedding and acidified (pH 4.0) tap water ad libitum. The animal facility was equipped with an automatic 12 hours light/dark regulation, temperature regulation at 22±2° C., and relative humidity of 50±10%. Female NSG mice were irradiated with 200 rad 24 hour prior to intravenous inoculation through the tail vein with $7.8 \times 10^6$ MV4.11 cells in a total volume of 200 al PBS. Thirteen (13) days later mice were inoculated through the tail vein with $1.5 \times 10^6$ human PBMCs and treatment started 4 hours later. Following random assignment, 5 animals per group were administered every-other-day (EOD) with four intraperitoneal injections of His-tagged SIRPα-41BBL protein (SEQ ID NO: 5, 100 µg/injection) or its soluble buffer (PBS) (on days 13, 15, 17 and 19) (FIG. 15A). All administrations were performed in the morning, without anesthesia. Twenty-four (24) hours following last injection mice were sacrificed and blood, bone-marrow (BM) and spleen were collected. Spleen was weighted, and BM extracted cells were analyzed by FACS following staining with hCD45, mCD45 and CD123.

All animal experiments were done in accordance with the Hadassa Medical Center Committee regulations for the Welfare of Animals and of the Israeli Animal Protection Law and approved by the local responsible authorities.

Results—

Treatment of MV4.11 inoculated irradiated NSG mice not reconstituted with human PBMCs with His-tagged SIRPα-41BBL protein (SEQ ID NO: 5) did not affect the number of leukemic cells in the BM (FIG. 15B). Treatment of MV4.11 inoculated NSG mice with human PBMCs reduced tumor burden in the bone marrow (by 10%) (FIG. 15B) and did not increase spleen weight (FIG. 15C). However, Treatment of MV4.11 inoculated NSG mice with His-tagged SIRPα-41BBL protein (SEQ ID NO: 5) together with human PBMCs reduced tumor burden in the bone marrow (by 38%) (FIG. 15B) and also increased spleen weight (FIG. 15C). The Increase in spleen weight that was seen only with the combination of His-tagged SIRPα-41BBL protein and human PBMCs is indicative of increased graft versus leukemia (GVL) effect in the BM that was also associated with reduction of leukemia cell number in the BM (FIGS. 15B-C, p value=0.01).

What is claimed is:

1. A Signal regulatory protein α (SIRPα)-4-1BB ligand (41BBL) fusion protein being characterized by a single amino acid linker between said SIRPα and said 41BBL; and/or being in a form of a homo-trimer.

2. The SIRPα-41BBL fusion protein of claim 1, wherein said homo-trimer is at least 140 kD in molecular weight as determined by SDS-PAGE.

3. The SIRPα-41BBL fusion protein of any one of claim 1, wherein the SIRPα-41BBL fusion protein comprises a linker between said SIRPα and said 41BBL.

4. The SIRPα-41BBL fusion protein of claim 3, wherein the linker is not an Fc domain of an antibody or a fragment thereof.

5. The SIRPα-41BBL fusion protein of claim 1, wherein the linker is glycine.

6. The SIRPα-41BBL fusion protein of claim 1, being soluble.

7. The SIRPα-41BBL fusion protein of claim 1, wherein said fusion protein is capable of at least one of:

(i) binding CD47 and 4-1BB;
(ii) activating 4-1BB signaling pathway in a cell expressing said 4-1BB;
(iii) co-stimulating immune cells expressing said 4-1BB; and/or
(iv) enhancing phagocytosis of pathologic cells expressing said CD47 by phagocytes compared to same in the absence of said SIRPα-41BBL fusion protein.

8. The SIRPα-41BBL fusion protein of claim 1, wherein said SIRPα-41BBL fusion protein amino acid sequence comprises SEQ ID NO: 1.

9. The SIRPα-41BBL fusion protein of claim 1, wherein said SIRPα-41BBL fusion protein amino acid sequence consists of SEQ ID NO: 1.

10. A Signal regulatory protein α (SIRPα)-4-1BB ligand (41BBL) fusion protein being characterized by a single amino acid linker between said SIRPα and said 41BBL.

11. A Signal regulatory protein α (SIRPα)-4-1BB ligand (41BBL) fusion protein being in a form of a homo-trimer.

* * * * *